US008715665B2

(12) United States Patent
Janne et al.

(10) Patent No.: US 8,715,665 B2
(45) Date of Patent: May 6, 2014

(54) METHODS FOR TREATING CANCER RESISTANT TO ERBB THERAPEUTICS

(75) Inventors: Pasi A. Janne, Newton, MA (US); Jeffrey Engelman, Chestnut Hill, MA (US); Lewis C. Cantley, Cambridge, MA (US)

(73) Assignees: The General Hospital Corporation, Boston, MA (US); Dana Farber Cancer Institute, Boston, MA (US); Beth Israel Deaconess Medical Center, Boston, MA (US)

( * ) Notice: Subject to any disclaimer, the term of this patent is extended or adjusted under 35 U.S.C. 154(b) by 1002 days.

(21) Appl. No.: 12/450,826

(22) PCT Filed: Apr. 11, 2008

(86) PCT No.: PCT/US2008/004804
§ 371 (c)(1),
(2), (4) Date: Mar. 18, 2010

(87) PCT Pub. No.: WO2008/127710
PCT Pub. Date: Oct. 23, 2008

(65) Prior Publication Data
US 2012/0225870 A1 Sep. 6, 2012

Related U.S. Application Data

(60) Provisional application No. 60/923,384, filed on Apr. 13, 2007.

(51) Int. Cl.
*A61K 39/395* (2006.01)
(52) U.S. Cl.
USPC ..................................... 424/143.1
(58) Field of Classification Search
None
See application file for complete search history.

(56) References Cited

U.S. PATENT DOCUMENTS

| 3,654,090 A | 4/1972 | Hermanus |
| 3,817,837 A | 6/1974 | Rubenstein et al. |
| 3,850,752 A | 11/1974 | Schuurs et al. |
| 4,016,043 A | 4/1977 | Schuurs et al. |
| 4,987,071 A | 1/1991 | Cech et al. |
| 5,143,854 A | 9/1992 | Pirrung et al. |
| 5,288,514 A | 2/1994 | Ellman |
| 5,384,261 A | 1/1995 | Winkler et al. |
| 5,459,039 A | 10/1995 | Modrich et al. |
| 5,587,458 A | 12/1996 | King et al. |
| 5,770,358 A | 6/1998 | Dower et al. |
| 5,807,522 A | 9/1998 | Brown et al. |
| 5,869,245 A | 2/1999 | Yeung |
| 5,877,305 A | 3/1999 | Huston et al. |
| 6,110,462 A | 8/2000 | Barbas et al. |
| 6,197,599 B1 | 3/2001 | Chin et al. |
| 6,232,068 B1 | 5/2001 | Linsley et al. |
| 6,284,764 B1 | 9/2001 | Kath et al. |
| 6,375,903 B1 | 4/2002 | Cerrina et al. |
| 6,465,449 B1 | 10/2002 | Kath et al. |
| 2004/0197332 A1 | 10/2004 | Ullrich et al. |
| 2005/0170439 A1 | 8/2005 | Chan-Hui et al. |
| 2005/0272083 A1 | 12/2005 | Seshagiri |
| 2007/0254295 A1 | 11/2007 | Harvey et al. |
| 2008/0305962 A1 | 12/2008 | Wirtz |
| 2010/0255004 A1 | 10/2010 | DePinho et al. |

FOREIGN PATENT DOCUMENTS

| JP | 2006-519232 | 8/2006 |
| WO | WO-87/06720 | 10/1987 |
| WO | WO-90/11364 A1 | 10/1990 |
| WO | WO-00/34784 A1 | 6/2000 |
| WO | WO-01/64942 A1 | 9/2001 |
| WO | WO-01/77350 A2 | 10/2001 |
| WO | WO-02/32925 A2 | 4/2002 |
| WO | WO 2004/076412 | 9/2004 |
| WO | WO 2006/021881 | 3/2006 |
| WO | WO 2006/021884 | 3/2006 |
| WO | WO-2006/084058 | 8/2006 |
| WO | WO 2006/099396 | 9/2006 |
| WO | WO 2006/110175 | 10/2006 |
| WO | WO 2006/129163 | 12/2006 |
| WO | WO 2007/023307 | 3/2007 |

OTHER PUBLICATIONS

Hynes and Lane, Nature Reviews, 2005, vol. 5 pp. 341-354.*
Ma et al., Cancer Research, 2005, vol. 65, pp. 1479-1488.*
Hynes and Lane, Nature Reviews, 2005, vol. 5, pp. 341-353.*
Marionnet et al., Oncogene, 2003, vol. 22, pp. 3500-3505.*
Engelman et al., "Allelic dilution obscures detection of a biologically significant resistance mutation in EGFR-amplified lung cancer," Journal of Clinical Investigation 116(10):2695-2706 (2006).
Engelman et al., "MET amplification leads to gefitinib resistance in lung cancer by activiating ERBB3 signaling," Science 316(5827):1039-1043 (2007).
Kim et al., "174 POSTER Inhibition of Stat3 overcomes gefitinb resistance caused by T790M mutation of EGFR tyrosine kinase," European Journal of Cancer 4(12):1359-6349 (2006).
Lynch et al., "Activating mutations in the epidermal growth factor receptor underlying responsiveness of non-small-cell lung cancer to gefitinib," New England Journal of Medicine 350(21):2129-2139 (2004).
Smolen et al., "Amplification of MED may identify a subset of cancers with extreme sensitivity to the selective tyrosine kinase inhibitor PHA-665752," Proceedings of the National Academy of Science 103(7):2316-2321 (2006).

(Continued)

*Primary Examiner* — Anne Gussow
*Assistant Examiner* — Mindy G Brown
(74) *Attorney, Agent, or Firm* — Ropes & Gray LLP

(57) ABSTRACT

Provided herein are methods for treating cancer that is resistant to treatment with an anti-ErbB therapeutic agent and which is associated with an activating MET gene mutation or a MET gene amplification. The methods involve administering to a subject a combination of an anti-ErbB therapeutic and an anti-MET therapeutic. Also provided are methods for reducing ErbB mediated signaling or PI3 kinase mediated signaling in a cancer cell.

12 Claims, 14 Drawing Sheets

(56) References Cited

OTHER PUBLICATIONS

Faivre, Sandrine et al., "New paradigms in anticancer therapy: targeting multiple signaling pathways with kinase inhibitors," Seminars in Oncology 33(4):407-420 (2006).
Patyna, Shem et al., "SU14813: a novel multiple receptor tyrosine kinase inhibitor with potent antiangiogenic and antitumor activity," Molecular Cancer Therapeutics 5(7):1774-1782 (2006).
Potapova, Olga et al., "Contribution of individual targets to the antitumor efficacy of the multitargeted receptor tyrosine kinase inhibitor SU11248," Molecular Cancer Therapeutics 5(5):1280-1289 (2006).
Stommel, Jayne M. et al., "Coactivation of receptor tyrosine kinases affects the response of tumor cells to targeted therapies," Science 318(5848):287-290 (2007).
Thurber et al., "Antibody Tumor Penetration: Transport Opposed by Systemic and Antigen-Mediated Clearance," Advanced Drug Delivery Reviews 60(12):1421-1434 (2008).
Willkomm et al., "FDG PET and immunoscintigraphy with 99mTc-labeled antibody fragments for detection of the recurrence of colorectal carcinoma," J Nucl Med. 41(10):657-1663 (2000).
Zwick et al., "Receptor tyrosine kinase signaling as a target for cancer intervention strategies," Endocrine-Related Cancer 8:161-173 (2001).
Akhtar et al., "Cellular uptake and intracellularfate of antisense oligonucleotides" Trends in Cell Biology. 2:139-144 (1992).
Amann et al,. "Aberrant Epidermal Growth Factor Receptor Signaling and Enhanced Sensitivity to EGFR Inhibitors in Lung Cancer". Cancer Res 65(1) 226-235 (2005).
Balak et al., "Novel D761Y and Common Secondary T790M Mutations in Epidermal Growth Factor Receptor—Mutant Lung Adenocarcinomas with Acquired Resistance to Kinase Inhibitors". Clin Cancer Res 12(21) 6494-6501 (2006).
Bean et al., "MET amplification occurs with or without T790M mutations in EGFR mutant lung tumors with acquired resistance to gefitinib or erlotinib". PNAS 104(52) 20932-20937 (2007).
Begley "Delivery of therapeutic agents to the central nervous system: the problems and the possibilities" Pharmacology & Therapeutics 104:29-45 (2004).
Cariello et al., "Resolution of a missense mutant in human genomic DNA by denaturing gradient gel electrophoresis and direct sequencing using in vitro DNA amplification: HPRT Munich". Am J. Hum Genet. 42(5):726-734 (1988).
Chen et al., "Synthesis of oligodeoxyribonucleotide N3'→P5' phosphoramidates" Nucleic Acids Research. 23(14): 2661-2668 (1995).
Christensen et al., "Cytoreductive antitumor activity of PF-2341066, a novel inhibitor of anaplastic lymphoma kinase and c-Met, in experimental models of anaplastic large-cell lymphoma" Mol. Cancer Ther 6(12): 3314-3322 (2007).
Cotton et al., "Reactivity of cytosine and thymine in single-base-pair mismatches with hydroxylamine and osmium tetroxide and its application to the study of mutations" Proc. Natl. Acad. Sci. USA 85: 4397-4401 (1988).
Debiec-Rychter et al., "Mechanisms of Resistance to Imatinib Mesyiate in Gastrointestinal Stromal Tumors and Activity of the PKC412 inhibitor Against Imatinib-Resistant Mutants" Gastroenterology 128:270-279 (2005).
Del Tito et al., "Automated fluorescent analysis procedure for enzymatic mutation detection". Clinical Chemistry 44(4) 731-739 (1998).
Demetri et al., "Efficacy and Safety of Imatinib Mesylate in Advanced Gastrointestinal Stromal Tumors". N Engl J Med 347(7) 472-480 (2002).
DeWitt et al ""Diversomers": An approach to nonpeptide, nonoligomeric chemical diversity". Proc. Natl. Acad. Sci. USA vol. 90: 6909-6913 (1993).
Donato et al., "BCR-ABL independence and LYN kinase overexpression in chronic myelogenous leukemia cells selected for resistance to STI571". Blood 101(2): 690-698 (2003).
Druker et al., "Activity of a Specific Inhibitor of the BCR-ABL Tyrosine Kinase in the Blast Crisis of Chronic Myeloid Leukemia and Acute Lymphoblastic Leukemia with the Philadelphia Chromosome". N Engl J Med. 344(14): 1038-1042 (2001).
Engleman et al., "ErbB-3 mediates phosphoinositide 3-kinase activity in gefitinib-sensitive non-small cell lung cancer cell lines". PNAS 102(10): 3788-3793 (2005).
Fuja et al., "A multiplex microsphere bead assay for comparative RNA expression analysis using flow cytometry" Journal of Biotechnology 108:193-205 (2004).
Gibson et al., "A Novel Method for Real Time Quantitative RT-PCR" Genome Res. 6: 995-1001 (1996).
Heid et al., "Real time quantitative PCR" Genome Res. 6:986-994 (1996).
Heidenreich et al., "RNase H-independent antisense activity of oligonucleotide N3'→P5' phosphoramidates" Nucleaic Acids Research 25(4): 776-780 (1997).
Henirich et al., "Molecular Correlates of Imatinib Resistance in Gastrointestinal Stromal Tumors". Journal of Clinical Oncology 24(29): 4764-4774 (2006).
Hochhaus et al., "Molecular and chromosomal mechanisms of resistance to imatinib (STI571) therapy". Leukemia vol. 16: 2190-2196 (2002).
Hosse et al., "A new generation of protein display scaffolds for molecular recognition". Proten Science 15(14): 14-27 (2006).
Hynes et al., "ERBB receptors and cancer: the complexity of targeted inhibitors". Nature Reviews Cancer 5: 341-354 (2005).
Inoue et al., "Prospective Phase II Study of Gefitinib for Chemotherapy—Naive Patients With Advanced Non-Small-Cell Lung Cancer With Epidermal Growth Factor Receptor Gene Mutations". Journal of Clinical Oncology 24(21): 3340-3346 (2006).
Janne et al., "A Rapid and Sensitive Enzymatic Method for Epidermal Growth Factor ReceptorMutation Screening". Clin Cancer Res 12(3): 751-758 (2006).
Jo et al., "Cross-talk between Epidermal Growth Factor Receptor and c-Met Signal Pathways in Transformed Cells". The Journal of Biological Chemistry 275(12): 8806-8811 (2000).
Kosaka et al., "Analysis of Epidermal Growth Factor Receptor Gene Mutation in Patients with Non-Small Cell Lung Cancer and Acquired Resistance to Gefitinib". Clin Cancer Res 12(19): 5764-5769 (2006).
Kosaka et al., "Mutations of the Epidermal Growth Factor Receptor Gene in Lung Cancer: Biological and Clinical Implications". Cancer Research vol. 64: 8919-8923 (2004).
Kwak et al,. "Irreversible inhibitors of the EGF receptor may circumvent acquired resistance to gefitinib". PNAS 102(21): 7665-7670 (2005).
Kwoh et al., "Transcription-based amplification system and detection of amplified human immunodeficiency virus type 1 with a bead-based sandwich hybridization format". Proc. Natl. Acad. Sci USA vol. 86: 1173-1177 (1989).
Maatta et al., "Proteolytic Cleavage and Phosphorylation of a Tumorassociated ErbB4 Isoform Promote Ligand-independent Survival and Cancer Cell Growth. Molecular Biology fo the Cell vol. 17: 67-79 (2006).
Martinez et al., "Single-Stranded Antisense siRNAs Guide Target RNA Cleavage in RNAi". Cell vol. 110: 563-574 (2002).
McManus et al., "Gene silencing using micro-RNA designed hairpins" RNA 8:842-80 (2002).
Mukohara et al., "Differential Effects of Gefitinib and Cetuximab on Non-small-cell Lung Cancers Bearing Epidermal Growth Factor Receptor Mutations". Journal of the National Cancer Institute 97(16):1185-1194 (2005).
Mukohara et al., "Inhibition of the Met Receptor in Mesothelioma". Clin Cancer Res. 11(22): 8211-8130 (2005).
Orita et al., "Detection of polymorphisms of human DNA by gel electrophoresis as single-strand conformation polymorphisms". Proc. Natl. Acad. Sci. USA vol. 86: 2766-2770 (1989).
Paddison et al., "Short hairpin RNAs (shRNAs) induce sequence-specific silencing in mammalian cells" Genes & Development 16: 948-958 (2002).
Paez et al., "*EGFR* Mutations in Lung Cancer: Correlation with Clinical Response to Gefitinib Therapy". Science vol. 304: 1497-1500 (2004).

(56) References Cited

OTHER PUBLICATIONS

Park et al., "Presence of autocrine hepatocyte growth factor-Met signaling and its role in proliferation and migration of SNU-484 gastric cancer cell line". Experimental and Molecular Medicine 37(2): 213-219 (2005).

Pocaly et al, "Overexpression of the heat-shock protein 70 is associated to imatinib resistance in chronic myeloid leukemia" Leukemia 12: 93-201 (2007).

Ptasznik et al., "Short interfering RNA (siRNA) targeting the Lyn kinase induces apoptosis in primary, and drug-resistant, BCR-ABL1(+) leukemia cells" Nature Medicine 10(11) 1187-1198 (2004).

Ruano et al., "Direct haplotyping of chromosomal segments from multiple heterozygotes via allele-specific PCR amplification". Nucleic Acids Research 17(20):8392 (1989).

Schmajuk et al., "Antisense Oligonucleotides with Different Backbones". The Journal of Biological Chemistry 274(31): 21783-21789 (1999).

Sergina et al., "Escape from HER family tyrosine kinase inhibitor therapy by the kinase inactive HER3" Nature 445(7126): 437-441 (2007).

Shenk et al., "Biochemical Method for Mapping Mutational Alterations in DNA with SI Nuclease: The Location of Deletions and Temperature-Sensitive Mutations in Simian Virus 40" Proc. Nat. Acad. Sci USA 72(3): 989-993 (1975).

Shibata et al., "Genetic Classification of Lung Adenocarcinoma Based on Array-Based Comparative Genomic Hybridization Analysis: Its Association with Clinicopathologic Features". Clin Cancer Res 11(17): 6178-6185 (2005).

Shigematsu et al., "Clinical and Biological Features Associated With Epidermal Growth Factor Receptor Gene Mutations in Lung Cancers". Journal of the National Cancer Institute 97(5): 339-346 (2005).

Tracy et al "Gefitinib Induces Apoptosis in the EGFRL858R Non-Small-Cell Lung Cancer Cell Line H3255". Cancer Research vol. 64: 7241-7244 (2004).

Walker et al., "Isothermal in vitro amplification of DNA by a restriction enzyme/DNA polymerase system". Proc. Natl. Acad. Sci USA vol. 89: 392-396 (1992).

Weidner et al., "Interaction between Gab1 and the c-Met receptor tyrosine kinase is responsible for epithelial morphogensis". Nature vol. 384: 173-176 (1996).

Winter et al., "A method to detect and characterize point mutations in transcribed genes: Amplification and overexpression of the mutant c-Ki-*ras* allele in human tumor cells" Proc. Natl. Acad. Sci. USA 82: 7575-7579 (1985).

Yakes et al., "Herceptin-induced Inhibition of Phosphatidylinositol-3 Kinase and Akt Is Required for Antibody-mediated Effects on p27, Cyclin D1, and Antitumor Action". Cancer Research 62:4132-4141 (2002).

Yu et al., "RNA interference by expression of short-interfering RNAs and hairpin RNAs in mammalian cells" PNAS 99(9): 6047-6052 (2002).

Zhao et al., "An Integrated View of Copy Number and Allelic Alterations in the Cancer Genome Using Single Nucleotide Polymorphism Arrays". Cancer Research 64: 3060-3071 (2004).

Zhao et al., "Homozygous Deletions and Chromosomes Amplifications in Human Lung Carcinomas Revealed by Single Nucleotide Polymorphism Array Analysis". Cancer Research 65(13): 5561-5570 (2005).

Lynch TJ, Wright CD, Choi NC, Aquino SL, Mark EJ. N Engl J Med. Aug. 19, 2004;351(8):809-17. Case records of the Massachusetts General Hospital. Weekly clinicopathological exercises. Case 26-2004. A 56-year-old woman with cough and a lung nodule.

Christensen et al., "c-Met as a target for human cancer and characterization of inhibitors for therapeutic intervention," Cancer Letters 225(1):1-26 (2005).

Fry, "Inhibition of the epidermal growth factor receptor family of tyrosine kinases as an approach to cancer chemotherapy: progression from reversible to irreversible inhibitors," Pharmacology and Therapeutics 82(2/3):207-218 (1999).

Lutterbach et al., "Lung Cancer Cell Lines Harboring MET Gene Amplification Are Dependent on Met for Growth and Survival," Cancer Research 67(5):2081-2088 (2007).

\* cited by examiner

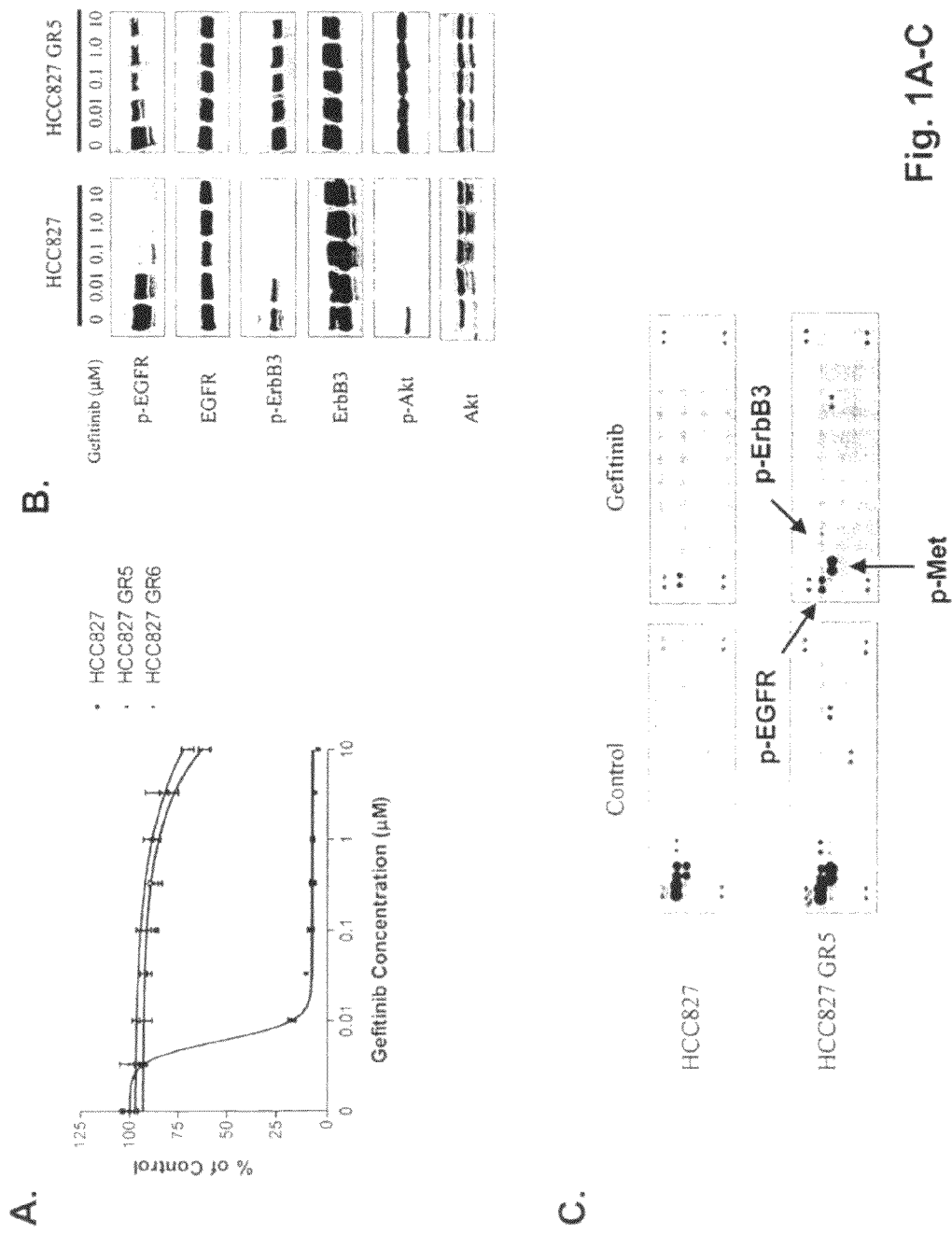
Fig. 1A-C

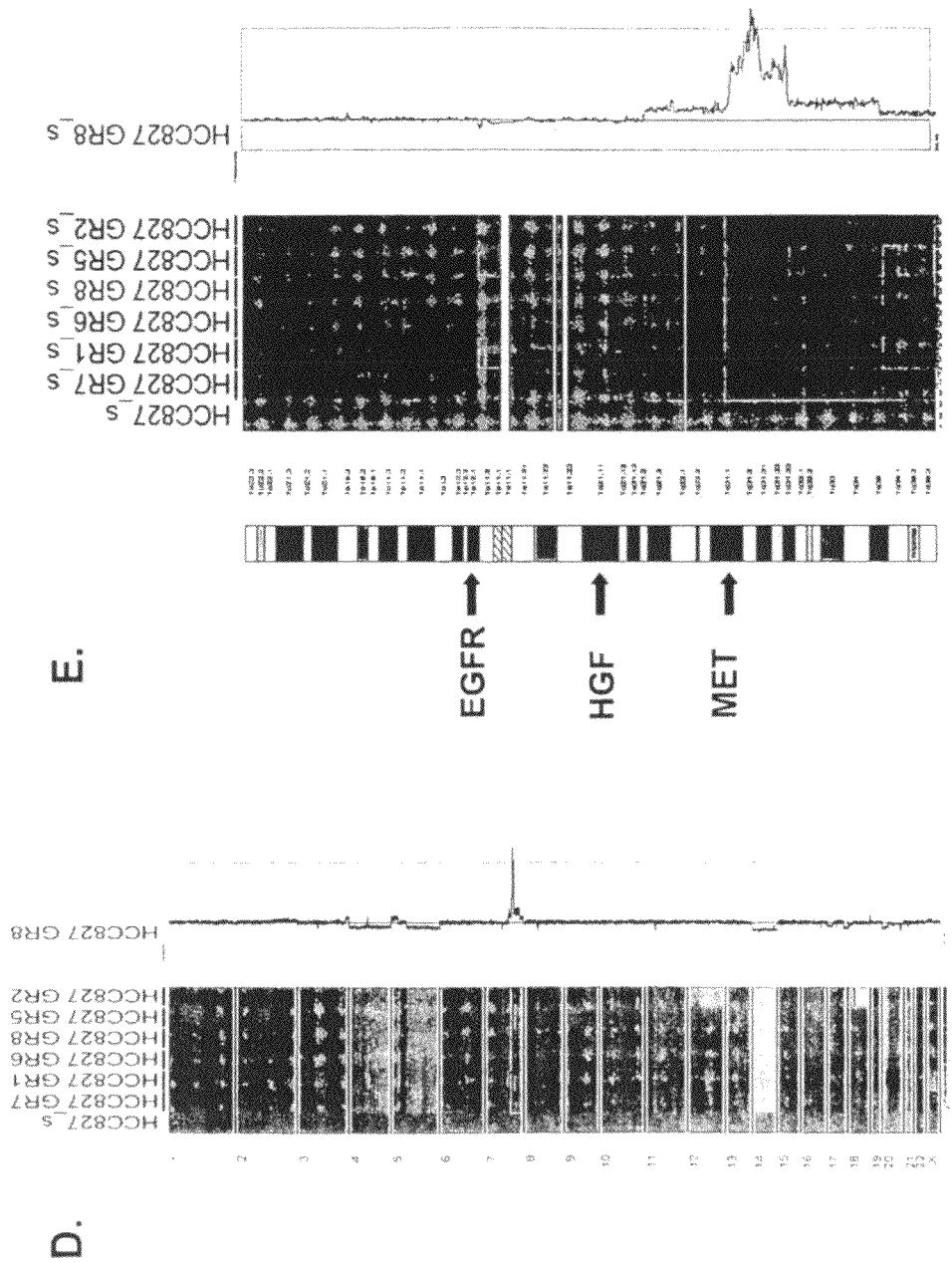

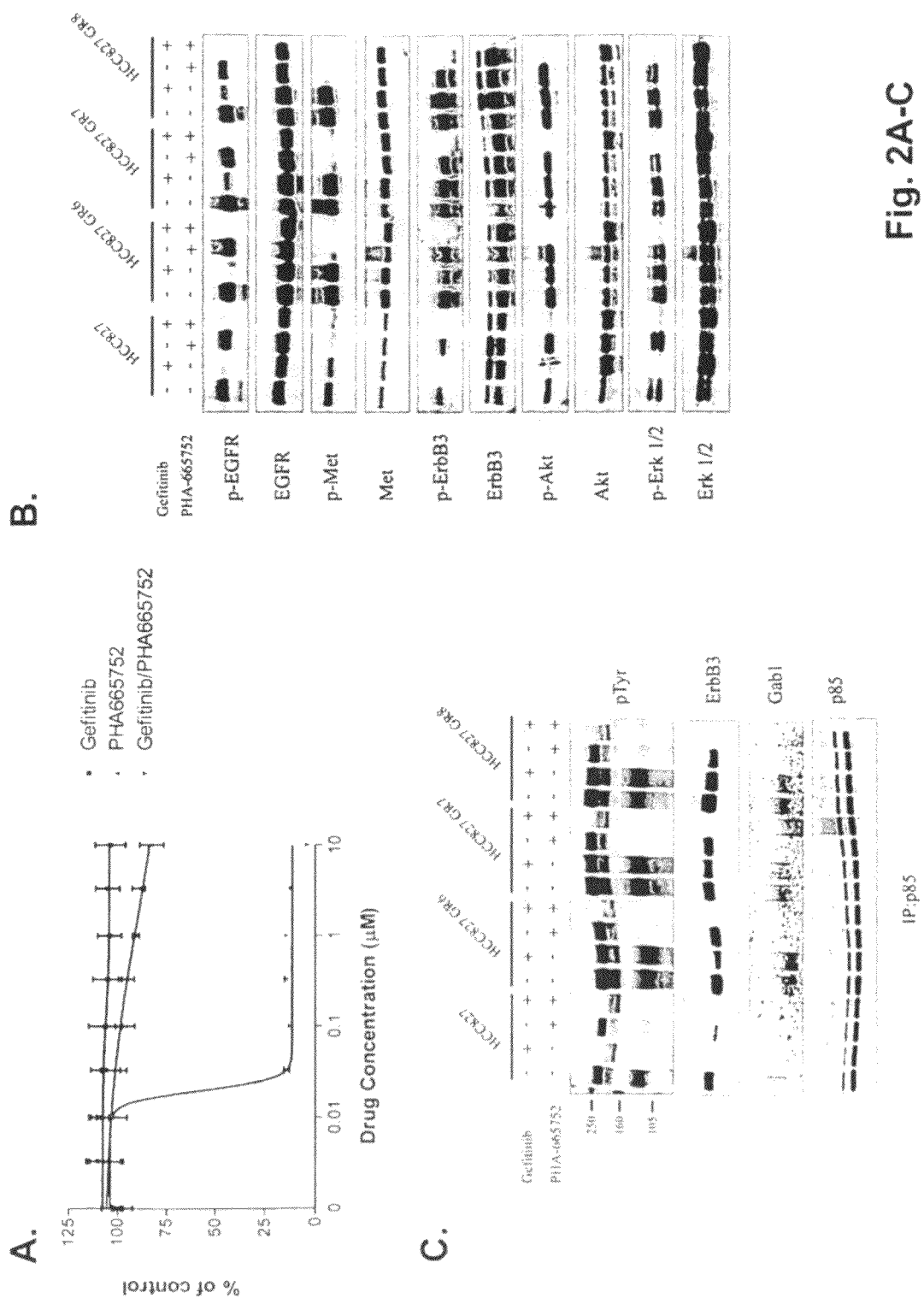
Fig. 2A-C

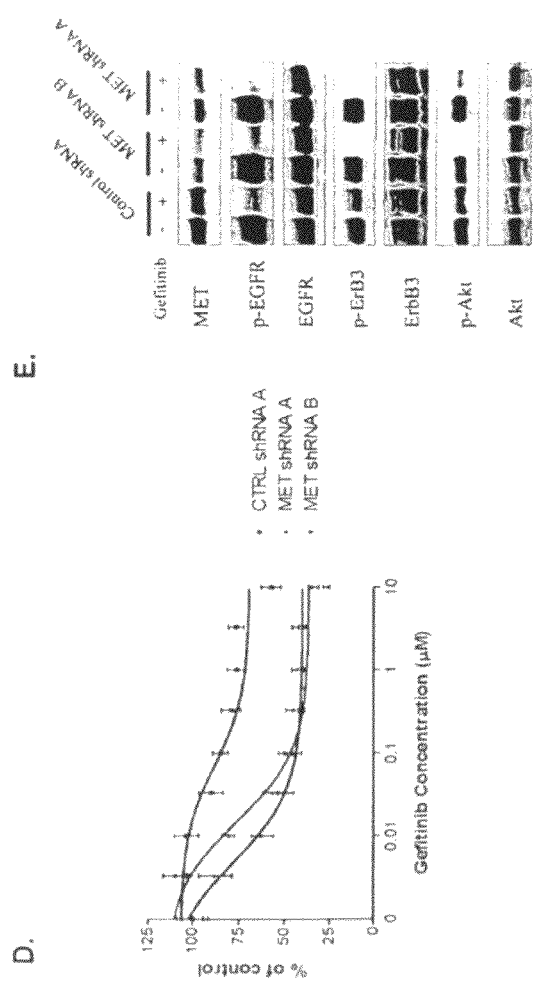
Fig. 2D-E

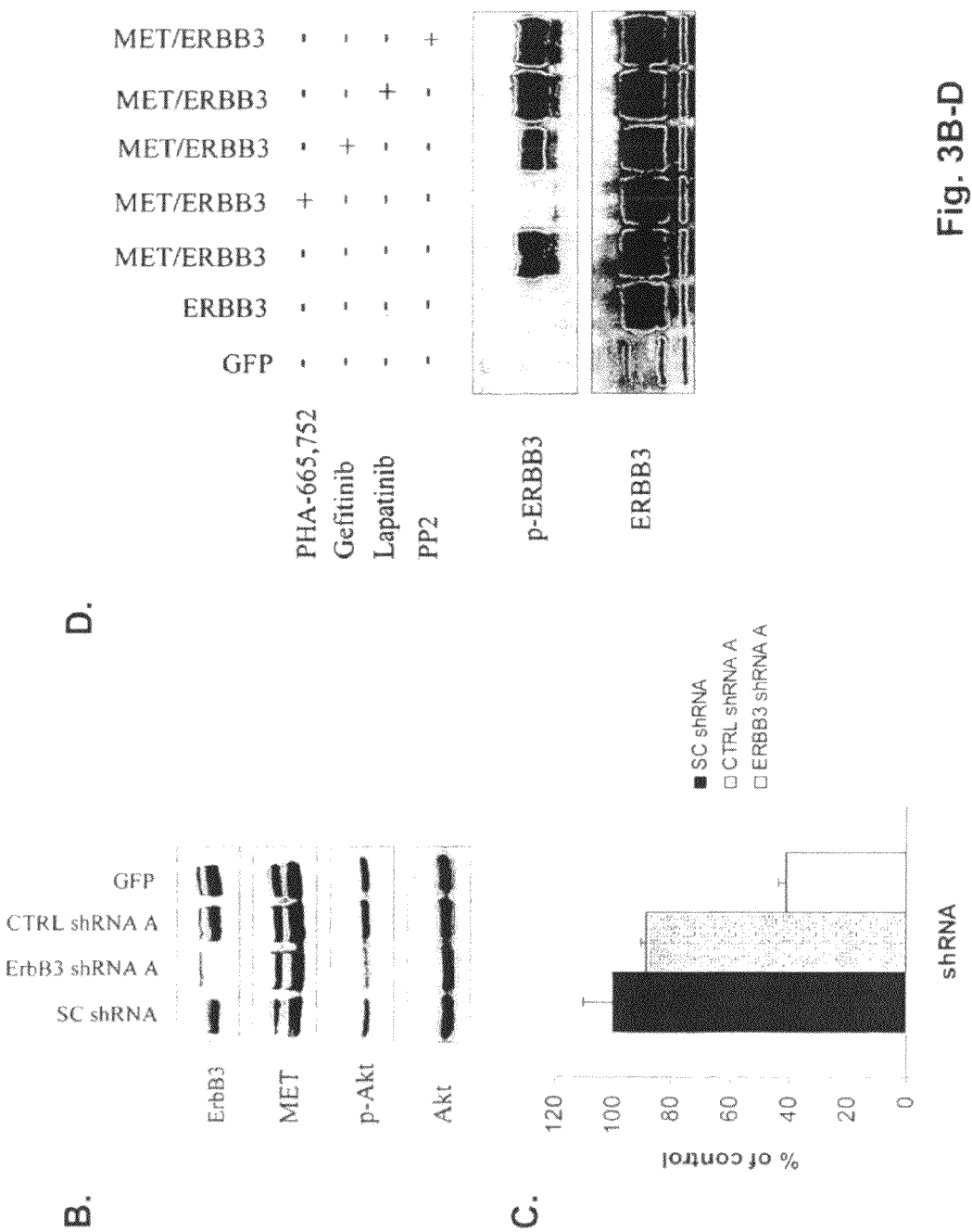
Fig. 3B-D

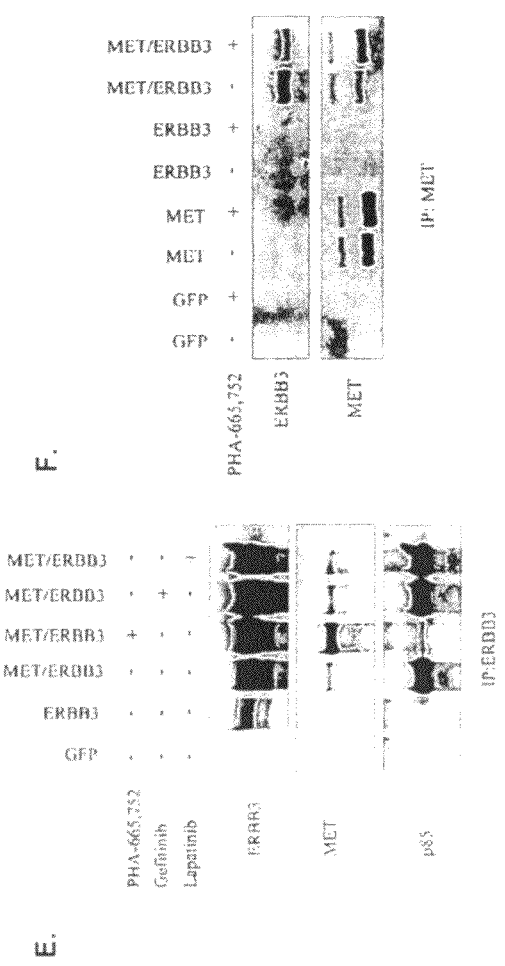
Fig. 3E-F

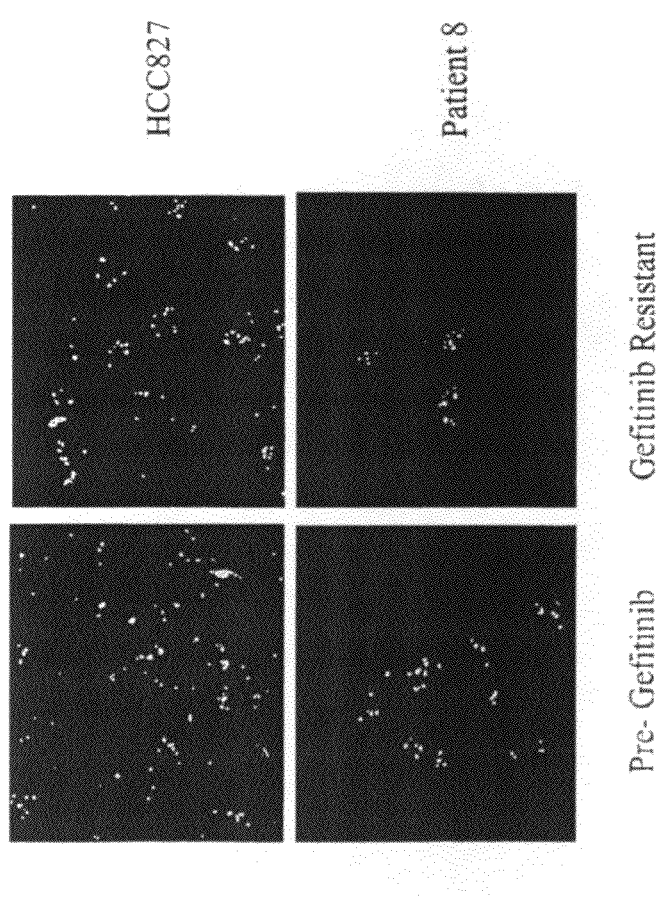

| Patient | Specimen | Type | EGFR mutation | T790M | Method | Result |
|---|---|---|---|---|---|---|
| *Paired Specimens* | | | | | | |
| 1 | Pre-gefitinib | Primary lung cancer | L858R | No | QPCR | 2.10 (0.27) |
|   | Post-gefitinib | Pleural effusion | L858R | No | QPCR | 5.83 (1.41)* |
| 2 | Pre-gefitinib | Primary lung cancer | Del L747_P753 ins S | No | QPCR | 1.83 (0.45) |
|   | Post-gefitinib | Cervical node | Del L747_P753 ins S | Yes | QPCR | 1.97 (015) |
| 3 | Pre-gefitinib | Primary lung cancer | Del L747_P753 ins S | No | QPCR | 1.87 (0.38) |
|   | Post-gefitinib | Primary lung cancer | Del L747_P753 ins S | Yes | QPCR | 1.75 (0.94) |
| 4 | Pre-gefitinib | Primary lung cancer | Del L747_E749, A750P | No | QPCR | 3.07 (0.81) |
|   | Post-gefitinib | Pleural biopsy | Del L747_E749, A750P | Yes | QPCR | 3.17 (0.63) |
| 5 | Pre-gefitinib | Lymph Node | Del L747_S752del,E746V | No | FISH | 0% |
|   | Post-gefitinib | Brain | Del L747_S752del,E746V | No | FISH | 0% |
| 6 | Pre-gefitinib | Pleura | Del L747_E749del, A750P | No | FISH | 1% |
|   | Post-gefitinib | Pericardium | Del L747_E749del, A750P | No | FISH | 2% |
| 7 | Pre-gefitinib | Pleura | Del L747_E749del, A750P | No | FISH | 0% |
|   | Post-gefitinib | Liver | Del L747_E749del, A750P | Yes | FISH | 3% |
| 8 | Pre-gefitinib | Lung | Del E746_A750 | No | FISH | 0% |
|   | Post-gefitinib | Lymph node | Del E746_A750 | No | FISH | 26%* |
| *Post-treatment Specimens* | | | | | | |
| 9 | Post-gefitinib | Pleural effusion | Del E746_A750 | No | QPCR | 2.30 (0.25) |
| 10 | Post-gefitinib | Axilary lymph node | L858R | No | QPCR | 1.98 (0.48) |
| 11 | Post-gefitinib | Primary lung cancer | L858R | Yes | QPCR | 1.92 (0.46) |
| 12 | Post-gefitinib | Primary lung cancer | Del L747_T751,K754E | Yes | QPCR | 3.90 (0.61) |
|    | Post-gefitinib | Mediastinal lymph node | Del L747_T751,K754E | No | QPCR | 6.58 (1.35)* |
| 13 | Post-gefitinib | Primary lung cancer | L858R | Yes | QPCR | 58.21 (7.69)* |
| 14 | Post-gefitinib | Lung Metastasis | L858R | Yes | QPCR | 1.86 (0.23) |
| 15 | Post-gefitinib | Primary lung cancer | L858R | No | QPCR | 1.92 (0.23) |
| 16 | Post-erlotinib | Lung metastasis | Del E746_A750 | Yes | FISH | 0% |
| 17 | Post-gefitinib | Lung metastasis | Del L747_T751 | Yes | FISH | 0% |
| 18 | Post-gefitinib | Lung metastasis | L858R | Yes | FISH | 0% |

Patients with EGFR T790M 55% (10/18)
Patients with MET amplification 4/18 (22%)

Fig. 5

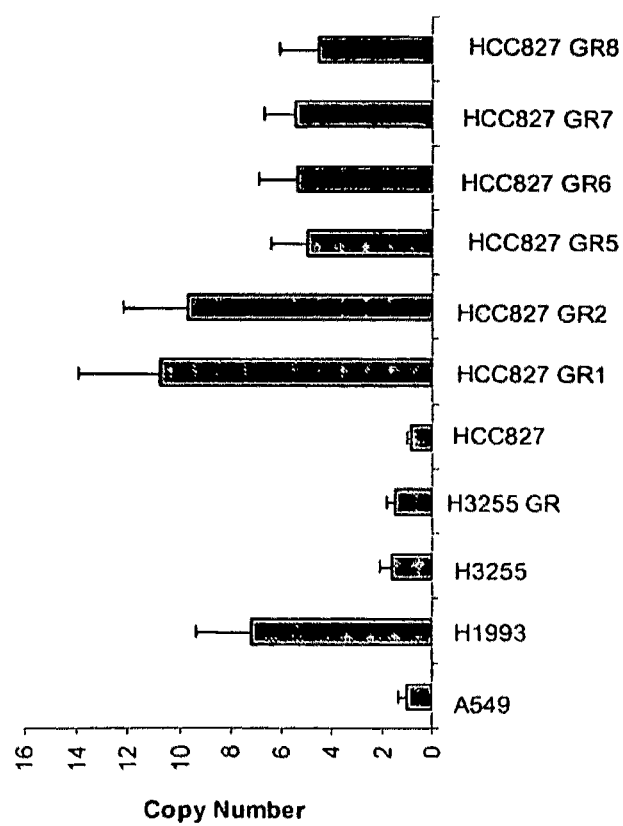

| Gene | Chromosomal Location | Mean Fold Change |
| --- | --- | --- |
| transcription factor EC | 7q31.2 | 48.42 |
| interleukin 1 receptor accessory protein-like 1 | Xp22.1-p21.3 | 33.50 |
| transcription factor EC | 7q31.2 | 27.20 |
| S100 calcium binding protein A4 | 1q21 | 20.34 |
| mucin 20, cell surface associated | N/A | 19.00 |
| phosphodiesterase 2A, cGMP-stimulated | 11q13.4 | 18.93 |
| met proto-oncogene | 7q31 | 16.41 |
| Capping protein (actin filament) muscle Z-line, alpha 2 | 7q31.2-q31.3 | 15.92 |
| collagen, type VI, alpha 1 | 21q22.3 | 15.01 |
| transcription factor EC | 7q31.2 | 14.99 |
| met proto-oncogene | 7q31 | 13.85 |
| collagen, type VI, alpha 2 | 21q22.3 | 13.63 |
| ets variant gene 1 | N/A | 13.60 |
| interleukin 1 receptor accessory protein-like 1 | Xp22.1-p21.3 | 13.27 |
| family with sequence similarity 3, member C | N/A | 12.77 |
| met proto-oncogene | 7q31 | 11.99 |
| CDNA: FLJ21769 fis, clone COLF7354 | N/A | 11.12 |
| mucin 20, cell surface associated | N/A | 10.77 |
| high mobility group AT-hook 1 | N/A | 10.38 |
| Ras-related associated with diabetes | 16q22 | 9.83 |

Fig. 8

| Patient | Specimen | Type | Cells with > 2 MET > CEP 7 | Cells with > 3 MET > CEP 7 |
|---|---|---|---|---|
| 5 | Pre-gefitinib | Lymph Node | 2% | 0% |
|  | Post-gefitinib | Brain | 1% | 0% |
| 6 | Pre-gefitinib | Pleura | 3% | 0% |
|  | Post-gefitinib | Pericardium | 2% | 0% |
| 7 | Pre-gefitinib | Pleura | 0% | 0% |
|  | Post-gefitinib | Liver | 4% | 3% |
| 8 | Pre-gefitinib | Lung | 3% | 0% |
|  | Post-gefitinib | Lymph node | 59% | 26% |
| 16 | Post-erlotinib | Lung metastasis | 4% | 2% |
| 17 | Post-gefitinib | Lung metastasis | 0% | 0% |
| 18 | Post-gefitinib | Lung metastasis | 0% | 0% |

Fig. 9

METHODS FOR TREATING CANCER RESISTANT TO ERBB THERAPEUTICS

RELATED APPLICATIONS

This application is a national stage filing under 35 U.S.C. §371 of International Application No. PCT/US2008/004804, filed Apr. 11, 2008, which claims the benefit of U.S. Provisional Application No. 60/923,384, filed Apr. 13, 2007, which application is hereby incorporated by reference in its entirety. International Application No. PCT/US2008/004804 was published under PCT Article 21(2) in English.

GOVERNMENT SUPPORT

This invention was made with government support under Grant Numbers RO1CA114465 and K08CA120060-01 awarded by the National Institutes of Health. The government has certain rights in this invention.

BACKGROUND

Lung cancer is the leading cause of cancer death accounting for one third of all deaths worldwide. Non-small cell lung cancer (NSCLC) accounts for ~75-85% of all histotypes of lung cancer, small cell lung cancer (SCLC) accounting for the remainder. Despite extensive preclinical and clinical research, the overall prognosis for patients with NSCLC remains poor, with a 5-year survival rate of only 14%.

In recent years, knowledge concerning the molecular mechanisms underlying cellular transformation and development of cancer has been greatly expanded. Therapeutic agents have been discovered that target tyrosine kinase receptors, such as the ErbB receptors, which are involved in a variety of cancers, including lung cancer. In particular, agents that target the epidermal growth factor receptor (EGFR), an ErbB receptor, have been developed. While small molecule EGFR targeted therapies, including EGFR-tyrosine kinase inhibitors (TKI) ZD1839 (Iressa™) and erlotinib (Tarceva™), have displayed good initial clinical results, tumor cells frequently develop resistance over time and may become non responsive to the therapy. New approaches are needed to treat patients suffering from a cancer, such as NSCLC, that is not responsive to traditional TKI therapies.

SUMMARY

In one aspect, the invention provides a method for treating a subject suffering from a cancer that is resistant to treatment with an anti-ErbB therapeutic, comprising administering to the subject an anti-ErbB therapeutic and an anti-MET therapeutic.

In certain embodiments, the cancer may be, for example, lung cancer, brain cancer, breast cancer, head and neck cancer, colon cancer, ovarian cancer, gastric cancer, or pancreatic cancer. In an exemplary embodiment, the cancer is non-small cell lung cancer (NSCLC).

In certain embodiments, the subject may have an ErbB activating mutation or gene amplification (e.g., a EGFR, ErbB2, ErbB3, or ErbB4 activating mutation or gene amplification). In certain embodiments, the subject may have a MET activating mutation or a MET gene amplification. In certain embodiments, the subject may have both an ErbB activating mutation or gene amplification and a MET activating mutation or gene amplification.

In certain embodiments, the cancer may be resistant to treatment with one or more of the following anti-ErbB therapeutics: an anti-EGFR therapeutic, an anti-ErbB2 therapeutic, an anti-ErbB3 therapeutic, or an anti-ErbB4 therapeutic. The anti-ErbB therapeutic to which the cancer is resistant may be, for example, a small molecule therapeutic, a nucleic acid therapeutic, or a protein therapeutic. In certain embodiments, the cancer may be resistant to treatment with an anti-ErbB antibody, an siRNA targeted to an ErbB gene, or an ErbB kinase inhibitor. In an exemplary embodiment, the cancer is resistant to treatment with an EGFR kinase inhibitor. In certain embodiments, the cancer is resistant to treatment with one or more of the following anti-EGFR therapeutics: gefitinib, erlotinib, lapatinib, PF00299804, CI-1033, EKB-569, BIBW2992, ZD6474, AV-412, EXEL-7647, HKI-272, cetuximab, pantinumumab, or trastuzumab.

In certain embodiments, one or more of the following anti-ErbB therapeutics is administered to the subject: an anti-EGFR therapeutic, an anti-ErbB2 therapeutic, an anti-ErbB3 therapeutic, or an anti-ErbB4 therapeutic. Suitable anti-ErbB therapeutics for administration to the subject include, for example, small molecule therapeutics, nucleic acid therapeutics, or protein therapeutics. In an exemplary embodiment, one or more of the following anti-EGFR therapeutics is administered to the subject: gefitinib, erlotinib, lapatinib, PF00299804, CI-1033, EKB-569, BIBW2992, ZD6474, AV-412, EXEL-7647, HKI-272, cetuximab, pantinumumab, or trastuzumab.

In certain embodiments, one or more of the following anti-MET therapeutics is administered to the subject: a small molecule therapeutic, a nucleic acid therapeutic, or a protein therapeutic. In an exemplary embodiment, one or more of the following anti-MET therapeutics is administered to the subject: PHA-665,752, SU11274, SU5416, PF-02341066, XL-880, MGCD265, XL184, ARQ 197, MP-470, SGX-523, JNJ38877605, AMG 102, or OA-5D5.

In certain embodiments, an anti-ErbB therapeutic and an anti-MET therapeutic are administered simultaneously to the subject. The anti-ErbB therapeutic and the anti-MET therapeutic may be administered to the subject as a coformulation.

In certain embodiments, the methods for treating a subject suffering from a cancer that is resistant to treatment with an anti-ErbB therapeutic may further comprise administering at least one additional treatment to said subject. Exemplary treatments include, for example, administration of an additional therapeutic agent, radiation, photodynamic therapy, laser therapy, or surgery.

In certain embodiments, the subject being treated may be a mammal, such as, for example, a human.

In another aspect, the invention provides a method for treating a subject suffering from a cancer associated with an ErbB activating mutation or an ErbB gene amplification, wherein the subject has developed a resistance to treatment with an anti-ErbB therapeutic, comprising determining whether the subject has elevated MET activity and/or levels (for example, a MET activating mutation or a MET gene amplification), and administering to those subjects having a MET activating mutation or a MET gene amplification an anti-ErbB therapeutic and an anti-MET therapeutic.

In another aspect, the invention provides a method for treating a subject suffering from a cancer associated with an ErbB activating mutation or an ErbB gene amplification, comprising: (i) monitoring a subject being treated with an anti-ErbB therapeutic to determine if the subject develops elevated MET levels and/or activity (for example, a MET activating mutation or a MET gene amplification), and (ii) modifying the treatment regimen of the subject to include an anti-MET therapeutic in addition to the anti-ErbB therapeutic where the subject has developed a MET activating mutation or a MET gene amplification.

In another aspect, the invention provides a method for treating a subject suffering from a cancer associated with an ErbB activating mutation or an ErbB gene amplification, comprising: (i) monitoring a subject being treated with anti-ErbB therapeutic to determine if the subject develops a resistance to the inhibitor, (ii) testing the subject to determine whether the subject has elevated MET levels and/or activity (such a as a MET activating mutation or a MET gene amplification), and (iii) modifying the treatment regimen of the subject to include an anti-MET therapeutic in addition to the anti-ErbB therapeutic where the subject has a MET activating mutation or a MET gene amplification. In certain embodiments, the patient with elevated MET levels and/or activity has elevated HGF levels and/or activity.

In another aspect, the invention provides a method for evaluating an anti-ErbB therapeutic, comprising: (i) monitoring a population of subjects being treated with an anti-ErbB therapeutic to identify those subjects that develop a resistance to the therapeutic, (ii) testing the resistant subjects to determine whether the subjects have a MET activating mutation or a MET gene amplification, and (iii) modifying the treatment regimen of the subjects to include an anti-MET therapeutic in addition to the anti-ErbB therapeutic where the subjects have a MET activating mutation or a MET gene amplification.

In another aspect, the invention provides a method for reducing ErbB phosphorylation in a cancer cell, wherein said cancer cell has acquired resistance to an anti-ErbB therapeutic, and wherein said cell comprises a MET activating mutation or a MET gene amplification, comprising the step of contacting the cell with an anti-MET therapeutic and an anti-ErbB therapeutic. In certain embodiments, ErbB may be ErbB-3 and the anti-ErbB therapeutic may be an anti-ErbB-3 therapeutic.

In another aspect, the invention provides a method for reducing PI3K mediated signaling in a cancer cell, wherein said cancer cell has acquired resistance to an anti-ErbB therapeutic, and wherein said cell comprises a MET activating mutation or a MET gene amplification, comprising the step of contacting the cell with an anti-MET therapeutic and an anti-ErbB therapeutic.

In another aspect, the invention provides a method for reducing ErbB-mediated signaling in a cancer cell, wherein said cancer cell has acquired resistance to an anti-ErbB therapeutic, and wherein said cell comprises a MET activating mutation or a MET gene amplification, comprising contacting the cell with an anti-MET therapeutic and an anti-ErbB therapeutic.

In another aspect, the invention provides a method for restoring sensitivity of a cancer cell to an anti-ErbB therapeutic, wherein said cancer cell has acquired resistance to an anti-ErbB therapeutic, and wherein said cell comprises a MET activating mutation or a MET gene amplification, comprising contacting the cell with an anti-MET therapeutic and an anti-ErbB therapeutic.

In another aspect, the invention provides a method for reducing growth or proliferation of a cancer cell, wherein said cancer cell has acquired resistance to an anti-ErbB therapeutic, and wherein said cell comprises a MET activating mutation or a MET gene amplification, comprising the step of contacting the cell with an anti-MET therapeutic and an anti-ErbB therapeutic.

In another aspect, the invention provides a method for increasing apoptosis of a cancer cell, wherein said cancer cell has acquired resistance to an anti-ERbB therapeutic, and wherein said cell comprises a MET activating mutation or a MET gene amplification, comprising the step of contacting the cell with an anti-MET therapeutic and an anti-ErbB therapeutic.

In another aspect, the invention provides a method for reducing resistance of a cancer cell to an anti-ErbB therapeutic, wherein said cancer cell has acquired resistance to an anti-ErbB therapeutic, and wherein said cell comprises a MET activating mutation or a MET gene amplification, comprising the step of contacting the cell with an anti-MET therapeutic and an anti-ErbB therapeutic.

In another aspect, the invention provides a method for treating acquired anti-ErbB therapeutic resistance in a cancer cell, wherein said cell comprises a MET activating mutation or a MET gene amplification, comprising contacting the cell with an anti-MET therapeutic and an anti-ErbB therapeutic.

In certain embodiments, the cancer cell is a mammalian cancer cell, such as, for example, a human cancer cell. The cancer cell may be a cell line or from a primary tissue sample. In certain embodiments, the cancer cell may be a lung cancer cell, a brain cancer cell, a breast cancer cell, a head and neck cancer cell, a colon cancer cell, an ovarian cancer cell, a gastric cancer cell or a pancreatic cancer cell. In certain embodiments, the cancer cell may be any ErbB-driven cancer. In certain embodiments, the cancer cell's growth and/or survival is promoted by ErbB. In certain embodiments, the cancer cell may comprise an ErbB activating mutation, such as, for example, an EGFR activating mutation. In certain embodiments, the cancer cell may comprise an ErbB gene amplification, such as, for example, an EGFR gene amplification. In certain embodiments, the ErbB gene amplification and/or MET amplification are at least 2-fold.

In certain embodiments, the cancer cell comprises an ErbB gene mutation associated with increased resistance to an anti-ErbB therapeutic, such as, for example a T790M mutation of EGFR.

In certain embodiments, the anti-ErbB therapeutic is selected from the group consisting of: an anti-EGFR therapeutic, an anti-ErbB2 therapeutic, an anti-ErbB3 therapeutic, or an anti-ErbB4 therapeutic. The anti-ErbB therapeutic may be a small molecule therapeutic, a nucleic acid therapeutic, or a protein therapeutic. In certain embodiments, the anti-ErbB therapeutic is an antibody, an antisense molecule, or a small molecule kinase inhibitor. In an exemplary embodiment, the anti-ErbB therapeutic is an EGFR kinase inhibitor selected from the group consisting of: gefitinib, erlotinib, lapatinib, PF00299804, CI-1033, EKB-569, BIBW2992, ZD6474, AV-412, EXEL-7647, HKI-272, cetuximab, pantinumumab, or trastuzumab. In an exemplary embodiment, an anti-ErbB protein therapeutic is an anti-EGFR antibody selected from the group consisting of: cetuximab, panitumumab, and trastuzumab. In an exemplary embodiment, an anti-ErbB nucleic acid therapeutic is an siRNA molecule.

In certain embodiments, the anti-MET therapeutic is a small molecule therapeutic, a nucleic acid therapeutic, or a protein therapeutic. In an exemplary embodiment, the anti-MET therapeutic is an antibody directed against MET or antibody directed against hepatocyte growth factor (HGF). In an exemplary embodiment, the anti-MET therapeutic is PHA-665,752, SU11274, SU5416, PF-02341066, XL-880, MGCD265, XL184, ARQ 197, MP-470, SGX-523, JNJ38877605, AMG 102, or OA-5D5. In an exemplary embodiment, the anti-MET therapeutic is an siRNA molecule.

In certain embodiments, contacting the cell with an anti-MET therapeutic and an ErbB therapeutic is part of a therapeutic regimen that comprises at least one additional treatment modality, such as, for example, at least one additional treatment modality is selected from the group consisting of: contacting said cell with one or more additional therapeutic agents, radiation, photodynamic therapy, laser therapy, and surgery.

In another aspect, the invention provides a method for identifying a subject as a candidate for treatment with an anti-ErbB therapeutic and an anti-MET therapeutic, wherein said subject has been treated with an anti-ErbB therapeutic and suffers from cancer that has acquired resistance to said anti-ErbB therapeutic, comprising detecting a MET activating mutation or MET gene amplification in a cancer cell from said subject.

In another aspect, the invention provides a method for identifying an anti-MET therapeutic comprising contacting a cancer cell that has acquired resistance to an anti-ErbB therapeutic, wherein said cancer cell comprises a MET activating mutation or a MET gene amplification, with an anti-ErbB therapeutic and a test compound and detecting a change in a cellular process selected from the group consisting of: decreased ErbB phosphorylation, decreased MET phosphorylation, decreased ErbB-MET association, decreased EGFR phosphorylation, decreased AKT phosphorylation, decreased cell growth, decreased cell proliferation and increased apoptosis, compared to said cellular process in an identical cell contacted only with an anti-ErbB therapeutic.

In another aspect, the invention provides a method for identifying a subject who is being treated with an anti-ErbB therapeutic and who is at risk for acquiring resistance to said anti-ErbB therapeutic, comprising detecting the presence of a MET activating mutation or a MET gene amplification in a cancer cell from said subject, wherein the presence of said MET activating mutation or MET gene amplification indicates a risk for acquiring said resistance.

In another aspect, the invention provides a method for producing a cell with acquired resistance to an anti-ErbB therapeutic comprising contacting a cell that is sensitive to an anti-ErbB therapeutic with at least one anti-ErbB therapeutic for at least 4 weeks and identifying cells that acquire resistance to said anti-ErbB therapeutic. In certain embodiments, the cell does not comprise a mutation in an ErbB gene that confers resistance to said anti-ErbB therapeutic.

In another aspect, the invention provides a cell produced by the methods provided herein. For example, a cell that has acquired resistance to an anti-ErbB therapeutic is provided.

In another aspect, the application provides a method for treating a subject suffering from a cancer that is resistant to treatment with an anti-ErbB therapeutic, comprising administering to the subject an anti-ErbB therapeutic and an agent that inhibits HGF mediated activation of MET. The agent that inhibits HGF mediated activation of MET may be, for example, an antibody that prevents HGF from binding to MET, such as an anti-HGF antibody or an anti-MET antibody.

In another aspect, the disclosure provides a cell or cell line comprising a deletion in exon 19 of EGFR and a MET gene amplification. In certain embodiments, the cell or cell line is a mammalian cell or cell line, such as, for example, a human cell or cell line. In certain embodiments, the cell or cell line is epithelial cell or cell line. In certain embodiments, the cell or cell line is an adenocarcinoma cell or cell line, such as, for example, a lung adenocarcinoma cell line. In certain embodiments, the deletion in exon 19 is a deletion of residues E746-A750 of human EGFR. In certain embodiments, the MET gene is amplified at least 3-fold, at least 5-fold, at least 10-fold, at least 20-fold, or from 3-10 fold, from 3-5 fold, or from 5-10 fold. In certain embodiments, the level of MET protein expression is elevated at least 2-fold, at least 3-fold, at least 5-fold, at least 10-fold, or from 3-10 fold, from 3-5 fold or from 5-10 fold as compared to the level of MET protein expression in a cell not having the MET gene amplification. In certain embodiments, the cell or cell line does not comprise a T790M mutation in the EGFR gene. In certain embodiments, the cell or cell line is resistant to at least one TKI, such as for example, an EGFR inhibitor. In certain embodiments, the cell or cell line is resistant to CL-387,785 and/or gefitinib.

BRIEF DESCRIPTION OF THE FIGURES

The foregoing and other features and advantages of the present invention will be more fully understood from the following detailed description of illustrative embodiments taken in conjunction with the accompanying drawings in which:

FIG. 1 HCC827 GR cells are resistant to gefitinib in vitro and contain an amplification of MET. A. HCC827 cell line, which harbors an EGFR (del E746_A750) mutation and is sensitive to gefitinib (IC50—4 nM), was made resistant to gefitinib by growing it in increasing concentrations of gefitinib. Both HCC827 parental cell line and two of the gefitinib-resistant clones, HCC827 GR5 and HCC827 GR6, were subjected to MTS survival assays in increasing concentrations of gefitinib. B. Gefitinib resistant HCC827 GR5 cells maintain ERBB3 and Akt phosphorylation in the presence of gefitinib. HCC827 and HCC827 GR5 cells were exposed to increasing amounts of gefitinib for 6 hours. Cells were lysed and probed with the indicated antibodies. The HCC827 GR5 maintain phosphorylation of ERBB3 and Akt (and to a lesser extent EGFR) even in the presence of 10 µM gefitinib. C. HCC827 GR5 cells maintain phosphorylation of ERBB3 and MET in the presence of gefitinib. Lysates from untreated and 1 µM gefitinib treated HCC827 and HCC827 GR5 cells were hybridized to a phospho-receptor tyrosine kinase (RTK) array (R&D systems) containing antibodies to 42 different phospho RTKs. Untreated HCC827 and HCC827 GR5 cells contain significant quantities of p-EGFR, p-ERBB2, p-ERBB3 and p-MET. Following gefitinib treatment (right sided panels) in HCC827 cells only some residual p-EGFR is present. D. HCC827 GR cells contain a focal amplification in chromosome 7. Genome wide view of copy number changes were generated using Human Mapping 250K Sty single nucleotide polymorphism (SNP) array (Affymetrix, Inc.) and analyzed using the dChip program as previously described. The GR clones are compared to the parental HCC827 cell line. The red vertical line on the right side is set relative to the parental cell line. As can be seen there is a focal amplification on the long arm of chromosome 7. E. The amplification in HCC827 GR cells encompasses MET but not it's known ligand HGF or EGFR. Expanded view of data from FIG. 1D. The focal amplification on chromosome 7 ranges from 7g31.1 to 7g33.3 and contains MET but not HGF or EGFR.

FIG. 2. Concurrent inhibition of MET and EGFR suppresses growth of HCC827 GR cells and leads to downregulation of ERBB3/PI3K/AKT signaling. A. The HCC827 GR5 cells were treated with increasing concentrations of either gefitinib or PHA-665752 alone or in combination and subjected to an MTS survival assay (methods). The cells are significantly growth inhibited only when exposed to gefitinib and PHA665752 in combination. B. Western blot analyses of HCC827 and HCC827 GR6, GR7 and GR8 cell lines treated with either gefitinib, PHA-665752 or with both drugs. Cells were treated for 6 hours following either 1 µM gefitinib or 1 µM PHA-665752 alone or in combination. Cells were lysed and probed with the indicated antibodies. Unlike in the parental HCC827 cell line, p-ERBB3 and p-Akt are maintained in the presence of gefitinib. Inhibition of MET alone in the parental or resistant cell lines has no significant effect on p-ERBB3 or p-AKT. However, in combination with gefitinib, there is significant inhibition of p-ERBB3, p-AKT and p-ERK 1/2. C. The combination of gefitinib and PHA-665752 abrogates the association of p85 with ErbB-3 in HCC827 GR6, GR7 and GR8 cells. HCC827 and HCC827 GR cells were exposed to 1 μM gefitinib or 1 μM PHA-665752 alone or in combination for 6 hours prior to lysis. Lysates were immunoprecipitated with anti-p85 antibodies and the immunoprecipitates were probed with anti-phospho-tyrosine, anti-ERBB-3, anti-Gab1 and anti-p85 antibodies. In the parental HCC827 cell line, ERBB3 association with p85 is abrogated by gefitinib but this interaction is maintained in the HCC827 GR cells even in the presence of gefitinib. While Gab1 association with p85 is disrupted in HCC827 GR cells with PHA-665752 alone, only the combination of gefitinib and PHA-665752 dissociates ERBB3 from p85 in these cell lines. D. Lentiviral constructs containing a control shRNA or shRNA directed against two different regions of MET were infected (methods) into HCC827 GR6 cells and growth in the presence of gefitinib was examined by an MTS assay. HCC827 GR6 cells containing shRNAs to MET regain their sensitivity to gefitinib while those infected with a control shRNA remain resistant. E. Gefitinib down-regulates ERBB3/PI3K/AKT signaling in HCC827 GR6 cells infected with a MET shRNA. HCC827 GR6 cells infected with a control shRNA or shRNAs directed at MET were treated with 1 μM gefitinib for 6 hours. Cells were lysed and probed with the indicated antibodies. In HCC827 GR6 infected with a control shRNA gefitinib treatment does not effect p-ERBB3 or p-AKT. In contrast downregulation of MET now restores gefitinib's ability to downregulate p-ERBB3 and p-AKT in the HCC827 GR 6 cells.

FIG. 4. Fluorescence in situ hybridization (FISH) analyses of xenografts and NSCLC patients. Dual color FISH (CEP7 (green), 1D7S522 (red)) was performed on paraffin sections from HCC827 and the HCC875 GR5 xenografts and on pre and post-gefitinib treated tumor specimens from patient 8 (FIG. 5). In HCC827 GR5 and the post-gefitinib treated tumor specimens there is evidence of MET amplification. Magnification is 1000× in these images.

FIG. 5. Summary of genetic changes in NSCLC patients with acquired resistance to gefitinib or erlotinib. Eighteen NSCLC patients with EGFR mutations with either paired pre- and post-treatment specimens (n=8) or post-treatment specimens only (n=10) were analyzed for EGFR mutations, presence of EGFR T790M and MET amplification by either quantitative PCR or FISH. The results column indicates MET copy number (standard deviation) in patients analyzed by QPCR and percent of cells with >3 additional copies of the MET locus compared to CEP 7 in those analyzed by FISH. Tumor specimens with MET amplification are marked by an asterisk. Four of 18 patients (22%) have evidence of MET amplification in their post-treatment tumor specimens, and in ¼ this occurs in a specimen with a concurrent EGFR T790M mutation.

FIG. 6. Shows a plot MET copy number determined by Quantitative PCR for HCC827 resistant cells and the parental cell line. The results show that MET was amplified 5-10 fold in all the HCC827 resistant cell lines as compared to the parental HCC827 cell line.

FIG. 8. Shown are the top 20 genes that are differentially over expressed in the HCC82-7 GR clones compared to the parental HCC827 cell line. Also shown are the chromosomal locations of the genes and the mean (of the 6 HCC827 GR clones) fold change in expression level.

FIG. 9. Breakdown of patient specimens analyzed by FISH. In each sample 100 cells were counted and the percent of cells containing more than 2 or 3 additional copies of MET compared to CEP 7 are shown.

DETAILED DESCRIPTION

1. Definitions

Figure 3A:
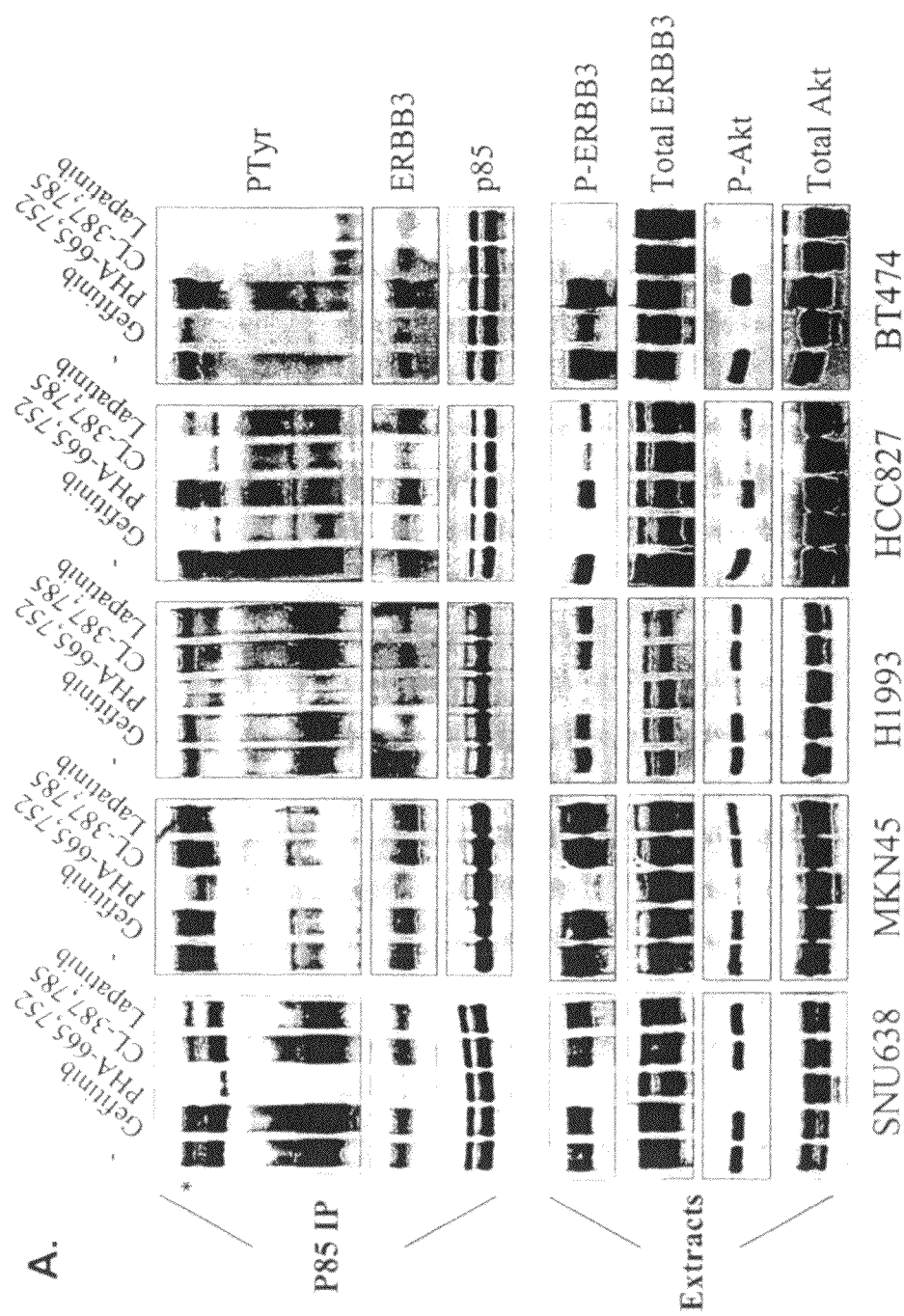
FIG. 3. MET activates ERBB3 in other MET amplified cell lines. A. MET amplified cell lines use ERBB3 to activate PI3KIAKT signaling. MET amplified gastric cancer (SNU-638 and MKN-45) and NSCLC (H1993) cells, EGFR mutant NSCLC (HCC827) and ERBB2 amplified breast cancer cells (BT474) were treated with either gefitinib (1 mM), PHA-665, 752 (1 μM), lapatinib (1 μM) or CL-387,785 (1 μM) for 6 hours prior to lysis. Lysates were immunoprecipitated with anti-p85 antibodies and the immunoprecipitates were probed with anti-phospho-tyrosine, anti-ERBB-3 and anti-p85 antibodies (* indicates ERBB3 on the PTyr blot). In parallel, the lysates were analyzed by Western blotting and probed with the indicated antibodies. As can be seen in the MET amplified cells, only PHA-665,752 leads to disruption of ERBB3 association with p85, and downregulation of ERBB3 and Akt phosphorylation. As controls, the EGFR mutant HCC827 cells and the ERBB2 amplified BT474 cells demonstrate decreased association between p85 and ERBB3 and downregulation of p-ERBB3 and p-AKT in the presence of EGFR and ERBB2 inhibitors respectively. PHA-665,752 has no effect on PI3K signaling in either of these cell lines. B. ERBB3 knockdown leads to dowregulation of p-AKT in SNU-638 cells. Lentiviral shRNA constructs containing a scrambled (SC) sequence, ERBB3 specific sequence, a control sequence (CTRL) or GFP were infected into SNU638 cells (Methods). Seventy-two hours following infection, the cells were lysed and probed with indicated antibodies. The ERBB3 specific shRNA leads to downregulation of p-Akt. C. ERBB3 shRNA inhibits growth of SNU-638 cells. Growth of SNU-638 cells was assayed by an MTS assay 5 days following infection of shRNA constructs in B. Growth is normalized to the SC shRNA. Infection of the ERBB3 shRNA leads to significant growth inhibition of SNU-638 cells. D. MET activates ERBB3 in CHO cells. CHO cells were transfected with either GFP, ERBB3 cDNA alone or in combination with a MET cDNA. The cells were treated with either PHA-665,752 (1 PM), gefitinib (3 μM), lapatinib (3 μM) or PP2 (10 μM) for 6 hours, the treated cells lysed and probed with p-ERBB3 and ERBB3. As can be seen, ERBB3 is phosphorylated only in the presence of MET which is inhibited by PHA-665,752 but not gefitinib, lapatinib or PP2. E. ERBB3 co-precipitates with p85 in the presence of MET and is inhibited by PHA-665,752. Immunoprecipitation was performed using ERBB3 from CHO cells transfected with either GFP, ERBB3 or MET and ERBB3 in the presence or absence of PHA-665,752 (1 μM), gefitinib (3 μM) or lapatinib (3 μM). The resulting proteins were lysed and probed with the indicated antibodies. As can be seen p85 co-precipitates with ERBB3 only in the presence of MET which is inhibited by PHA-665,752 but not by gefitinib or lapatinib. F. MET and ERBB3 co-precipitate from CHO cells. Immunoprecipitation using MET was performed using CHO cells transfected with either GFP, MET alone, ERBB3 alone or MET and ERBB3 with or without PHA-665, 752 (1 μM) treatment. The resulting lysates were probed with either ERBB3 or MET. As can be seen, MET only immunoprecipitates ERBB3 from CHO cells transfected with both construct.

As used herein, the following terms and phrases shall have the meanings set forth below. Unless defined otherwise, all technical and scientific terms used herein have the same meaning as commonly understood to one of ordinary skill in the art.

The term "such as" is used herein to mean, and is used interchangeably, with the phrase "such as but not limited to".

The singular forms "a," "an," and "the" include plural reference unless the context clearly dictates otherwise.

The term "cancer" as used herein refers to all neoplastic cell growth and proliferation, whether malignant or benign, to all pre-cancerous and cancerous cells and tissues, and to all metastases. There are two general types of cancers: benign and malignant. Nearly all benign cancers are encapsulated and are noninvasive; in contrast, malignant cancers are almost never encapsulated and invade adjacent tissue by infiltrative destructive growth. This infiltrative growth can be followed by cancer cells implanting at sites that are discontinuous with the original cancer. Cancers that migrate from their original location and seed vital organs (thereby giving rise to metastatic lesions) can eventually lead to the death of the subject through the functional deterioration of the affected organs. A metastasis is a region of cancer cells, distinct from the primary cancer location resulting from the dissemination of cancer cells from the primary cancer to other parts of the body.

The terms "comprise" and "comprising" are used in the inclusive, open sense, meaning that additional elements may be included.

The term "including" is used to mean "including but not limited to". "Including" and "including but not limited to" are used interchangeably.

A "patient" or "subject" refers to a mammal as is known in the art. Exemplary mammals include humans, primates, livestock animals (including bovines, porcines, etc.), companion animals (e.g., canines, felines, etc.) and rodents (e.g., mice and rats).

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

2. Methods for Treating EGFR TKI Resistant Cancer

Provided herein are methods for treating cancer, prolonging the life expectancy of a subject afflicted with cancer, or reducing one or more symptoms associated with a cancer, using a combination of an anti-ErbB therapeutic and an anti-MET therapeutic. Any anti-ErbB therapeutic may be used in accordance with the methods described herein including for example, an anti-ErbB1 therapeutic (ErbB1/EGFR/HER1), an anti-ErbB2 therapeutic (ErbB2/Neu/Her2), an anti-ERB3 therapeutic (ErbB3/Her3), or an anti-ErbB4 therapeutic (ErbB4/Her4). In certain embodiments, the methods described herein may be used to treat subjects suffering from cancers associated with elevated ErbB activity and/or expression levels (such as, for example, an ErbB activating mutation, an ErbB gene amplification, or ligand mediated ErbB activation) and elevated MET activity and/or expression levies (such as, for example, a MET activating mutation, a MET gene amplification, or HGF mediated MET activation). HGF mediated MET activation may be associated with elevated levels of HGF activity and/or expression levels (such as, for example, an HGF activating mutation or an HGF gene amplification).

In exemplary embodiments, the methods described herein may be used to treat one or more of the following types of cancer: ovarian, pancreatic, lung, brain, breast, head and neck, colon, gastric, pancreatic, rectal, kidney, liver, bladder, prostate, gastric, thyroid, pituitary, adrenal or glioblastoma cancers. In an exemplary embodiment, the methods may be used to treat lung cancer, such as, for example, non-small cell lung cancer (NSCLC).

Examples of ErbB activating mutations that may be associated with cancer include, for example, point mutations, deletion mutations, insertion mutations, inversions or gene amplifications that lead to an increase in at least one biological activity of an ErbB protein. Exemplary biological activities include, for example, tyrosine kinase activity (for ErbB1, ErbB2, or ErbB4), formation of protein-protein interactions (such as, for example, receptor homo- or hetero-dimerization, ligand binding, binding to a substrate, etc.), or ErbB mediated signaling. Mutations can be located in any portion of an ErbB gene or regulatory region associated with an ErbB gene. Exemplary ErbB I (EGFR) mutations include, for example, mutations in exon 18, 19, 20 or 21, mutations in the kinase domain, G719A, L858R, E746K, L747S, E749Q, A750P, A755V, V765M, 57681, L858P, E746-R748 del, R748-P753 del, M766-A767 A1 ins, S768-V769 SVA ins, P772-H773 NS ins, 2402G>C, 2482G>A, 2486T>C, 2491G>C, 2494G>C, 2510C>T, 2539G>A, 2549G>T, 2563C>T, 28197>C, 2482-2490 del, 2486-2503 del, 2544-2545 ins GCCATA, 2554-2555 ins CCAGCGTGG, or 2562-2563 ins AACTCC. Other examples of ErbB1 activating mutations are known in the art (see e.g., US Patent Publication No. 2005/0272083). Exemplary ErbB2 mutations include, for example, mutations in the kinase domain, or exon 20 insertions such as, for example, G776insV_G/C and A775insYVMA. Exemplary ErbB3 and ErbB4 mutations may include, for example, mutations in the kinase domain. The nucleotide and amino acid sequences for a variety of ErbB sequences, including human ErbB1, human ErbB2, human ErbB3 and human ErbB4, are publicly available and may be found, for example, on the world wide web at ncbi.nlm.nih.gov. For example, nucleotide and amino acid sequences for human ErbB1 (EGFR) may be found in GenBank Accession Nos. NM_005228 and NP_005219, respectively; nucleotide and amino acid sequences for human ErbB2 may be found in GenBank Accession Nos. NM_004448 and NP_004439, respectively; nucleotide and amino acid sequences for human ErbB3 may be found in GenBank Accession Nos. NM_001982 and NP_001973, respectively; and nucleotide and amino acid sequences for human ErbB4 may be found in GenBank Accession Nos.

NM_005235 and NP_005226, respectively. Information about ErbB receptors including receptor homo- and heterodimers, receptor ligands, autophosphorylation sites, and signaling molecules involved in ErbB mediated signaling is known in the art (see e.g., Hynes and Lane, Nature Reviews Cancer 5: 341-354 (2005)).

In other embodiments, ErbB activating mutations may be mutations outside of the ErbB sequence itself that lead to an increase in at least one biological activity of an ErbB protein. For example, a mutation leading to overexpression of an ErbB ligand may lead to an increase in ErbB activity and therefore would be considered an ErbB activating mutation. Similarly, a mutation leading to overexpression of a transcription factor that is involved in ErbB expression could lead to an overexpression of an ErbB protein and an increase in ErbB activity and therefore would also be considered an ErbB activating mutation. Such examples are merely illustrative and a variety of other ErbB activating mutations may be contemplated by one of skill in the art based on the disclosure provided herein.

In exemplary embodiments, the methods described herein may be used to treat cancers that have acquired resistance to treatment with one or more anti-ErbB therapies, including an anti-ErbB1 therapy, an anti-ErbB2 therapy, an anti-ErbB3 therapy, and/or an anti-ErbB4 therapy. Various anti-ErbB therapeutics are known in the art and include for example, small molecule therapeutics, protein therapeutics, or nucleic acid therapeutics. Further examples of anti-ErbB therapeutics are provided herein below. In certain embodiments, the methods described herein may be used to treat cancer that is resistant to treatment with an ErbB kinase inhibitor. In certain embodiments, the methods described herein may be used to treat cancer that is resistant to treatment with an ErbB1 (EGFR) kinase inhibitor. In an exemplary embodiment, the methods described herein may be used to treat cancer that is resistant to treatment with gefitinib, erlotinib or both.

Various qualitative and/or quantitative methods may be used to determine if a subject has developed or is susceptible to developing a resistance to treatment with an anti-ErbB therapeutic. For example, a subject who showed initial improvement while taking an anti-ErbB therapeutic, may display signs that the anti-ErbB therapeutic has become less effective or is no longer effective. Exemplary indicators of an effective anti-ErbB therapeutic that may decline or abate in association with resistance include, for example, improved well-being of the patient, decrease or shrinkage of the size of a tumor, arrested or slowed growth of a tumor, and/or absence of metastasis of cancer cells to other locations in the body. Symptoms that may be associated with resistance to an anti-ErbB therapeutic include, for example, a decline or plateau of the well-being of the patient, an increase in the size of a tumor, arrested or slowed decline in growth of a tumor, and/or the spread of cancerous cells in the body from one location to other organs, tissues or cells.

Various symptoms associated with cancer may also be used to identify subjects that have developed or are susceptible to developing a resistance to an anti-ErbB therapy. In particular, such symptoms may develop, worsen or become reestablished in a subject who is being treated with an anti-ErbB therapy. Exemplary symptoms include, for example, anorexia, cognitive dysfunction, depression, dyspnea, fatigue, hormonal disturbances, neutropenia, pain, peripheral neuropathy, and sexual dysfunction. The symptoms associated with cancer may vary according to the type of cancer. For example, symptoms associated with cervical cancer include, for example, abnormal bleeding, unusual heavy vaginal discharge, pelvic pain that is not related to the normal menstrual cycle, bladder pain or pain during urination, and bleeding between regular menstrual periods, after sexual intercourse, douching, or pelvic exam. Symptoms associated with lung cancer, may include, for example, persistent cough, coughing up blood, shortness of breath, wheezing chest pain, loss of appetite, losing weight without trying and fatigue. Symptoms for liver cancer may include, for example, loss of appetite and weight, abdominal pain, especially in the upper right part of your abdomen, that may extend into the back and shoulder, nausea and vomiting, general weakness and fatigue, an enlarged liver, abdominal swelling (ascites), and a yellow discoloration of the skin and the whites of eyes (jaundice). One skilled in oncology may readily identify symptoms associated with a particular cancer type.

Others means to determine if a subject has developed a resistance to an anti-ErbB therapeutic include, for example, examining one or more of the following: ErbB1, ErbB2, ErbB3, or ErbB4 phosphorylation, phosphatidyl inositol 3'-kinase (PI3K) mediated signaling, ErbB1, ErbB2, ErbB3, or ErbB4 mediated signaling, sensitivity of cancer cells to an anti-ErbB therapeutic, growth or proliferation of cancer cells, or cancer cell apoptosis, etc. For example, an increase in ErbB phosphorylation, PI3K mediated signaling, and/or ErbB mediated signaling, as compared to a control, may be indicative that the subject has developed or is susceptible to developing a resistance to an anti-ErbB therapeutic. Methods for determining ErbB phosphorylation, PI3K mediated signaling and ErbB mediated signaling may be determined using known techniques and are described further herein.

Additionally, a decrease in the sensitivity of cancer cells to an anti-ErbB therapeutic, an increase in the growth or proliferation of cancer cells, and/or a decrease in cancer cell apoptosis as compared to a control, may also be indicative that the subject has developed or is susceptible to developing a resistance to anti-ErbB therapeutic. It is possible to determine cancer cell sensitivity, growth, proliferation or apoptosis using standard methods as described further herein. For example, cancer cell sensitivity, growth, proliferation or apoptosis may be determined either in situ or in vitro. In situ measurements may involve, for example, observing the effect of an anti-ErbB therapy in a subject by examining cancer growth or metastasis. Alternatively, a sample of cancer cells from the subject may be removed and tested in vitro, for example, to determine the sensitivity, growth, proliferation or apoptosis of the cells from the subject. The in vitro analysis may involve analysis of cells that were treated in situ with the anti-ErbB therapeutic and then removed from the subject for analysis in vitro or may involve contacting the cancer cells in vitro with the anti-ErbB therapy. Suitable methods for examining cancer cell growth, proliferation and apoptosis are described further below.

In various embodiments, it may be desirable to compare one or more measurements of resistance to an anti-ErbB therapeutic to a control. Exemplary controls include, for example, well being, tumor size, tumor growth, or presence or rate of metastasis in the same subject prior to treatment, the same subject at an earlier time point during treatment, or a different subject receiving the same anti-ErbB therapy that may or may not be resistant to the therapy. Other types of suitable controls include, for example, sensitivity to an anti-ErbB therapeutic, growth, proliferation or apoptosis of cells from the same subject at an earlier point during treatment with an anti-ErbB therapeutic, from the same subject prior to treatment with anti-ErbB therapeutic, a control subject who is responsive to treatment with an anti-ErbB therapeutic, a cell line with known anti-ErbB responsiveness, a control subject who is resistant to treatment with an anti-ErbB therapeutic, or a reference value for a given measurement. Such controls may be in situ measurements or in vitro measurements similar to those described above for a given subject. In various embodiments, controls may involve utilization of cells from the same tissue from the same subject prior to treatment, cells from the same tissue from the same subject earlier during treatment, nontumorigenic cells from the same subject, nontumorigenic cells from other subjects, nontumorigenic cells from a population or subjects, or an established cell line. Controls may also be a reference value or table in hardcopy or in a database that may be derived from one or more individuals optionally in association with relevant information such as, for example, gender, cancer status, presence of any metastasis, any type of treatment administered, presence or absence of an activating mutation or gene amplification in an ErbB gene, presence or absence of an activating mutation or gene amplification in the MET gene, levels of ErbB phosphorylation, levels of PI3K signaling, etc.

In yet other embodiments, identification of a subject who has developed a resistance to an anti-ErbB therapeutic may involve detection of elevated MET expression levels or elevated MET activity, for example, arising from an activating mutation of the MET gene or a MET gene amplification. Activating mutations of the MET gene may be any kind of mutation including, for example, point mutations, deletion mutations, insertion mutations, inversions or gene amplifications that lead to an increase in at least one biological activity of a MET protein. Exemplary biological activities include, for example, tyrosine kinase activity, formation of protein-protein interactions (such as, for example, receptor homo- or hetero-dimerization, ligand binding, binding to a substrate, etc.), and MET mediated signaling. Mutations can be located in any portion of the MET gene or regulatory regions associated with the gene. Exemplary mutations include, for example, mutations in the kinase domain of MET or mutations that result in an amino acid change at any one or more of the following positions: N375, I638, V13, V923, I316 and E168, relative to wild type MET. Methods for detecting MET mutations or gene amplifications involve art recognized techniques which are described further herein. In other embodiments, MET activating mutations may be mutations outside of the MET sequence itself that lead to an increase in at least one biological activity of a MET protein. For example, a mutation leading to overexpression of a MET ligand may lead to an increase in MET activity and therefore would be considered a MET activating mutation. Similarly, a mutation leading to overexpression of a transcription factor that is involved in MET expression could lead to an overexpression of MET and an increase in MET activity and therefore would also be considered a MET activating mutation. Such examples are merely illustrative a variety of other MET activating mutations may be contemplated by one of skill in the art based on the disclosure provided herein.

In certain embodiments, elevated levels of MET activity may be associated with HGF mediated MET activation. HGF mediated MET activation may be associated with, for example, an HGF activating mutation or an HGF gene amplification. Methods for detecting HGF mediated MET activation, HGF activating mutations or HGF gene amplifications involve art recognized techniques which are described further herein.

In exemplary embodiments, combinations of the above methods may be used to identify subjects who have developed or are susceptible to developing a resistance to an anti-ErbB therapy. For example, during the course of treatment with anti-ErbB therapeutic, the well being of the subject, tumor size, and/or metastasis of the cancer may be monitored by the medical practitioner. If the subject begins to exhibit symptoms indicating the anti-ErbB therapy is declining in effectiveness, a secondary screen may be used to identify those subjects that are becoming resistant to the anti-ErbB therapy. For example, the subjects may be screened to examine ErbB phosphorylation, PI3K mediated signaling, ErbB mediated signaling, sensitivity of cancer cells to an anti-ErbB therapeutic, growth or proliferation of cancer cells, cancer cell apoptosis, and/or the presence of elevated levels of MET activity or expression, such as, for example, an activating mutation in the MET gene, a MET gene amplification, or HGF mediated MET activation. In an exemplary embodiment, a subject receiving an anti-ErbB therapy is monitored during the course of treatment for signs of resistance based on well being of the subject, tumor size, and/or metastasis of the cancer. Those subjects suspected of being at risk of resistance to the anti-ErbB therapy are then tested to identify whether the subject has an activating mutation in the MET gene, a MET gene amplification, or HGF mediated MET activation. In other embodiments, a subject may be monitored during the course of treatment with the anti-ErbB therapy for the presence of an activating mutation of the MET gene, a MET gene amplification, or HGF mediated MET activation regardless of the well being of the subject, tumor size, and/or metastasis of the cancer. In yet other embodiments, a subject receiving treatment with an anti-ErbB therapy may be monitored during treatment to determine sensitivity of cancer cells to an anti-ErbB therapeutic, growth or proliferation of cancer cells, and/or cancer cell apoptosis. Those subjects suspected of being at risk to resistance of the anti-ErbB therapeutic may then be tested for the presence of an activating mutation in the MET gene, a MET gene amplification, or HGF mediated MET activation. The above described combinations are merely illustrative and all other possible combinations are also contemplated herein and would be evident to one of skill in the art based on this disclosure.

In various embodiments, the subjects being monitored for resistance to an anti-ErbB therapeutic may be evaluated at one or more time points during the course of treatment with the anti-ErbB therapeutic. In exemplary embodiments, subjects may be monitored at regular intervals during the course of treatment. For example, subjects may be monitored at least once a day, once every other day, once a week, once every other week, once a month, during each doctors visit, in conjunction with administration of each anti-ErbB therapeutic dosing, etc. Monitoring may involve self-evaluation by the subject, evaluation by a medical practitioner, evaluation based on results from laboratory tests, and various combinations thereof.

Once a subject who has developed resistance to an anti-ErbB therapeutic, or is susceptible to developing such a resistance, and who has an activating mutation in the MET gene, a MET gene amplification, or HGF mediated MET activation has been identified, a combination of an anti-ErbB therapy and an anti-MET therapy is then administered to the patient. Exemplary anti-ErbB and anti-MET therapeutics are described further herein. In exemplary embodiments, the anti-ErbB therapeutic and the anti-MET therapeutic are each individually selected from one or more of the following: a small molecule therapeutic, a nucleic acid therapeutic, or a protein therapeutic. In an exemplary embodiment, the anti-ErbB therapeutic is an anti-EGFR therapeutic such as, for example, gefitinib, erlotinib, lapatinib, PF00299804, CI-1033, EKB-569, BIBW2992, ZD6474, AV-412, EXEL-7647, HKI-272, cetuximab, pantinumumab, or trastuzumab, or combinations thereof and the anti-MET therapeutic is PHA-665,752, SU11274, SU5416, PF-02341066, XL-880, MGCD265, XL184, ARQ 197, MP-470, SGX-523, JNJ38877605, AMG 102, or OA-5D5, or combinations thereof.

In certain embodiments, the anti-ErbB therapeutic that is administered as part of a combination with an anti-MET therapeutic is the same anti-ErbB therapeutic to which the subject has developed a resistance. For example, if a subject was being treated with erlotinib (an anti-ErbB1 therapeutic) and then develops a resistance to this therapeutic, the subject may then be treated with a combination of erlotinib and, for example, PHA-665752 (an anti-MET therapeutic) going forward. Alternatively, the anti-ErbB therapeutic may be different than the therapeutic to which the subject has developed a resistance. For example, if a subject was being treated with erlotinib and then develops a resistance to this therapeutic, the subject may then be treated with gefitinib (another anti-ErbB1 therapeutic) and, for example, PHA-665752 going forward. These combinations are merely illustrative and many other combinations are contemplated herein and would be evident to one of skill in the art based on this disclosure.

In certain embodiments, the methods described herein involve administration of a combination of an anti-ErbB therapeutic and an anti-MET therapeutic. Combination therapies comprising an anti-ErbB therapeutic and an anti-MET therapeutic may refer to (1) pharmaceutical compositions that comprise a coformulation of at least one anti-ErbB therapeutic and at least one anti-MET therapeutic; and (2) co-administration of one or more anti-ErbB therapeutic agents with one or more anti-MET therapeutic agents wherein the anti-ErbB therapeutic agents and anti-MET therapeutic agents have not been formulated in the same compositions (but may be present within the same kit or package, such as a blister pack or other multi-chamber package; connected, separately sealed containers (e.g., foil pouches) that can be separated by the user; or a kit where the therapeutic agents are in separate vessels). When using separate formulations, the therapeutic agents may be administered at the same time (simultaneously), intermittently, or staggered, and in various embodiments the anti-ErbB therapeutic may be administered prior to the anti-MET therapeutic agent or subsequent to the anti-MET therapeutic agent, or various combinations of the foregoing.

In various embodiments, the methods provided herein involve analysis of biological samples from subjects, for example, to identify activating mutations or gene amplification of an ErbB gene, the MET gene, and/or the HGF gene. Any suitable biological sample from a subject may be used in accordance with the methods including, for example, a body fluid sample, cell sample, or a tissue sample, taken from a subject. Suitable body fluids include, but are not limited to, pleural fluid samples, pulmonary or bronchial lavage fluid samples, synovial fluid samples, peritoneal fluid samples, bone marrow aspirate samples, lymph, cerebrospinal fluid, ascites fluid samples, amniotic fluid samples, sputum samples, bladder washes, semen, urine, saliva, tears, blood, and its components serum and plasma, and the like. In an exemplary embodiment, the biological sample is a sample comprising cancer cells from one or more locations in the subject. For example, biological samples obtained from a tumor biopsy or resection may be used. In certain embodiments, it may be desirable to test tumor samples from more than one location within a subject. If a subject has tumors at more than one location, it may be desirable to test for activating mutations or gene amplification of an ErbB gene, the MET gene, and/or the HGF gene at each of the tumor locations to determine if the tumors are associated with the same or different genetic modifications.

In certain embodiments, the anti-ErbB/anti-MET combination therapy can be used in conjunction with other treatments or therapeutic agents, such as, for example, other immunotherapies, such as antigens, adjuvants, immunomodulators, or passive immune therapy with antibodies. The anti-ErbB/anti-MET combination therapy also may be administered in conjunction with nondrug treatments, such as surgery, radiation therapy or chemotherapy. The other therapy may be administered before, concurrent with, or after treatment with the anti-ErbB/anti-MET combination therapy. There may also be a delay of several hours, days and in some instances weeks between the administration of the different treatments, such that the anti-ErbB/anti-MET combination therapy may be administered before or after the other treatment.

In one embodiment, the anti-ErbB/anti-MET combination therapy is administered in conjunction with (i.e., before, during or after) another anti-cancer therapy, and in particular another anti-cancer therapy that does not comprise the administration of an anti-ErbB therapeutic and/or an anti-MET therapeutic to the subject. For example, the anti-ErbB/anti-MET combination therapy may be administered together with any one or more of the chemotherapeutic drugs known to those of skill in the art of oncology, (Reference: Cancer, Principles & Practice of Oncology, DeVita, V. T., Hellman, S., Rosenberg, S. A., 6th edition, Lippincott-Raven, Philadelphia, 2001), such as, for example: abarelix, adriamycin, aldesleukin, altretamine, aminoglutethimide, amsacrine, anastrozole, antide, arimidex, asimicin, asparaginase, AZD2171 (Recentin™), Bacillus Calmette-Guerin/BCG (TheraCys™, TICE™), bevacizumab (Avastin™), bicalutamide, bleomycin, bortezomib (Velcade™), bullatacin, buserelin, busulfan, campothecin, capecitabine, carboplatin, carmustine, chlorambucil, chlorodeoxyadenosine cisplatin, cladribine, clodronate, colchicine, cyclophosphamide, cyproterone, cytarabine, dacarbazine, dactinomycin, dasatinib (Sprycel™), daunorubicin, dienestrol, diethylstilbestrol, discodermolide, dexamethasone, docetaxel (Taxotere™), doxorubicin, Abx-EGF, epothilones, epirubicin, estradiol, estramustine, etoposide, exemestane, floxuridine, 5-fluorouracil, filgrastim, flavopiridol, fludarabine, fludrocortisone, fluorouracil, fluoxymesterone, flutamide, fulvestrant, gemcitabine (Gemzar™), genistein, goserelin, guanacone, hydroxyurea, idarubicin, ifosfamide, imatinib mesylate (Gleevac™), interferon, interleukins, irinotecan, ibritumomab (Zevalin™), ironotecan, ixabepilone (BMS-247550), letrozole, leucovorin, leuprolide, levamisole, lomustine, mechlorethamine, medroxyprogesterone, megestrol, melphalan, mercaptopurine, mesna, methotrexate, mithramycin, mitomycin, mitotane, mitoxantrone, mitozolomide, nilutamide, nocodazole, octreotide, oxaliplatin, paclitaxel (Taxol™), pamidronate, pegaspargase, pentostatin, plicamycin, porfimer, prednisone, procarbazine, raltitrexed (Tomudex™), rapamycin, ramptothecin, rituximab (Rituxan™), rolliniastatin, sorafenib (Nexavar™/Bayer BAY43-9006), squamocin, squamotacin, streptozocin, suramin, sunitinib malate (Sutent™), tamoxifen, temsirolimus (CCl-779), temozolomide (Temodar™), teniposide, testosterone, thioguanine, thiotepa, titanocene dichloride, topotecan, toremifene, tositumomab (Bexxar™), trastuzumab, tretinoin, VEGF Trap, vinblastine, vincristine, vindesine, and vinorelbine, zoledronate.

The anti-ErbB/anti-MET combination therapy also may be used with nondrug treatments for cancer, such as with surgical procedures to remove the cancer mass, chemotherapy or radiation therapy. The nondrug therapy may be administered before, concurrent with, or after treatment with the anti-ErbB/ anti-MET combination therapy. There may also be a delay of several hours, days and in some instances weeks between the administration of the different treatments, such that the agents of the invention may be administered before or after the other treatment.

In one embodiment, the anti-ErbB/anti-MET combination therapy is administered during a surgical procedure, such as, for example, during the removal of a tumor or a tumor biopsy. Surgical methods for treating cancer include intra-abdominal surgeries such as right or left hemicolectomy, sigmoid, subtotal or total colectomy and gastrectomy, radical or partial mastectomy, prostatectomy and hysterectomy. In one embodiment, the anti-ErbB/anti-MET combination therapy may be administered locally to an area of cancerous mass after or during surgical removal of a tumor.

In addition, the anti-ErbB/anti-MET combination therapy can be administered together with any form of radiation therapy including external beam radiation, intensity modulated radiation therapy (IMRT), and any form of radiosurgery including, for example, Gamma Knife, Cyberknife, Linac, and interstitial radiation (such as, for example, implanted radioactive seeds or GliaSite balloon).

In another aspect, the invention provides a method for reducing ErbB phosphorylation in a cancer cell by contacting the cell with an anti-ErbB therapeutic and an anti-MET therapeutic. In exemplary embodiments, the cancer cell has acquired a resistance to an anti-ErbB therapeutic and comprises elevated levels of MET activity and/or expression, e.g., associated with, for example, an activating mutation in the MET gene, a MET gene amplification, or HGF mediated MET activation. The methods disclosed herein may be used to reduce the phosphorylation of one or more of ErbB1, ErbB2, ErbB3 and/or ErbB4. Methods for examining ErbB phosphorylation are known in the art. For example, an anti-phospho-ErbB antibody may be used to determine the presence and/or amount of phosphorylated ErbB in a cell (e.g., immunohistochemical techniques) or in a cell lysate. Alternatively, a cell lysate may be run on an SDS-PAGE gel, blotted to nitrocellulose and then probed with an anti-ErbB antibody to detect the presence and/or amount of one or more phosphorylated ErbB proteins in the cell. Additionally, an anti-ErbB (e.g., ErbB1, ErbB2, or ErbB4) antibody may be used to immunoprecipitate an ErbB protein from a cell lysate, and the ErbB protein may then be used in a kinase assay to detect the presence of active, phosphorylated ErbB protein in the cell. Suitable kinase assays for ErbB proteins are well known in the art, as are methods for measuring phosphorylation of a protein substrate. In yet another embodiment, the presence and/or amount of an anti-ErbB protein may be determined using a phospho-receptor tyrosine kinase (RTK) array (commercially available from R&D systems). Antibodies specific for ErbB1, phospho-ErbB1, EbB2, phospho-ErbB2, ErbB3, phospho-ErbB3, ErbB4 and phospho-ErbB4 are commercially available (see e.g., Cell Signaling Technology, Danvers, Mass.). In certain embodiments, it may be desirable to compare the level of ErbB phosphorylation in the cancer cell to a control, e.g., a cell that has not been contacted with an anti-ErbB therapeutic, an anti-MET therapeutic, or both, or a cell that has been contacted with a different amount of one or both of the therapeutic agents, or a reference value, such as an expected value for a given assay, etc.

In another aspect, the invention provides a method for reducing PI3K mediated signaling in a cancer cell by contacting the cell with an anti-ErbB therapeutic and an anti-MET therapeutic. In exemplary embodiments, the cancer cell has acquired a resistance to an anti-ErbB therapeutic and comprises elevated levels of MET activity and/or expression (e.g., associated with an activating mutation in the MET gene, a MET gene amplification, or HGF mediated MET activation). Methods for examining PI3K mediated signaling are known in the art. For example, U.S. Patent Publication No. 2005/0170439 describes methods to determine binding complexes formed between an ErbB receptor and PI3 kinase. Alternatively, the presence or absence of phosphorylated forms of proteins that are phosphorylated in response to PI3K activation (such as, for example, Akt) can be assayed using antibodies specific for the substrates. Antibodies that are specific for the various phosphorylated forms of PKB/AKT are commercially available (see e.g., New England Biolabs (UK) Ltd of Hitchin, Hertfordshire). Other suitable antibodies will be known to those of skill in the art. Immunoassays to measure these proteins can be carried out in many different and convenient ways that are well known to those skilled in the art. Alternatively, immunohistochemical techniques can be used to identify phosphorylated forms of PKB/AKT in cancer cells. In certain embodiments, it may be desirable to compare the level of PI3K mediated signaling in the cancer cell to a control, e.g., a cell that has not been contacted with an anti-ErbB therapeutic, an anti-MET therapeutic or both, or a cell that has been contacted with a different amount of one or both of the therapeutic agents, or a reference value, such as an expected value for a given assay, etc.

In another aspect, the invention provides a method for reducing ErbB-mediated signaling in a cancer cell by contacting the cell with an anti-ErbB therapeutic and an anti-MET therapeutic. In exemplary embodiments, the cancer cell has acquired a resistance to an anti-ErbB therapeutic and comprises elevated levels of MET activity and/or expression, for example, associated with an activating mutation in the MET gene, a MET gene amplification, or HGF mediated MET activation. The methods disclosed herein may be used to reduce signaling mediated by one or more of ErbB1, ErbB2, ErbB3 and/or ErbB4. Methods for examining ErbB-mediated signaling are known in the art. For example, antibodies specific for a substrate of an ErbB protein may by used to identify the presence of, or determine the amount of, phosphorylated substrate present in the cell (e.g., immunohistochemical techniques) or in a lysate from the cell (e.g., Western blotting techniques). Additionally, ErbB substrates may be immunoprecipitated from a cell lysate and used in an activity assay to determine whether they have been phosphorylated and thus activated by the ErbB receptor kinase thereby reflecting ErbB mediated signaling. In certain embodiments, it may be desirable to compare the level of ErbB-mediated signaling in the cancer cell to a control, e.g., a cell that has not been contacted with an anti-ErbB therapeutic, an anti-MET therapeutic, or both, or a cell that has been contacted with a different amount of one or both of the therapeutic agents, or a reference value, such as an expected value for a given assay, etc.

In another aspect, the invention provides a method for (i) restoring the sensitivity of a cancer cell to an anti-ErbB therapeutic, (ii) reducing resistance of a cancer cell to an anti-ErbB therapeutic, and/or (iii) treating acquired anti-ErbB therapeutic resistance in a cancer cell, by contacting the cell with an anti-ErbB therapeutic and an anti-MET therapeutic. In exemplary embodiments, the cancer cell has acquired a resistance to an anti-ErbB therapeutic and comprises elevated levels of MET activity and/or expression, e.g., associated with an activating mutation in the MET gene, a MET gene amplification, or HGF mediated MET activation. The methods disclosed herein may be used to restore the sensitivity, reduce the resistance, and/or treat an acquired resistance, of a cancer cell to one or more of the following: an anti-ErbB1 therapeutic, an anti-ErbB2 therapeutic, an anti-ErbB3 therapeutic and/or an anti-ErbB4 therapeutic. Methods for examining cell sensitivity and/or resistance to an anti-ErbB therapeutic are known in the art. For example, the amount of cell growth and/or proliferation and/or amount of apoptosis may be determined in the presence of the anti-ErbB/anti-MET combination therapy as compared to the anti-ErbB therapeutic alone. A decrease in the cell growth and/or proliferation and/or an increase in apoptosis of the cancer cell is indicative of an increase in sensitivity, or a reduction in resistance, to the anti-ErbB therapeutic. Methods for examining cell growth, proliferation and apoptosis are known in the art and are described further herein below.

In another aspect, the invention provides a method for reducing growth and/or proliferation of a cancer cell, or increasing apoptosis of a cancer cell, by contacting the cell with an anti-ErbB therapeutic and an anti-MET therapeutic. In exemplary embodiments, the cancer cell has acquired a resistance to an anti-ErbB therapeutic and comprises elevated MET activity and/or expression, e.g., associated with an activating mutation in the MET gene, a MET gene amplification, or HGF mediated MET activation. Methods for examining growth and/or proliferation and/or apoptosis of a cancer cell are well known in the art. Exemplary methods for determining cell growth and/or proliferation and/or apoptosis include, for example, Alamar Blue, Brd U, MTT, Trypan Blue exclusion, $^3$H-thymidine incorporation, and XTT assays. Kits for determining cell growth and/or proliferation and/or apoptosis are commercially available from a variety of sources. In certain embodiments, it may be desirable to compare the level of growth and/or proliferation and/or apoptosis of the cancer cell to a control, e.g., a cell that has not been contacted with an anti-ErbB therapeutic, an anti-MET therapeutic, or both, or a cell that has been contacted with a different amount of one or both of the therapeutic agents, or a reference value, such as an expected value for a given assay, etc.

3. Anti-ErbB and Anti-MET Therapeutics

Various methods described herein utilize anti-ErbB therapeutics and anti-MET therapeutics. Any type of therapeutic agent which exhibits anti-ErbB activity or anti-MET activity may be used in accordance with the methods described herein. A therapeutic having an anti-ErbB activity is anything which antagonizes (e.g., reduces or inhibits) at least one biological activity of an ErbB protein. Exemplary biological activities include, for example, tyrosine kinase activity (for ErbB1, ErbB2 or ErbB4), formation of protein-protein interactions (such as, for example, receptor homo- or heterodimerization, ligand binding, binding to a substrate, etc.), and ErbB mediated signaling. Similarly, a therapeutic having an anti-MET activity is anything which antagonizes (e.g., reduces or inhibits) at least one biological activity of a MET protein. Exemplary biological activity include, for example, tyrosine kinase activity, formation of protein-protein interactions (such as, for example, receptor homo- or hetero-dimerization, ligand binding, binding to a substrate, etc.), and MET mediated signaling. Exemplary anti-ErbB and anti-MET therapeutics include, for example, small molecule therapeutics, nucleic acid therapeutics (such as, for example, antisense nucleic acids, dsRNAs, siRNAs, or enzymatic nucleic acids) and protein therapeutics (such as, for example, an antibody). Additionally, various methods described herein involve methods of treating cancer that has developed a resistance to an anti-ErbB therapeutic. The methods may be used to treat cancers which have developed a resistance to any of the anti-ErbB therapeutics described herein for treatment purposes.

In certain embodiments, an anti-ErbB or anti-MET therapeutic is a small molecule therapeutic. Small molecule therapeutics include any small molecule that antagonizes at least one biological activity of or ErbB or MET. Exemplary small molecule therapeutics are kinase inhibitors. Other suitable small molecule therapeutics include small molecules that antagonize receptor dimerization or ligand binding. Suitable examples of anti-ErbB small molecule therapeutics and anti-MET small molecule therapeutics are provided below.

In one embodiment, an anti-ErbB or anti-MET therapeutic may be an antisense nucleic acid. By "antisense nucleic acid," it is meant a non-enzymatic nucleic acid compound that binds to a target nucleic acid by means of RNA-RNA, RNA-DNA or RNA-PNA (protein nucleic acid) interactions and alters the activity of the target nucleic acid (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can form a loop and binds to a substrate nucleic acid which forms a loop. Thus, an antisense molecule can be complementary to two (or more) non-contiguous substrate sequences, or two (or more) non-contiguous sequence portions of an antisense molecule can be complementary to a target sequence, or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49.

In other embodiments, an anti-ErbB or anti-MET therapeutic may be an siRNA. The term "short interfering RNA," "siRNA," or "short interfering nucleic acid," refers to any nucleic acid compound capable of mediating RNAi or gene silencing when processed appropriately be a cell. For example, the siRNA can be a double-stranded polynucleotide molecule comprising self-complementary sense and antisense regions, wherein the antisense region comprises complementarity to a target nucleic acid compound (e.g., an RTK). The siRNA can be a single-stranded hairpin polynucleotide having self-complementary sense and antisense regions, wherein the antisense region comprises complementarity to a target nucleic acid compound. The siRNA can be a circular single-stranded polynucleotide having two or more loop structures and a stem comprising self-complementary sense and antisense regions, wherein the antisense region comprises complementarity to a target nucleic acid compound, and wherein the circular polynucleotide can be processed either in vivo or in vitro to generate an active siRNA capable of mediating RNAi. The siRNA can also comprise a single stranded polynucleotide having complementarity to a target nucleic acid compound, wherein the single stranded polynucleotide can further comprise a terminal phosphate group, such as a 5'-phosphate (see for example Martinez et al., 2002, Cell., 110, 563-574), or 5',3'-diphosphate.

As described herein, siRNAs may be around 19-30 nucleotides in length, or 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotide siRNA molecules comprise a 3' hydroxyl group. In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of the siRNAs can be carried out by chemical synthetic methods or by recombinant nucleic acid techniques. Endogenous RNA polymerase of the treated cell may mediate transcription in vivo, or cloned RNA polymerase can be used for transcription in vitro. As used herein, siRNA molecules need not be limited to those molecules containing only RNA, but may contain a DNA strand, several DNA nucleotides, and/or encompasses chemically-modified nucleotides and non-nucleotides. For example, siRNA s may include modifications to either the phosphate-sugar backbone or the nucleoside, e.g., to reduce susceptibility to cellular nucleases, improve bioavailability, improve formulation characteristics, and/or change other pharmacokinetic properties. To illustrate, the phosphodiester linkages of natural RNA may be modified to include at least one of a nitrogen or sulfur heteroatom. Modifications in RNA structure may be tailored to allow specific genetic inhibition while avoiding a general response to double stranded RNA (dsRNA). Likewise, bases may be modified to block the activity of adenosine deaminase. The dsRNAs may be produced enzymatically or by partial/total organic synthesis, any modified ribonucleotide can be introduced by in vitro enzymatic or organic synthesis. Methods of chemically modifying RNA molecules can be adapted for modifying dsRNAs (see, e.g., Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of an siRNA can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). In certain cases, the dsRNAs of the disclosure lack 2'-hydroxy(2'-OH) containing nucleotides.

In certain embodiments, at least one strand of an siRNA molecule has a 3' overhang from about 1 to about 6 nucleotides in length, or from about 2 to about 4 nucleotides in length, or from about 1-3 nucleotides in length. In certain embodiments, one strand has a 3' overhang and the other strand may be blunt-ended or also have an overhang. The length of the overhangs may be the same or different for each strand. In order to further enhance the stability of an siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In other embodiments, an interfering RNA can also be in the form of a long double-stranded RNA. For example, the double stranded portion of the dsRNA may be at least 25, 50, 100, 200, 300 or 400 bases in length, or from about 400-800 bases in length. Optionally, the dsRNAs may be digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In other embodiments, an siRNA may be in the form of a hairpin structure (e.g., hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

PCT application WO 01/77350 describes an exemplary vector for bi-directional transcription of a transgene to yield both sense and antisense RNA transcripts of the same transgene in a eukaryotic cell. Accordingly, in certain embodiments, the present disclosure provides a recombinant vector having the following unique characteristics: it comprises a viral replicon having two overlapping transcription units arranged in an opposing orientation and flanking a transgene for an siRNA of interest, wherein the two overlapping transcription units yield both sense and antisense RNA transcripts from the same transgene fragment in a host cell.

In certain embodiments, an anti-ErbB or anti-MET therapeutic may be an enzymatic nucleic acid. By "enzymatic nucleic acid," it is meant a nucleic acid which has complementarity in a substrate binding region to a specified target gene, and also has an enzymatic activity which is active to specifically cleave a target nucleic acid. It is understood that the enzymatic nucleic acid is able to intermolecularly cleave a nucleic acid and thereby inactivate a target nucleic acid. These complementary regions allow sufficient hybridization of the enzymatic nucleic acid to the target nucleic acid and thus permit cleavage. One hundred percent complementarity (identity) is preferred, but complementarity as low as 50-75% can also be useful (see for example Werner and Uhlenbeck, 1995, Nucleic Acids Research, 23, 2092-2096; Hammann et al., 1999, Antisense and Nucleic Acid Drug Dev., 9, 25-31). The enzymatic nucleic acids can be modified at the base, sugar, and/or phosphate groups. As described herein, the term "enzymatic nucleic acid" is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acids with enzymatic activity. The specific enzymatic nucleic acids described herein are not meant to be limiting and those skilled in the art will recognize that all that is important in an enzymatic nucleic acid is that it has a specific substrate binding site which is complementary to one or more of the target nucleic acid regions, and that it have nucleotide sequences within or surrounding that substrate binding site which imparts a nucleic acid cleaving and/or ligation activity to the molecule (Cech et al., U.S. Pat. No. 4,987,071; Cech et al., 1988, 260 JAMA 3030). In one embodiment, an enzymatic nucleic acid is a ribozyme designed to catalytically cleave an mRNA transcripts to prevent translation of mRNA (see, e.g., PCT International Publication WO90/11364, published Oct. 4, 1990; Sarver et al., 1990, Science 247:1222-1225; and U.S. Pat. No. 5,093,246). In another embodiment, an enzymatic nucleic acid is a DNA enzyme. Methods of making and administering DNA enzymes can be found, for example, in U.S. Pat. No. 6,110,462.

In another embodiment, an anti-ErbB or anti-MET therapeutic may be an antibody, such as, for example, an antibody that binds to an ErbB protein (e.g., ErbB1, ErbB2, ErbB3, or ErbB4), a MET protein, an ErbB ligand (e.g., EGF, TGFα, AR, BTC, HB-EPR, NRG1, NRG2, NRG3, or NRG4), or a MET ligand (e.g., hepatocyte growth factor (HGF)). The term "antibody" as used herein is intended to include antigen binding fragments thereof. Antibodies can be fragmented using conventional techniques and the fragments screened for utility in the same manner as is suitable for whole antibodies. For example, F(ab')$_2$ fragments can be generated by treating antibody with pepsin. The resulting F(ab')$_2$ fragment can be treated to reduce disulfide bridges to produce Fab' fragments. Antibodies are further intended to include bispecific and chimeric molecules, as well as single chain (scFv) antibodies. Also included are trimeric antibodies; humanized antibodies, human antibodies, and single chain antibodies. All of these modified forms of antibodies as well as fragments of antibodies are intended to be included in the term "antibody".

Antibodies may be elicited by methods known in the art. For example, a mammal such as a mouse, a hamster or rabbit may be immunized with an immunogenic form of an ErbB protein, MET protein, ErbB ligand or MET ligand (e.g., an antigenic fragment which is capable of eliciting an antibody response). Alternatively, immunization may occur by using a nucleic acid, which in vivo expresses an ErbB protein, MET protein, ErbB ligand or MET ligand giving rise to the immunogenic response observed. Techniques for conferring immunogenicity on a protein or peptide include conjugation to carriers or other techniques well known in the art. For instance, a peptidyl portion of a polypeptide of the invention may be administered in the presence of adjuvant. The progress of immunization may be monitored by detection of antibody titers in plasma or serum. Standard ELISA or other immunoassays may be used with the immunogen as antigen to assess the levels of antibodies.

Following immunization, antisera reactive with a polypeptide of the invention may be obtained and, if desired, polyclonal antibodies isolated from the serum. To produce monoclonal antibodies, antibody producing cells (lymphocytes) may be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), as the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with the polypeptides of the invention and the monoclonal antibodies isolated.

In certain embodiments, anti-ErbB therapeutics and/or anti-MET therapeutics may be a protein display scaffold (see e.g., Hosse, R. J., et al., Protein Science, 15:14-27 (2006)) that binds to an ErbB protein (e.g., ErbB1, ErbB2, ErbB3, or ErbB4), a MET protein, an ErbB ligand (e.g., EGF, TGFα, AR, BTC, HB-EPR, NRG1, NRG2, NRG3, or NRG4), or a MET ligand (e.g., hepatocyte growth factor (HGF)). In one embodiment, the protein display scaffold is a fibronectin based "addressable" therapeutic binding molecule (see e.g., PCT publication Nos. WO 00/34784, WO 01/64942, and WO 02/032925). The fibronectin domain III (FnIII) loops comprise regions that may be subjected to random mutation and directed evolutionary schemes of iterative rounds of target binding, selection, and further mutation in order to develop useful therapeutic tools.

In certain embodiments, an anti-ErbB therapeutic and/or an anti-MET therapeutic may be a polypeptide that reduces binding between an ErbB receptor or MET receptor and its corresponding ligand. In one embodiment, the polypeptide may be a soluble ErbB or MET polypeptide, in particular a polypeptide comprising the extracellular domain of an ErbB or MET, such as, for example, any naturally occurring extracellular domain of an ErbB or MET protein as well as any variants thereof (including mutants, fragments and peptidomimetic forms) that retain ligand binding.

In certain embodiments, the ErbB or MET ligand-binding polypeptides include peptidomimetics. Peptidomimetics refer to chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the ErbB or MET ligand-binding polypeptides.

In certain aspects, functional variants or modified forms of the ErbB or MET ligand-binding polypeptides include fusion proteins having at least a portion of the ErbB or MET polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. In exemplary embodiments, an ErbB or MET-polypeptide is fused with a domain that stabilizes the ErbB or MET polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function).

Examples of anti-ErbB1 (anti-EGFR) therapeutics are known in the art. For example, small molecule anti-ErbB1 (EGFR) therapeutics include EGFR kinase inhibitors such as, for example, gefitinib (IRESSA™; AstraZeneca, London), erlotinib (TARCEVA™; Genentech, South San Francisco, Calif.), lapatinib, PF00299804, CI-1033, EKB-569, BIBW2992, ZD6474, AV-412, or HKI-272. Anti-EGFR protein therapeutics include, for example, anti-EGFR antibodies such as cetuximab (ERBITUX™, ImClone Systems Inc, New York, N.Y. and Bristol-Myers Squibb, Princeton, N.J.), panitumumab (VECTIBIX™, Amgen, Thousand Oaks, Calif.), EMD-7200 (Merck AG), ABX-EGF (Amgen Inc. and Abgenix Inc.), HR3 (Cuban Government), IgA antibodies (University of Erlangen-Nuremberg), TP-38 (IVAX).

Examples of anti-ErbB2 therapeutics include, for example, CP-724-714, CI-1033 (canertinib), HERCEPTIN™ (trastuzumab), OMNITARG™ (pertuzumab), TAK-165, GW-572016 (lonafamib), GW-282974, EKB-569, PI-166, dHER2 (HER2Vaccine), APC8024 (HER2Vaccine), anti-HER/2neu bispecific antibody, B7.her2IgG3, AS HER2 trifunctional bispecfic antibodies, mAB AR-209 and mAB 2B-1. Additional anti-ErbB2 therapeutics include those described in WO 98/02434, WO 99/35146, WO 99/35132, WO 98/02437, WO 97/13760, WO 95/19970, WO 2001/98277, U.S. Pat. No. 5,587,458, U.S. Pat. No. 5,877,305, U.S. Pat. Nos. 6,465,449, and 6,284,764.

Examples of anti-ErbB3 therapeutics include, for example, anti-ErbB3 antibodies (see e.g., U.S. Patent Publication No. 20040197332).

Examples of anti-ErbB4 therapeutics include, for example, anti-ErbB4 siRNAs (see e.g., Maatta et al., Mol. Biol. Cell 17: 67-79 (2006), or ErbB4 kinase inhibitors such as, for example, CI-1033, EKB-569, lapatinib, PF00299804, and AV412.

Anti-ErbB therapeutics also encompass therapeutics with multiple targets, such as, for example, pan ERBB receptor inhibitors including GW572016, CI-1033, EKB-569, and Omnitarg™.

Exemplary anti-MET therapeutics include, for example, MET kinase inhibitors such as, for example, PHA-665752 (Pfizer, Inc, La Jolla, Calif.), PF-02341066 (Pfizer, Inc, La Jolla, Calif.), SU11274, SU5416, XL-880, MGCD265, XL184, ARQ 197, MP-470, SGX-523, JNJ38877605, AMG 102, and OA-5D5

4. Methods for Detection of ErbB and MET Modifications

In various embodiments, the methods described herein may involve detection of an ErbB activating mutation, an ErbB gene amplification, ligand induced ErbB activation, a MET activating mutation, a MET gene amplification, and/or ligand mediated MET activation. Various examples of ErbB and MET activating mutations are described further herein and include mutations outside of the ErbB and MET sequences themselves that lead to an increase in at least one biological activity of an ErbB or MET protein. Any art recognized technique may be used for detecting mutations or gene amplifications including methods involving analysis of a nucleic acid (either DNA or RNA), analysis of a protein product, and/or analysis of protein activity. Such detection methods encompass both qualitative and quantitative detection methods. Exemplary methods are described further herein.

Genetic Mutations

A genetic mutation may be detected by contacting a nucleic acid sample with a probe that is capable of specifically hybridizing to the mutant sequence and then detecting hybridization of the probe. The probe generally is detectably labeled, such as with a radioisotope ($^3$H, $^{32}$P, $^{33}$P etc), a fluorescent agent (rhodamine, fluorescein, etc.) or a chromogenic agent to facilitate detection of hybridization. One of skill in the art will readily be able to design a suitable probe for detecting a mutation of interesting based on the disclosure provided herein. For example, probes may be an antisense oligomer, for example PNA, morpholino-phosphoramidates, LNA or 2'-alkoxyalkoxy and may be from about 8 nucleotides to about 100 nucleotides, about 10 to about 75, about 15 to about 50, or about 20 to about 30 nucleotides in length. In certain embodiments, one or more probes may be isolated on a solid support and a detectably labeled nucleic acid sample may be hybridized to the probe on the support. For example, the probe may be part of a microarray comprising a plurality of immobilized sequences. Methods for array hybridization and analysis are known to those of skill in the art.

Alternatively, genetic mutations may be detected in a sample by amplifying a nucleic acid sequence or portion thereof suspected of containing a mutation, and comparing the electrophoretic mobility of the amplified nucleic acid to the electrophoretic mobility of corresponding wild-type gene or fragment thereof. A difference in the mobility indicates the presence of a mutation in the amplified nucleic acid sequence. Electrophoretic mobility may be determined on polyacrylamide gel. This method is particularly useful for detection of insertion and/or deletion mutations.

Another suitable method for detection of mutations involves use of Enzymatic Mutation Detection (EMD) (Del Tito et al, Clinical Chemistry 44:731-739, 1998). EMD uses the bacteriophage resolvase T4 endonuclease VII, which scans along double-stranded DNA until it detects and cleaves structural distortions caused by base pair mismatches resulting from point mutations, insertions and deletions. Detection of fragments formed by resolvase cleavage, for example by gel electrophoresis, indicates the presence of a mutation. Benefits of the EMD method are a single protocol to identify point mutations, deletions, and insertions assayed directly from PCR reactions eliminating the need for sample purification, shortening the hybridization time, and increasing the signal-to-noise ratio. Mixed samples containing up to a 20-fold excess of normal DNA and fragments up to 4 kb in size can been assayed using this method. However, EMD scanning does not identify particular base changes that occur in mutation positive samples requiring additional sequencing procedures to identity of the mutation if necessary. CEL I enzyme can be used similarly to resolvase T4 endonuclease VII as demonstrated in U.S. Pat. No. 5,869,245.

Detection of point mutations may be accomplished by molecular cloning and sequencing of polynucleotide using techniques well known in the art. Alternatively, the polymerase chain reaction (PCR) can be used to amplify gene sequences directly from a genomic DNA preparation from a biological sample, such as, for example, cancer cells. The DNA sequence of the amplified sequences can then be determined and mutations identified therefrom. The polymerase chain reaction is well known in the art and described in, for example, Saiki et al., Science 239:487, 1988; U.S. Pat. No. 4,683,203; and U.S. Pat. No. 4,683,195.

Additionally, allele specific PCR can also be used to detect mutations (see Ruano and Kidd, Nucleic Acids Research, Vol. 17, p. 8392, 1989). According to this technique, primers are used which hybridize to the 3' ends of a particular sequence.

If the particular sequence is not present due to a mutation, an amplification product is not produced.

Insertions and deletions of genes can also be detected by cloning, sequencing and amplification. In addition, restriction fragment length polymorphism (RFLP) can be used to score sequence alterations. Single stranded conformation polymorphism (SSCP) analysis can also be used to detect base change variants (see e.g., Orita et al., Proc. Natl. Acad. Sci. USA Vol. 86, pp. 2766-2770, 1989, and Genomics, Vol. 5, pp. 874-879, 1989). Other techniques for detecting insertions and deletions as are known in the art can be used in accordance with the methods described herein.

Mismatch detection (e.g., detection of duplexes that are not 100% complementary) can also be used to detect point mutations in a DNA or RNA sequence (see e.g., U.S. Pat. Nos. 5,459,039, 5,556,750, 5,679,522, 5,861,482, 5,922,539, and 6,008,031).

RNase protection, which involves mismatch cleavage, may also be used to detect mutations, including point mutations (see e.g., Winter et al., Proc. Natl. Acad. Sci. USA, Vol. 82, p. 7575, 1985 and Meyers et al., Science, Vol. 230, p. 1242, 1985). In brief, this method involve use of a labeled riboprobe which is complementary to a wild-type sequence. The riboprobe and either mRNA or DNA isolated from a sample are annealed (hybridized) together and subsequently digested with the enzyme RNase A which is able to detect some mismatches in a duplex RNA structure. If a mismatch is detected by RNase A, it cleaves at the site of the mismatch thereby producing shorter fragments which can be detected using a separation technology such as gel electrophoresis.

In a similar manner, DNA probes can be used to detect mismatches, through enzymatic or chemical cleavage. See, e.g., Cotton et al., Proc. Natl. Acad. Sci. USA, Vol. 85, 4397, 1988; and Shenk et al., Proc. Natl. Acad. Sci. USA, Vol. 72, p. 989, 1975. Alternatively, mismatches can be detected by shifts in the electrophoretic mobility of mismatched duplexes relative to matched duplexes. See, e.g., Cariello, Human Genetics, Vol. 42, p. 726, 1988. With either riboprobes or DNA probes, the cellular mRNA or DNA which might contain a mutation can be amplified using PCR before hybridization. Changes in DNA sequences can also be detected using Southern hybridization, especially if the changes are gross rearrangements, such as deletions and insertions.

Gene Amplification

The presence of a target gene that has undergone amplification may be evaluated by determining the copy number of the target gene, i.e., the number of DNA sequences in a cell encoding the target protein. Generally, a normal diploid cell has two copies of a given autosomal gene but the copy number can be increased by gene amplification or duplication. Methods of evaluating the copy number of a particular gene are well known in the art, and include, hybridization and amplification based assays. In some embodiments, the actual number of amplified copies of the gene is determined. Alternatively, a qualitative measure of gene amplification may be obtained. Various methods for detecting gene amplification include, for example, amplification-based methods and hybridization based methods (such as southern blotting, FISH, CGH and microarray techniques) and are described further herein.

Amplification-Based Methods

Amplification based methods for detecting gene amplification can be used to measure copy number of an amplified sequence and involves amplification (for example, using Polymerase Chain Reaction or PCR) of a sequence of interest. In a quantitative amplification, the amount of amplification product will be proportional to the amount of template in the original sample. Comparison to appropriate controls provides a measure of the copy-number of a sequence of interest in a given sample. The presence of a higher level of an amplification product, as compared to a control, is indicative of amplified sequence.

Methods of quantitative amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided, for example, in Innis et al. (1990) PCR Protocols, A Guide to Methods and Applications, Academic Press, Inc. N.Y. The nucleic acid sequences for the ErbB and MET genes are known and are sufficient to enable one of skill to select primers that can be used to amplify any portion of these genes.

Real time PCR is another amplification technique that can be used to determine gene copy levels or levels of mRNA expression (see, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For gene copy levels, total genomic DNA is isolated from a sample. For mRNA levels, mRNA is extracted from a sample and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.). To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from $10-10^6$ copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan™ probes are well known in the art. Detailed protocols for real-time quantitative PCR are provided, for example, for RNA in: Gibson et al., 1996, A novel method for real time quantitative RT-PCR. Genome Res., 10:995-1001; and for DNA in: Heid et al., 1996, Real time quantitative PCR. Genome Res., 10:986-994. TaqMan™ based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq™, results in the cleavage of the TaqMan™ probe. This cleavage separates the 5' fluorescent dye and the 3'*quenching agent*, thereby resulting in an increase in fluorescence as a function of amplification (*see*, for *example*, world wide web at *perkin-elmer.com*).

Hybridization-Based Assays

Hybridization assays can also be used to detect gene copy number. Hybridization-based assays include, but are not limited to, traditional "direct probe" methods such as Southern blots or in situ hybridization (e.g., FISH), and "comparative probe" methods such as comparative genomic hybridization (CGH). The methods can be used in a wide variety of formats including, but not limited to substrate bound (e.g., membrane or glass) methods or array-based approaches as described below.

One method for evaluating gene copy number involves Southern transfer. Methods for doing Southern Blots are known to those of skill in the art (see Current Protocols in Molecular Biology, Chapter 19, Ausubel, et al., Eds., Greene Publishing and Wiley-Interscience, New York, 1995, or Sambrook et al., Molecular Cloning: A Laboratory Manual, 2d Ed. vol. 1-3, Cold Spring Harbor Press, NY, 1989). In such an assay, genomic DNA (typically fragmented and separated on an electrophoretic gel) is hybridized to a probe specific for a target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. An intensity level that is higher than the control is indicative of an amplified sequence.

Fluorescence in situ hybridization (FISH) may also be used to determine the copy number of a gene. FISH is known to those of skill in the art (see Angerer, 1987 Meth. Enzymol., 152: 649). In a typical in situ hybridization assay, cells or tissue sections are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. In some applications it is necessary to block the hybridization capacity of repetitive sequences. Thus, in some embodiments, tRNA, human genomic DNA; or Cot-1 DNA is used to block non-specific hybridization.

Comparative Genomic Hybridization (CGH) may also be used to determine gene copy number. In comparative genomic hybridization methods, a "test" collection of nucleic acids (e.g., from a possible tumor) is labeled with a first label, while a second collection (e.g., from a normal cell or tissue) is labeled with a second label. The ratio of hybridization of the nucleic acids is determined by the ratio of the first and second labels binding to each fiber in an array. Differences in the ratio of the signals from the two labels, for example, due to gene amplification in the test collection, is detected and the ratio provides a measure of the gene copy number, corresponding to the specific probe used. A cytogenetic representation of DNA copy-number variation can be generated by CGH, which provides fluorescence ratios along the length of chromosomes from differentially labeled test and reference genomic DNAs.

DNA copy numbers may also be analyzed via microarray-based platforms. Details of various microarray methods can be found in the literature. See, for example, U.S. Pat. No. 6,232,068; Pollack et al., Nat. Genet., 23(1):41-6, (1999), Pastinen (1997) Genome Res. 7: 606-614; Jackson (1996) Nature Biotechnology 14:1685; Chee (1995) Science 274: 610; WO 96/17958, Pinkel et al. (1998) Nature Genetics 20: 207-211 and others.

The DNA used to prepare an array is not critical. For example, the arrays can include genomic DNA, e.g. overlapping clones that provide a high resolution scan of a portion of the genome containing the desired gene, or of the gene itself. Genomic nucleic acids can be obtained from, e.g., HACs, MACs, YACs, BACs, PACs, PIs, cosmids, plasmids, inter-Alu PCR products of genomic clones, restriction digests of genomic clones, cDNA clones, amplification (e.g., PCR) products, and the like. Arrays can also be produced using oligonucleotide synthesis technology. Thus, for example, U.S. Pat. No. 5,143,854 and PCT Patent Publication Nos. WO 90/15070 and WO 92/10092 teach the use of light-directed combinatorial synthesis of high density oligonucleotide arrays.

Hybridization protocols suitable for use with microarray methods are described, e.g., in Albertson (1984) EMBO J. 3: 1227-1234; Pinkel (1988) Proc. Natl. Acad. Sci. USA 85: 9138-9142; EPO Pub. No. 430,402; Methods in Molecular Biology, Vol. 33: In Situ Hybridization Protocols, Choo, ed., Humana Press, Totowa, N.J. (1994), Pinkel et al. (1998) Nature Genetics 20: 207-211, or of Kallioniemi (1992) Proc. Natl. Acad Sci USA 89:5321-5325 (1992), etc.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Expression Levels

Detection of ErbB and/or MET activating mutations or gene amplifications may also be detected by analyzing ErbB and/or MET expression levels including RNA expression levels and protein expression levels. Analysis of RNA expression levels may involve determination of one or more transcriptional products such as hnRNAs, mRNAs, and/or one or more spliced variants of an mRNA. Various protein products may also be measured to determine expression levels including, for example, proteins, protein variants arising from spliced mRNA variants, and post translationally modified proteins.

RNA Expression

Any suitable means of measuring expression levels of RNA products can be used in accordance with the methods described herein. For example, the methods may utilize a variety of polynucleotides that specifically hybridize to one or more ErbB and/or MET RNA products including, for example, oligonucleotides, cDNA, DNA, RNA, PCR products, synthetic DNA, synthetic RNA, or other combinations of naturally occurring of modified nucleotides which specifically hybridize to one or more ErbB and/or MET RNA products. Such polynucleotides may be used in combination with the methods to measure RNA expression described further herein including, for example, array hybridization, RT-PCR, nuclease protection and northern blots.

In certain embodiments, array hybridization may be used to evaluate levels of ErbB and/or MET RNA expression. Array hybridization utilizes nucleic acid members stably associated with a support that can hybridize with ErbB and/or MET RNA expression products. The length of a nucleic acid member attached to the array can range from 8 to 1000 nucleotides in length and are chosen so as to be specific for the ErbB and/or MET RNA products. The array may comprise, for example, one or more nucleic acid members that are specific for ErbB and/or MET, or variants thereof (e.g., splice variants), including, for example, EGFR, ErbB2, ErbB3, ErbB4, and MET, and ligands of any of the foregoing, such as, for example, ErbB ligands (e.g., EGF, TGFα, AR, BTC, HB-EPR, NRG1, NRG2, NRG3, or NRG4) or a MET ligand (e.g., hepatocyte growth factor (HGF)). The nucleic acid members may be RNA or DNA, single or double stranded, and/or may be oligonucleotides or PCR fragments amplified from cDNA. Preferably oligonucleotides are approximately 10-100, 10-50, 20-50, or 20-30 nucleotides in length. Portions of the expressed regions of ErbB and/or MET can be utilized as probes on the array. More particularly oligonucleotides complementary to ErbB and/or MET genes and or cDNAs derived from the ErbB and/or MET genes are useful. For oligonucleotide based arrays, the selection of oligonucleotides corresponding to the gene of interest which are useful as probes is well understood in the art. More particularly it is important to choose regions which will permit hybridization to the target nucleic acids. Factors such as the Tm of the oligonucleotide, the percent GC content, the degree of secondary structure and the length of nucleic acid are important factors. See for example U.S. Pat. No. 6,551,784.

Arrays may be constructed, custom ordered, or purchased from a commercial vendor. Various methods for constructing arrays are well known in the art. For example, methods and techniques applicable to oligonucleotide synthesis on a solid support, e.g., in an array format have been described, for example, in WO 00/58516, U.S. Pat. Nos. 5,143,854, 5,242, 974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752 and Zhou et al., Nucleic Acids Res. 32: 5409-5417 (2004).

In an exemplary embodiment, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other methods for constructing arrays include, for example, light-directed methods utilizing masks (e.g., VLSIPS™ methods described, for example, in U.S. Pat. Nos. 5,143,854, 5,510,270 and 5,527,681), flow channel methods (see e.g., U.S. Pat. No. 5,384,261), spotting methods (see e.g., U.S. Pat. No. 5,807,522), pin-based methods (see e.g., U.S. Pat. No. 5,288,514), and methods utilizing multiple supports (see e.g., U.S. Pat. Nos. 5,770,358, 5,639,603, and 5,541,061).

In certain embodiments, an array of nucleic acid members stably associated with the surface of a support is contacted with a sample comprising target nucleic acids under hybridization conditions sufficient to produce a hybridization pattern of complementary nucleic acid members/target complexes in which one or more complementary nucleic acid members at unique positions on the array specifically hybridize to target nucleic acids. The identity of target nucleic acids which hybridize can be determined with reference to location of nucleic acid members on the array.

Control nucleic acid members may be present on the array including nucleic acid members comprising oligonucleotides or nucleic acids corresponding to genomic DNA, housekeeping genes, vector sequences, negative and positive control genes, and the like. Control nucleic acid members are calibrating or control genes whose function is not to tell whether a particular gene of interest is expressed, but rather to provide other useful information, such as background or basal level of expression.

Other control nucleic acids on the array may be used as target expression control nucleic acids and mismatch control nucleotides to monitor non-specific binding or cross-hybridization to a nucleic acid in the sample other than the target to which the probe is directed. Mismatch probes thus indicate whether a hybridization is specific or not. For example, if the target is present, the perfectly matched probes should be consistently brighter than the mismatched probes. In addition, if all control mismatches are present, the mismatch probes are used to detect a mutation.

An array provided herein may comprise a substrate sufficient to provide physical support and structure to the associated nucleic acids present thereon under the assay conditions in which the array is employed, particularly under high throughput handling conditions.

The substrate may be biological, non-biological, organic, inorganic, or a combination of any of these, existing as particles, strands, precipitates, gels, sheets, tubing, spheres, beads, containers, capillaries, pads, slices, films, plates, slides, chips, etc. The substrate may have any convenient shape, such as a disc, square, sphere, circle, etc. The substrate is preferably flat or planar but may take on a variety of alternative surface configurations. The substrate may be a polymerized Langmuir Blodgett film, functionalized glass, Si, Ge, GaAs, GaP, $SiO_2$, $SIN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art in view of this disclosure.

In certain embodiments, a target nucleic acid sample may comprise total mRNA or a nucleic acid sample corresponding to mRNA (e.g., cDNA) isolated from a biological sample. Total mRNA may be isolated from a given sample using, for example, an acid guanidinium-phenol-chloroform extraction method and polyA+mRNA may be isolated using oligo dT column chromatography or using (dT)n magnetic beads (see, e.g., Sambrook et al., Molecular Cloning: A Laboratory Manual (2nd ed.), Vols. 1-3, Cold Spring Harbor Laboratory, (1989), or Current Protocols in Molecular Biology, F. Ausubel et al., ed. Greene Publishing and Wiley-Interscience, New York (1987). In certain embodiments, total RNA may be extracted using TRIzol™ reagent (GIBCO/BRL, Invitrogen Life Technologies, Cat. No. 15596). Purity and integrity of RNA may be assessed by absorbance at 260/280 nm and agarose gel electrophoresis followed by inspection under ultraviolet light.

In certain embodiments, it may be desirable to amplify the target nucleic acid sample prior to hybridization. One of skill in the art will appreciate that whatever amplification method is used, if a quantitative result is desired, care must be taken to use a method that maintains or controls for the relative frequencies of the amplified nucleic acids. Methods of quantitative amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid. Detailed protocols for quantitative PCR are provided in PCR Protocols, A Guide to Methods and Applications, Innis et al., Academic Press, Inc. N.Y., (1990).

In certain embodiments, the target nucleic acid sample mRNA is reverse transcribed with a reverse transcriptase and a primer consisting of oligo dT and a sequence encoding the phage T7 promoter to provide single-stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro transcription are well known to those of skill in the art (see, e.g., Sambrook, supra.) and this particular method is described in detail by Van Gelder, et al., 1990, Proc. Natl. Acad. Sci. USA, 87: 1663-1667 who demonstrate that in vitro amplification according to this method preserves the relative frequencies of the various RNA transcripts. Moreover, Eberwine et al. Proc. Natl. Acad. Sci. USA, 89: 3010-3014 provide a protocol that uses two rounds of amplification via in vitro transcription to achieve greater than $10^6$ fold amplification of the original starting material thereby permitting expression monitoring even where biological samples are limited.

Detectable labels suitable for use in accordance with the methods described herein include any composition detectable by spectroscopic, photochemical, biochemical, immunochemical, electrical, optical or chemical means. Useful labels include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The labels may be incorporated by any of a number of means well known to those of skill in the art. For example, the label may be simultaneously incorporated during the amplification step in the preparation of the sample nucleic acids. Thus, for example, polymerase chain reaction (PCR) with labeled primers or labeled nucleotides will provide a labeled amplification product. Additionally, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing of the nucleic acid and subsequent attachment (ligation) of a nucleic acid linker joining the sample nucleic acid to a label (e.g., a fluorophore).

In certain embodiments, the fluorescent modifications are by cyanine dyes e.g. Cy-3/Cy-5 dUTP, Cy-3/Cy-5 dCTP (Amersham Pharmacia) or alexa dyes (Khan, et al., 1998, Cancer Res. 58:5009-5013).

In certain embodiments, it may be desirable to simultaneously hybridize two target nucleic acid samples to the array, including, for example, a target nucleic acid sample from a subject (e.g., a subject having or at risk of having cancer or another hyperproliferative disorder) and a control nucleic acid sample (e.g., a healthy individual). In a further embodiment, one target nucleic acid sample may be obtained from a tumor or other cancerous growth of a subject, while the second target nucleic acid sample may be obtained from healthy biological material from the same subject. The two target samples used for comparison are labeled with different fluorescent dyes which produce distinguishable detection signals, for example, targets from a control sample are labeled with Cy5 and targets from a subject to be monitored or diagnosed are labeled with Cy3. The differently labeled target samples are hybridized to the same microarray simultaneously. The labeled targets may be purified using methods known in the art, e.g., by ethanol purification or column purification.

In certain embodiments, the target nucleic acid samples will include one or more control molecules which hybridize to control probes on the microarray to normalize signals generated from the microarray. Labeled normalization targets may be, for example, nucleic acid sequences that are perfectly complementary to control oligonucleotides that are spotted onto the microarray as described above. The signals obtained from the normalization controls after hybridization provide a control for variations in hybridization conditions, label intensity, reading efficiency and other factors that may cause the signal of a perfect hybridization to vary between arrays. Signals (e.g., fluorescence intensity) read from all other probes in the array may be divided by the signal (e.g., fluorescence intensity) from the control probes, thereby normalizing the measurements.

Normalization targets may be selected to reflect the average length of the other targets present in the sample or they may be selected to cover a range of lengths. The normalization control(s) also can be selected to reflect the (average) base composition of the other probes in the array. In certain embodiments, only one or a few normalization probes are used and they are selected such that they hybridize well (i.e., have no secondary structure and do not self hybridize) and do not match any target molecules. Normalization probes may be localized at any position in the array or at multiple positions throughout the array to control for spatial variation in hybridization efficiency. For example, normalization controls may be located at the corners or edges of the array as well as in the middle.

Nucleic acid hybridization to an array involves incubating a denatured probe or target nucleic acid member on an array and a target nucleic acid sample under conditions wherein the probe or target nucleic acid member and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA: DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches. Methods of optimizing hybridization conditions are well known to those of skill in the art (see, e.g., Laboratory Techniques in Biochemistry and Molecular Biology, Vol. 24: Hybridization With Nucleic acid Probes, P. Tijssen, ed. Elsevier, N.Y., (1993)).

Following hybridization, non-hybridized labeled or unlabeled nucleic acids are removed from the support surface by washing thereby generating a pattern of hybridized target nucleic acid on the substrate surface. A variety of wash solutions are known to those of skill in the art and may be used. The resultant hybridization patterns of labeled, hybridized oligonucleotides and/or nucleic acids may be visualized or detected in a variety of ways, with the particular manner of detection being chosen based on the particular label of the target nucleic acid sample, where representative detection means include scintillation counting, autoradiography, fluorescence measurement, calorimetric measurement, light emission measurement and the like.

Following hybridization, washing step and/or subsequent treatments, the resultant hybridization pattern is detected. In detecting or visualizing the hybridization pattern, the intensity or signal value of the label will be not only be detected but quantified, e.g., the signal from each spot on the hybridized array will be measured and compared to a unit value corresponding to the signal emitted by a known number of end labeled target nucleic acids to obtain a count or absolute value of the copy number of each end-labeled target that is hybridized to a particular spot on the array in the hybridization pattern.

Methods for analyzing the data collected from array hybridizations are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test nucleic acids from the remaining data. The resulting data is displayed as an image with the intensity in each region varying according to the binding affinity between associated oligonucleotides and/or nucleic acids and the test nucleic acids.

In certain embodiments, expression levels of ErbB and/or MET RNA products can be measured by amplifying the RNA products from a sample using reverse transcription (RT) in combination with the polymerase chain reaction (PCR). In certain embodiments, the RT can be quantitative as would be understood to a person skilled in the art.

Total RNA, or mRNA from a sample may be used as a template and a primer specific to the transcribed portion of a RTKs is used to initiate reverse transcription. Methods of reverse transcribing RNA into cDNA are well known and are described, for example, in Sambrook et al., 1989, supra. Primer design can be accomplished utilizing commercially available software (e.g., Primer Designer 1.0, Scientific Software etc.) or methods that are standard and well known in the art. Primer Software programs can be used to aid in the design and selection of primers include, for example, The Primer Quest software which is available through the following web site link: biotools.idtdna.com/primerquest/. Additionally, the following website links are useful when searching and updating sequence information from the Human Genome Database for use in RTK primer design: 1) the NCBI LocusLink Homepage: world wide web at ncbi.nlm.nih.gov/LocusLink/, and 2) Ensemble Human Genome Browser: world wide web at ensembl.org/Homosapiens, preferably using pertinent RTK information such as Gene or Sequence Description, Accession or Sequence ID, Gene Symbol, RefSeq #, and/or Uni-Gene #.

General guidelines for designing primers that may be used in accordance with the methods described herein include the following: the product or amplicon length may be ~100-150 bases, the optimum Tm may be ~60° C., or about 58-62° C., and the GC content may be ~50%, or about 45-55%. Additionally, it may be desirable to avoid certain sequences such as one or more of the following: (i) strings of three or more bases at the 3'-end of each primer that are complementary to another part of the same primer or to another primer in order to reduce primer-dimer formation, (ii) sequences within a primer that are complementary to another primer sequence, (iii) runs of 3 or more G's or C's at the 3'-end, (iv) single base repeats greater than 3 bases, (v) unbalanced distributions of G/C— and A/T rich domains, and/or (vi) a T at the 3'-end.

The product of the reverse transcription is subsequently used as a template for PCR. PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts. The method of PCR is well known in the art. PCR, is performed as described in Mullis and Faloona, 1987, Methods Enzymol., 155: 335.

QRT-PCR, which is quantitative in nature, can also be performed to provide a quantitative measure of RTK gene expression levels. In QRT-PCR reverse transcription and PCR can be performed in two steps, or reverse transcription combined with PCR can be performed concurrently. One of these techniques, for which there are commercially available kits such as TaqMan™ (Perkin Elmer, Foster City, Calif.), is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96 well plates so that samples derived from many individuals are processed and measured simultaneously. The TaqMan™ system has the additional advantage of not requiring gel electrophoresis and allows for quantification when used with a standard curve.

A second technique useful for detecting PCR products quantitatively is to use an intercalating dye such as the commercially available QuantiTect SYBR Green PCR (Qiagen, Valencia Calif.). RT-PCR is performed using SYBR green as a fluorescent label which is incorporated into the PCR product during the PCR stage and produces a fluorescence proportional to the amount of PCR product. Additionally, other systems to quantitatively measure mRNA expression products are known including Molecular Beacons™.

Additional techniques to quantitatively measure RNA expression include, but are not limited to, polymerase chain reaction, ligase chain reaction, Qbeta replicase (see, e.g., International Application No. PCT/US87/00880), isothermal amplification method (see, e.g., Walker et al. (1992) PNAS 89:382-396), strand displacement amplification (SDA), repair chain reaction, Asymmetric Quantitative PCR (see, e.g., U.S. Publication No. US200330134307A1) and the multiplex microsphere bead assay described in Fuja et al., 2004, Journal of Biotechnology 108:193-205.

The level of gene expression can be measured by amplifying RNA from a sample using transcription based amplification systems (TAS), including nucleic acid sequence amplification (NASBA) and 3SR. See, e.g., Kwoh et al (1989) PNAS USA 86:1173; International Publication No. WO 88/10315; and U.S. Pat. No. 6,329,179. In NASBA, the nucleic acids may be prepared for amplification using conventional phenol/chloroform extraction, heat denaturation, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once with a polymerase such as T7 or SP6. The resulting products, whether truncated or complete, indicate target specific sequences.

Several techniques may be used to separate amplification products. For example, amplification products may be separated by agarose, agarose-acrylamide or polyacrylamide gel electrophoresis using conventional methods. See Sambrook et al., 1989. Several techniques for detecting PCR products quantitatively without electrophoresis may also be used (see for example PCR Protocols, A Guide to Methods and Applications, Innis et al., Academic Press, Inc. N.Y., (1990)). For example, chromatographic techniques may be employed to effect separation. There are many kinds of chromatography which may be used: adsorption, partition, ion-exchange and molecular sieve, HPLC, and many specialized techniques for using them including column, paper, thin-layer and gas chromatography (Freifelder, Physical Biochemistry Applications to Biochemistry and Molecular Biology, 2nd ed., Wm. Freeman and Co., New York, N.Y., 1982).

Amplification products must be visualized in order to confirm amplification of the nucleic acid sequences of interest. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

Alternatively, visualization may be achieved indirectly. Following separation of amplification products, a labeled, nucleic acid probe is brought into contact with the amplified nucleic acid sequence of interest. The probe may be conjugated to a chromophore, radiolabeled, or conjugated to a binding partner, such as an antibody or biotin, where the other member of the binding pair carries a detectable moiety.

Additionally, detection may be carried our using Southern blotting and hybridization with a labeled probe. The techniques involved in Southern blotting are well known to those of skill in the art and may be found in many standard books on molecular protocols. See Sambrook et al., 1989, supra. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

In certain embodiments, nuclease protection assays (including both ribonuclease protection assays and S1 nuclease assays) can be used to detect and quantitate ErbB and/or MET RNA products. In nuclease protection assays, an antisense probe (e.g., radiolabeled or nonisotopic labeled) hybridizes in solution to an RNA sample. Following hybridization, single-stranded, unhybridized probe and RNA are degraded by nucleases. An acrylamide gel is used to separate the remaining protected fragments. Typically, solution hybridization can accommodate up to ~100 μg of sample RNA whereas blot hybridizations may only be able to accommodate ~20-30 μg of RNA sample.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

In certain embodiments, a Northern blot assay can be used to ascertain an RNA transcript size, identify alternatively spliced RNA transcripts, and the relative amounts of RNA products of the ErbB and/or MET genes. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabeled cDNA, either containing the full-length, single stranded DNA or a fragment of that DNA sequence may be any length up to at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Non-limiting examples of isotopes include $^{3}H$, $^{14}C$, $^{32}P$, $^{35}S$, $^{36}C$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme may be conjugated to the selected probe by reaction with bridging molecules such as carbodiimides, diisocyanates, glutaraldehyde and the like. Any enzymes known to one of skill in the art can be utilized, including, for example, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

Protein Expression

Activating mutations or gene amplifications may also be detected by examining ErbB and/or MET protein expression levels. Any art recognized technique for measuring protein expression levels may be including, for example, gel electrophoresis (including 2-D gel electrophoresis), mass spectrometry and antibody binding. Preferred method for assaying protein levels in a biological sample include antibody-based techniques, such as immunoblotting (western blotting), immunohistological assays, enzyme linked immunosorbent assays (ELISA), radioimmunoassays (RIA), or protein chips. For example, ErbB and/or MET specific monoclonal antibodies can be used both as an immunoadsorbent and as an enzyme-labeled probe to detect and quantify ErbB and/or MET. The amount of ErbB and/or MET present in the sample can be calculated by reference to the amount present in a standard preparation using a linear regression computer algorithm. In another embodiment, ErbB and/or MET may be immunoprecipitated from a biological sample using an antibody specific for an ErbB and/or MET protein. The isolated proteins may then be run on an SDS-PAGE gel and blotted (e.g., to nitrocellulose or other suitable material) using standard procedures. The blot may then be probed with an anti-ErbB and/or anti-MET specific antibody to determine the expression level of the ErbB and/or MET protein.

Gel electrophoresis, immunoprecipitation and mass spectrometry may be carried out using standard techniques, for example, such as those described in Molecular Cloning A Laboratory Manual, $2^{nd}$ Ed., ed. by Sambrook, Fritsch and Maniatis (Cold Spring Harbor Laboratory Press: 1989), Harlow and Lane, Antibodies: A Laboratory Manual (1988 Cold Spring Harbor Laboratory), G. Suizdak, Mass Spectrometry for Biotechnology (Academic Press 1996), as well as other references cited herein.

Antibodies suitable for isolation and detection of ErbB and/or MET may be purchased commercially from a variety of sources. Antibodies specific for ErbB and/or MET may also be produced using standard techniques as described further herein (see e.g., Current Protocols in Immunology and Using Antibodies: A Laboratory Manual).

Activity Levels

ErbB and/or MET activating mutations or gene amplifications may also be detected by measuring ErbB and/or MET activity. Various methods for determining ErbB and/or MET activity are known to those of skill in the art and are described further herein. Exemplary methods for measuring ErbB and/or MET activity include, for example, examining one or more of the following: ErbB and/or MET phosphorylation, ErbB and/or MET kinase activity, or ErbB and/or MET mediated signaling. ErbB and/or MET activity may be determined in cell based assays, using a cell lysate, or in vitro using purified or partially purified components. In one embodiment, the ErbB and/or MET phosphorylation may be examined using an antibody array as described in U.S. Pat. No. 6,197,599. Commercially available antibody arrays that bind to a plurality of phosphorylation receptor tyrosine kinases include the RayBio™ Phosphorylation Antibody Array and R&D System's Phospho-RTK Array.

Ligand Mediated Activation

Ligand mediated activation of ErbB and/or MET may be determined using a variety of art recognized techniques that are described further herein. For example, ligand mediated activation may be determined by detecting a gene amplification of the ligand gene or by detecting an activating mutation in ligand gene. Various methods for detecting gene amplification and gene mutations are described herein above. In alternative embodiments, ligand mediated activation of ErbB or MET may be analyzed by determining the level ErbB or MET activity where an increase in ErbB or MET activity is associated with an increase in the amount of ligand. Methods for determining ErbB and MET activity are described herein above. In other embodiments, ligand mediated activation of ErbB or MET may be determined by assaying the level of ligand protein expression or activity, for example, using immunohistochemical analysis, ELISA, or an activity assay. ErbB ligands are known in the art and include EGF, TGFα, AR, BTC, HB-EPR, NRG1, NRG2, NRG3, and NRG4. Hepatocyte growth factor or HGF is a ligand for MET.

5. Assays, Kits and Cell Lines

In another aspect, the invention provides methods for identifying an anti-MET therapeutic. In general, the methods involve contacting a cell with a combination of one or more anti-ErbB therapeutics and a test compound, e.g., a candidate anti-MET therapeutic agent. The cell may be, for example, a cancer cell that has acquired resistance to an anti-ErbB therapeutic. Additionally, the cell may also comprise an activating mutation in the MET gene or a MET gene amplification. The effectiveness of the test compound as an anti-MET therapeutic may be determined by detecting a decrease in one or more biological activities of a MET protein. Determination of a decrease in a biological activity of a MET protein may be examined, for example, by detecting one or more of the following changes in a cellular process: decreased ErbB phosphorylation, decreased MET phosphorylation, decreased ErbB-MET association, decreased PI3K activity, decreased AKT phosphorylation, decreased cell growth, decreased cell proliferation or increased apoptosis. In certain embodiments, it may be desirable to compare the results to a control such as, for example, a duplicate assay conducted in the absence of a test compound or a duplicate assay conducted in the presence of a test compound having known anti-MET activity. In yet other embodiments, a control may be a reference number in a database. In certain embodiments, the methods described herein may be used to identify a test compound that decreases a biological activity of a MET protein by at least about 2-fold, 3-fold, 5-fold, 10-fold, 15-fold, 20-fold, 25-fold, or more, relative to the biological activity in the absence of the test compound. Exemplary biological activities of MET include, for example, kinase activity, protein-protein interactions (such as, for example, receptor homo- or hetero-dimerization, ligand binding, or binding to a substrate, etc.), or MET mediated signaling.

Test compounds to be tested for activity in the assays described herein can include proteins (including post-translationally modified proteins), peptides (including chemically or enzymatically modified peptides), or small molecules (including carbohydrates, steroids, lipids, anions or cations, drugs, small organic molecules, oligonucleotides, antibodies, and genes encoding proteins of the agents or antisense molecules), including libraries of compounds. The test compounds can be naturally occurring (e.g., found in nature or isolated from nature) or can be non-naturally occurring (e.g., synthetic, chemically synthesized or man-made).

If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J Med. Chem. 37,2678, 1994; Cho et al., Science 261, 1303, 1993; Carell et al., Angew. Chem. Int. Ed Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, BioTechniques 13, 412-421, 1992), or on beads (Lam, Nature 354, 82-84, 1991), chips (Fodor, Nature 364, 555-556, 1993), bacteria or spores (Ladner, U.S. Pat. No. 5,223,409), plasmids (Cull et al., Proc. Natl. Acad. Sci. U.S.A. 89, 1865-1869, 1992), or phage (Scott & Smith, Science 249, 386-390, 1990; Devlin, Science 249, 404-406, 1990); Cwirla et al., Proc. Natl. Acad. Sci. 97, 6378-6382, 1990; Felici, J. Mol. Biol. 222, 301-310, 1991; and Ladner, U.S. Pat. No. 5,223,409).

Test compounds can be screened for the ability to antagonize MET activity using high throughput screening. Using high throughput screening, many discrete compounds can be tested in parallel so that large numbers of test compounds can be quickly screened. The most widely established techniques utilize 96-well microtiter plates. In addition to the plates, many instruments, materials, pipettors, robotics, plate washers, and plate readers are commercially available to fit the 96-well format.

Alternatively, free format assays, or assays that have no physical barrier between samples, can be used. Assays involving free formats are described, for example, in Jayawickreme et al., Proc. Natl. Acad. Sci. U.S.A. 19, 1614-18 (1994); Chelsky, "Strategies for Screening Combinatorial Libraries: Novel and Traditional Approaches," reported at the First Annual Conference of The Society for Biomolecular Screening in Philadelphia, Pa. (Nov. 7-10, 1995); and Salmon et al., Molecular Diversity 2, 57-63 (1996). Another high throughput screening method is described in Beutel et al., U.S. Pat. No. 5,976,813.

In another aspect, the invention provides a method for producing a cell with acquired resistance to an anti-ErbB therapeutic. The methods involve contacting a cell which is sensitive to an anti-ErbB therapeutic with at least one anti-ErbB therapeutic and identifying cells that acquire resistance to the anti-ErbB therapeutic. In an exemplary embodiment, the cell produced by the methods described herein does not contain a mutation in an ErbB gene that confers resistance to the anti-ErbB therapeutic agent, e.g., the cell has acquired a resistance due a different mechanism or a mutation in a sequence that is not an ErbB sequence. The cells may be contacted with the anti-ErbB therapeutic for at least 5 days, 1 week, 2 weeks, 3 weeks, 4 weeks, 6 weeks, 8 weeks, or more. The cells may be contacted with an increasing concentration of the anti-ErbB therapeutic over time. For example, as cell growth recovers in the presence of a given concentration, the concentration may be increased, and the process repeated. For example, the concentration of the anti-ErbB therapeutic may be increased from about $IC_{30}$ to about $IC_{40}$, $IC_{50}$, and $IC_{60}$, or greater, over time. Various methods for identifying cells that have acquired a resistance to the anti-ErbB therapeutic may be used and are described further herein. For example, identification of cells that have acquired a resistance to an anti-ErbB therapeutic include, for example, one or more of the following in the presence of the anti-ErbB therapeutic: increased cell growth, increased cell proliferation, decreased apoptosis, increased ErbB phosphorylation, increased MET phosphorylation, increased ErbB-MET association, increased AKT phosphorylation, increased PI3 kinase mediated signaling, increased ErbB mediated signaling, increased MET mediated signaling, presence of an activating MET mutation, presence of a MET gene amplification, overexpression of MET, overexpression of a MET ligand, etc. In certain embodiments, it may be desirable to compare the sensitivity of the cell to a control such as, for example, a duplicate assay conducted in the absence of the anti-ErbB therapeutic. In yet other embodiments, a control may be a reference number in a database. In certain embodiments, the methods described herein may be used to produce a cell line that has at least about a 2-fold, 3-fold, 5-fold, 10-fold, 15-fold, 20-fold, 25-fold, or greater, increase in resistance to an anti-ErbB therapeutic relative to a control.

In various embodiments, it may be desirable to contact the cell with one, two, three, four, five, or more different anti-ErbB therapeutics so that the cell develops a resistance to one or more of the anti-ErbB therapeutics. In certain embodiments, it may be desirable to contact the cell with a single type of anti-ErbB therapeutic (e.g., small molecule therapeutics, nucleic acid therapeutics, or protein therapeutics). Alternatively, combinations of differing anti-ErbB therapeutic classes may also be used, such as, for example, a combination of an ErbB kinase inhibitor and an siRNA, or an ErbB kinase inhibitor and an anti-ErbB antibody, etc. In certain embodiments, it may be desirable to contact the cell with an anti-ErbB therapeutic that is directed to only one of ErbB1, ErbB2, ErbB3, or ErbB4 so that the cell develops a resistance, for example, to an anti-ErbB1 therapeutic. In other embodiments, it may be desirable to contact the cell with a combination of anti-ErbB therapeutics that target different ErbB proteins. For example, it may be desirable to contact the cell with an anti-ErbB1 (anti-EGFR) therapeutic and an anti-ErbB2 therapeutic so that the cell develops a resistance to both types of therapeutics. In yet other embodiments, the methods may involve contacting a cell with one or more multispecific ErbB therapeutics, e.g., one or more kinase inhibitor reagents that target two or more ErbB proteins. Examples of such therapeutic agents are described further herein.

In another aspect, the invention provides a cell or cell line produced by the methods described herein. In particular, cells that have acquired a resistance to an anti-ErbB therapeutic that do not contain a mutation in an ErbB sequence that gives rise to such resistance are provided herein.

In other aspects, the invention provides kits useful for research purposes, drug discovery, diagnostic purposes, monitoring therapeutic progress, optimizing dosage, etc.

In one embodiment, the invention provides kits for treating patients suffering from a cancer that is resistance to an anti-ErbB therapeutic. Such kits may comprise at least one component for detecting a MET activating mutation, a MET gene amplification, or HGF mediated MET activation (as described above) and anti-ErbB therapeutic and/or an anti-MET therapeutic (as described above). For example, a kit may comprise an anti-ErbB therapeutic and at least one component for detecting a MET activating mutation, a MET gene amplification, or HGF mediated MET activation. Such kits may be useful for monitoring subjects being treated with an anti-ErbB therapeutic to identify subjects that develop a resistance to the treatment. In another embodiment, a kit may comprise at least one component for detecting a MET activating mutation, a MET gene amplification, or HGF mediated MET activation, an anti-ErbB therapeutic and an anti-MET therapeutic. Such kits are useful for monitoring subjects being treated with an anti-ErbB therapeutic to identify those subjects that develop a resistance to the treatment and also provide a modified therapeutic regimen for those subjects who are discovered to be resistant to the anti-ErbB therapy and have an activating mutation of MET or a MET gene amplification. Such kits are merely exemplary and many other types of kits may be envisioned by one of skill in the art based on the disclosure provided herein.

Components for detecting a MET activating mutation or gene amplification may be any component that can be used in conjunction with the various methods described herein for detecting mutations or gene amplifications. Exemplary components include, for example, an antibody or an antigen-binding fragment thereof that binds MET (or phospho-MET), a ligand of MET, or a substrate of MET, a set of PCR primers that specifically amplify MET, or a ligand of MET, or a solid support comprising at least a fragment of the polynucleotide sequence encoding MET or MET ligand attached thereto (such as a microarray chip). The kit may further contain one or more of the following: a detection label, a positive control, a negative control, a MET protein, reagents for conducting a kinase assay, reagents for conducting a binding assay, reagents for measuring ErbB, MET and/or PI3 kinase mediated signaling, instructions for use, a reaction vessel, buffers, etc. The kit may also comprise components for detecting an ErbB activating mutation or gene amplification.

In certain embodiments, a kit may comprise a cancer cell having activating mutations or gene amplifications of ErbB and MET that is resistant to treatment with an anti-ErbB therapeutic. The kit may also comprise one or more of the following: a detection label, a positive control, a negative control, instructions for use, a reaction vessel, buffers, an anti-ErbB therapeutic, an anti-MET therapeutic, reagents for measuring cell proliferation, growth and/or apoptosis, reagents for conducting a kinase assay, reagents for conducting a binding assay, reagents for measuring ErbB, MET and/or PI3 kinase mediated signaling, etc. Such kits may be useful, for example, for identifying MET therapeutics, testing combinations of anti-ErbB and anti-MET therapeutics, optimizing drug dosing or treatment regimens, etc.

Respective components of the kit may be combined so as to realize a final concentration that is suitable for the reaction. Further, in addition to these components, the kit may comprise a buffer that gives a condition suitable for the reaction. Protein components, such as antibodies, substrates, ligands, kinases, etc. may be combined with stabilizing agents. For example, the kit components may be stored and/or shipped in the presence of about 1% BSA and about 1% polyols (e.g., sucrose or fructose) to prevent protein denaturation after lyophilization.

In certain embodiments, the kits provided herein may also comprise components for measuring the expression of ErbB and/or MET protein and RNA products. Such components include materials and reagents required for measuring the expression of such protein and RNA products, such as, for example: (1) reagents for purifying RNA from a biological sample; (2) primers for generating test nucleic acids; (3) dNTPs and/or rNTPs (either premixed or separate), optionally with one or more uniquely labeled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g. hybridization and washing buffers; (7) labeled probe purification reagents and components, like spin columns, etc.; (8) protein purification reagents; and (9) signal generation and detection reagents, e.g., streptavidin-alkaline phosphatase conjugate, chemifluorescent or chemiluminescent substrate, and the like. In particular embodiments, the kits comprise prelabeled quality controlled protein and or RNA isolated from a biological sample for use as a control.

In some embodiments, the kits may comprise RT-PCR components, or hybridization components. For example, the kits may comprise nucleic acid arrays, protein arrays, antibody arrays, phospho-protein arrays, phospho-antibody arrays, etc. Such kits can be used to determine the expression level of MET, ErbB, ligand thereof, and/or substrates thereof.

6. Pharmaceutical Compositions

In certain embodiments, the methods described herein may involve administration of one or more anti-ErbB therapeutics and/or one or more anti-MET therapeutics to a subject. The anti-ErbB therapeutics and/or anti-MET therapeutics may be formulated in a conventional manner using one or more physiologically acceptable carriers or excipients. For example, anti-ErbB therapeutics and/or anti-MET therapeutics, and their physiologically acceptable salts and solvates, may be formulated for administration by, for example, injection (e.g. SubQ, 1M, 1P), inhalation or insufflation (either through the mouth or the nose) or oral, buccal, sublingual, transdermal, nasal, parenteral or rectal administration. In one embodiment, anti-ErbB therapeutics and/or anti-MET therapeutics may be administered locally, at the site where the target cells are present, i.e., in a specific tissue, organ, or fluid (e.g., blood, cerebrospinal fluid, tumor mass, etc.).

Anti-ErbB therapeutics and/or anti-MET therapeutics can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozanges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), anti-ErbB therapeutics and/or anti-MET therapeutics may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

Anti-ErbB therapeutics and/or anti-MET therapeutics may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

In addition, anti-ErbB therapeutics and/or anti-MET therapeutics may also be formulated as a depot preparation. Such long acting formulations may be administered by implantation (for example subcutaneously or intramuscularly) or by intramuscular injection. Thus, for example, anti-ErbB therapeutics and/or anti-MET therapeutics may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

In one embodiment, an anti-ErbB therapeutic and/or an anti-MET therapeutic is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other non-toxic organic solvents, glycerin, mineral oil, silicone, petroleum jelly, lanolin, fatty acids, vegetable oils, parabens, waxes, and the like.

Pharmaceutical compositions (including cosmetic preparations) may comprise from about 0.00001 to 100% such as from 0.001 to 10% or from 0.1% to 5% by weight of one or more anti-ErbB therapeutics and/or anti-MET therapeutics described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of an anti-ErbB therapeutic and/or an anti-MET therapeutic, or by insertion of a sustained release device that releases an anti-ErbB therapeutic and/or an anti-MET therapeutic. An anti-ErbB therapeutic and/or an anti-MET therapeutic may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds may be injected directly into the vitreous and aqueous humour. In a further alternative, the compounds may be administered systemically, such as by intravenous infusion or injection, for treatment of the eye.

Methods for delivering nucleic acid therapeutics are known in the art (see, e.g., Akhtar et al., 1992, Trends Cell Bio., 2, 139; and Delivery Strategies for Antisense Oligonucleotide Therapeutics, ed. Akhtar, 1995; Sullivan et al., PCT Publication No. WO 94/02595). These protocols can be utilized for the delivery of virtually any nucleic acid. Nucleic acids can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example though the use of conjugates and biodegradable polymers. For a comprehensive review on drug delivery strategies, see 1-10 et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400. More detailed descriptions of nucleic acid delivery and administration are provided in Sullivan et al., supra, Draper et al., PCT Publication No. WO 93/23569, Beigelman et al., PCT Publication No. WO 99/05094, and Klimuk et al., PCT Publication No. WO 99/04819.

Toxicity and therapeutic efficacy of anti-ErbB therapeutics and/or anti-MET therapeutics can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Anti-ErbB therapeutics and/or anti-MET therapeutics that exhibit large therapeutic indexes are preferred. While anti-ErbB therapeutics and/or anti-MET therapeutics that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

EXEMPLIFICATION

The invention now being generally described, it will be more readily understood by reference to the following examples which are included merely for purposes of illustration of certain aspects and embodiments of the present invention, and are not intended to limit the invention in any way.

Example 1

MET Amplification Leads to EGFR Kinase Inhibitor Resistance

Tyrosine kinase inhibitors (TKIs) have emerged as effective anti-cancer therapies for tumors in which the target kinase is activated by a genetic mechanism. Compelling clinical examples include the use of imatinib for the treatment of chronic myelogenous leukemia (CML; BCR-ABL translocation) or gastrointestinal stromal tumors (GISTS; activating mutations in KIT or PDGFRA), and epidermal growth factor receptor (EGFR) TKIs gefitinib and erlotinib for the treatment of non-small cell lung cancer (NSCLC) harboring activating mutations in EGFR (1-4).

Somatic mutations in EGFR occur in 10-15% of Caucasian and 30-40% of Asian NSCLC tumors and are located in exons 18-21 of the EGFR tyrosine kinase domain. Two common types of mutations, a series of overlapping exon 19 deletions and an exon 21 missense mutation (L858R), account for 85% of all known EGFR mutations (5). Treatment of EGFR mutant cell lines with gefitinib leads to apoptosis similar to the impressive clinical responses observed in patients (6). However, while EGFR mutant NSCLCs initially respond to EGFR inhibitors, acquired resistance to gefitinib and erlotinib ultimately develops in the vast majority of patients treated with these agents. In 50% of such patients, a single secondary mutation, a substitution of methionine for threonine at position 790 (T790M), has been identified (7, 8). However, the mechanisms for acquired resistance in the remaining tumors are unknown. It has been shown that EGFR mutant tumors specifically utilize ERBB3 to activate PI3K/Akt signaling and that downregulation of the ERBB3/PI3K/Akt signaling pathway is necessary for gefitinib to induce apoptosis in EGFR mutant NSCLC (9, 10). Notably, persistent ERBB3 phosphorylation has also been demonstrated to lead to gefitinib resistance in ERBB2 amplified breast cancer cells (11).

To explore additional mechanisms of gefitinib resistance, resistant clones of the gefitinib hypersensitive ($IC_{50}$ 10 nM) EGFR exon 19 deletion (del E746_A750) mutant NSCLC cell line, HCC827, were generated by exposing the cells to increasing concentrations of gefitinib for 6 months. The resulting cell line HCC827 GR (Geftinib Resistant) and 6 clones isolated from single cells were resistant to gefitinib in vitro ($IC_{50}$>10 µM; FIG. 1A). Unlike in the parental cell line, phosphorylation of ERBB3 and Akt were maintained in the presence of gefitinib in the GR cells (FIG. 1B). To determine whether this observation was due to a secondary mutation in EGFR, the entire EGFR coding region from all 6 GR clones were sequenced which revealed the known exon 19 deletion mutation. However, the T790M mutation was not detected. In addition, a sensitive enzymatic method (Surveyor™), capable of detecting genetic variants even at a 1% frequency, was used to screen for alterations in the entire EGFR coding sequence of all 6HCC827 GR clones (12). No differences from the parental HCC827 cell line were detected. Furthermore the irreversible EGFR inhibitor CL-387,785, which can inhibit the growth of NSCLC cell lines harboring the T790M mutation, did not suppress the growth of the HCC827 GR cell lines (13).

To determine whether the aberrant activation of another receptor might be mediating the observed resistance, a phospho-receptor tyrosine kinase (RTK) array (R&D systems) was used to compare the effects of gefitinib on a panel of 42 different phosphorylated RTKs in HCC827 and HCC827 GR5 cells (FIG. 1C). In the HCC827 cell line EGFR, ERBB3, ERBB2 and MET were all phosphorylated, which were either completely or markedly reduced following 1 µM gefitinib treatment. In contrast, there was marked phosphorylation of MET and persistent phosphorylation of ERBB3 and EGFR in the HCC827 GR cells even in the presence of gefitinib (FIG. 1C). To further explore the underlying mechanism of resistance we performed genome wide copy number analyses of the HCC827 GR cell lines and compared them to the parental HCC827 cells using the Human Mapping 250K Sty single nucleotide polymorphism (SNP) array (FIG. 1D). In the resistant cell lines, a marked focal amplification in the long arm of chromosome 7 (encompassing 7g31.1 to 7g33.3) was detected which was not present in the parental cell line. This region contains the MET proto-oncogene (FIG. 1E). Quantitative PCR was used to confirm that MET was amplified 5-10 fold in all the HCC827 resistant cell lines compared to the parental HCC827 cell line (FIG. 6). Using mRNA expression profiling we further compared mRNA expression profiles in the GR and parental cell lines (FIG. 8). Of the 20 sequences most differentially over-expressed in the GR cells, MET itself was represented 3 times. The entire MET coding region from all 6 HCC827 GR clones were sequenced and no MET mutations were detected. Together, these findings suggest that MET amplification leads to increased MET expression which is associated with phosphorylation of MET, EGFR and ERBB3 in the presence of gefitinib and in vitro resistance to gefitinib in the HCC827 GR cell lines.

Figure 7:
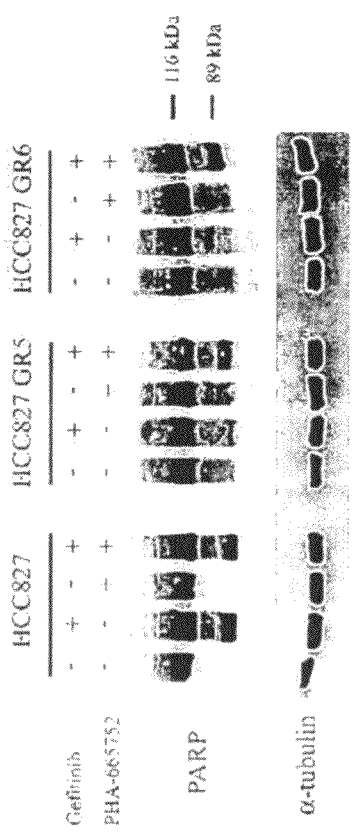
FIG. 7. Parental and resistant cells are treated with gefitinib alone, PHA-665,752 alone or both drugs in combination. Cell extracts are immnublotted and proteins detected with indicated antibodies. HCC827 GR cells undergo apoptosis only following treatment with both gefitinib and the MET kinase inhibitor PHA-665,752. In contrast, gefitinib alone is sufficient to induce apoptosis as measure by the appearance of cleaved (89 kDA) PARP.

To determine whether an increase in MET signaling might underlie the acquired resistance to gefitinib, it was examined whether MET inhibition would suppress the growth of HCC827 GR cells. HCC827 GR cells were exposed to PHA-665,752, a MET tyrosine kinase inhibitor, alone or in combination with gefitinib (14). While the HCC827 GR5 cells were resistant to both gefitinib and PHA-665,752 alone, in combination there was greater than 85% growth inhibition at concentrations of >33 nM of both drugs (FIG. 2A), accompanied by marked apoptosis (FIG. 7). Similar findings were observed with all of the other HCC827 GR clones. Next, the effects of gefitinib and PHA-665,752 on EGFR signaling in the resistant cell lines was examined. In the HCC827 GR cells, unlike in the parental cells, gefitinib by itself, reduces but it is unable to fully inhibit phosphorylation of EGFR, and has minimal effect on p-ERBB3 or p-Akt (FIG. 2B). However, in combination with PHA-665,752, ERBB3 and Akt phosphorylation are completely suppressed in the HCC827 GR cells. Of note, the residual EGFR phosphorylation observed with gefitinib treatment was also eliminated upon addition of PHA-665,752, suggesting that the residual EGFR phosphorylation was due to MET kinase activity as has been previously described (15). To more precisely define the mechanism by which PI3KlAkt was being activated in the HCC827 GR cells, the p85 regulatory subunit of PI3K was immunoprecipitated and co-precipitating proteins were analyzed. In the parental HCC827 cell line, two major phosphotyrosine proteins, ErbB3 and growth-factor-receptor-bound protein 2 (Grb2)-associated binder 1 (Gab1), a known MET adapter protein (16), co-precipitate with p85 (FIG. 2C). Both interactions were disrupted in the presence of gefitinib. In contrast, both ERBB3 and Gab1 still co-precipitated with p85 in the HCC827 GR cells in the presence of gefitinib alone, however these interactions were completely disrupted in the presence of both gefitinib and PHA-665,752 (FIG. 2C). These observations are consistent with the loss of phospho-ERBB3 observed in cell extracts (FIG. 2B) and suggest that MET can trigger the activation of ERBB3 independent of EGFR kinase activity. Treatment of the HCC827 GR cells with PHA-665,752 alone blocks Gab-1 association with p85, but has minimal effect on P-Akt levels (FIGS. 2B and 2C) thereby demonstrating that association of Gab-1 with PI3K is not necessary for Akt phosphorylation in these gefitinib resistant cell lines. Importantly, down-regulation of MET using short hairpin (sh) RNAs directed against two different regions of MET also restored the sensitivity of HCC827 GRs to gefitinib (FIG. 2D)(17). Moreover, both of the MET specific shRNAs downregulated MET to the level found in the parental HCC827 cell line (see FIG. 2B) and restored the ability of gefitinib to downregulate both ERBB3 and Akt phosphorylation in these cell lines (FIG. 2E). Together, these findings suggest that MET amplification leads to persistent activation of PI3KlAkt signaling in the presence of gefitinib by maintaining ERBB3 phosphorylation.

MET amplification and its association with in vitro sensitivity to PHA-665,752 has recently been reported in gastric cancer cell lines (18). Thus, it was determined whether other cell lines with MET amplification also utilize ERBB3 to activate PI3K/Akt signaling. Similar to the HCC827 GR cells, ERBB3 was found to associate with p85 in H1993 NSCLC cells and in SNU638 and MKN45 gastric cancer cells. This association was disrupted by PHA-665,752, but not by gefitinib, the dual EGFRJERBB2 inhibitor lapatinib or by CL-387,785 (FIG. 3A). Thus, MET leads to ERBB3 phosphorylation and coupling to PI3K in an EGFR- and ERBB2-independent manner. Similarly ERBB3 and Akt phosphorylation were only inhibited by PHA-665,752 (FIG. 3A). In addition, ERBB3 was downregulated in the SNU-638 cells by lentivirally infecting them with an ERBB3 specific shRNA which led to a marked decrease in p-AKT (FIG. 3B) and to inhibition of growth (FIG. 3C). Together these studies suggest that the observations with HCC827 GR cells that ERBB3 is tyrosine-phosphorylated in a MET-dependent manner as a mechanism for activation of PI3K/Akt and are generalizeable to other MET amplified cells.

It was then determined whether MET could directly lead to ERBB3 phosphorylation. ERBB3 was expressed alone or in combination with MET in Chinese hamster ovary (CHO) cells which normally do not express detectable levels of EGFR, ERBB2 or ERBB3. In CHO cells co-expressing MET and ERBB3, there was marked phosphorylation of ERBB3 which was blocked by PHA-665,752 but not by high doses of gefitinib, lapatinib or the SRC family kinase inhibitor PP2 (FIG. 3D). In these cells, the tyrosine phosphorylated ERBB3 co-immunoprecipitated p85 in a MET kinase-dependent manner (FIG. 3E). It was also observed that ERBB3 and MET co-precipitated from the CHO cells (FIGS. 3E and 3F). Together, these findings suggest that MET can associate with ERBB3 and promote ERBB3 phosphorylation and coupling to PI3K in a non-ERBB or SRC dependent manner.

It was next examined whether MET amplification could occur in EGFR mutant NSCLC patients with acquired resistance to gefitinib. 18 patients were analyzed, all of whom had obtained initial partial responses to gefitinib or erlotinib, but had subsequently developed growth of their cancer while receiving gefitinib or erlotinib. Both quantitative PCR (n=11; when only tumor derived DNA was available) or fluorescence in situ hybridization (FISH; n=7 where tumor sections were available) for the MET locus were used. In 8 patients, paired tumor specimens were available before and after the development of resistance to gefitinib while in 10 patients specimens were available only following clinical resistance to gefitinib or erlotinib (FIG. 5 and FIG. 9). Among the 8 patients with paired samples, MET amplification was detected in 2 of the post-treatment specimens but was not present in the pre-treatment specimens. In patient 1 the MET amplification in the post-treatment specimen was similar to the level of amplification seen in the HCC827 GR cell lines (FIG. 5 and FIG. 6). In addition, MET amplification was also detected in 2 other patients where only post treatment specimens were available (patients 12 and 13). Overall MET amplification was detected in 4/18 (22%) of gefitinib/erlotinib resistant tumor specimens. Importantly MET amplification was observed in 3 specimens without an EGFR T790M mutation and in 1 specimen with a concurrent EFGR T790M mutation. Interestingly, patient 12 had both EGFR T790M and MET amplification but each mode of resistance occurred separately in 2 different sites of relapse (FIG. 5). These findings suggest that MET amplification can be detected in NSCLC patients with resistance to gefitinib. Furthermore, multiple mechanisms of resistance can occur concurrently in the same patient.

Methods

Cell Culture and Reagents

The EGFR mutant NSCLC cell lines HCC827 (del E746_A750), H3255 (L858R), and H3255 GR used in this study and have been extensively characterized (3, 30-31, 10). 111993 and BT474 cells were obtained from American Type Culture Collection (ATCC; Manassas, Va.). SNU-638 and MKN-45 gastric cancer cells were obtained from Dr. Won Ki Kang (Samsung Medical Center, Seoul, Korea) and have been previously characterized (18, 32). HCC827, H 1993 SNU-638 and MKN-45 cell lines were maintained in RPMI 1640 (Cellgro; Mediatech Inc., Herndon, Calif.) supplemented with 10% FBS (20% for MKN-45), 100 units/mL penicillin, 100 units/mL streptomycin, and 2 mM glutamine. 113255 and H3255 GR were maintained in ACL-4 media (Life Technologies, Inc., Rockville, Md.) supplemented with 5% FBS, 100 units/mL penicillin, 100 units/mL streptomycin, and 2 mM glutamine.

Gefitinib was obtained from commercial sources and was purified through an ethyl acetate extraction. The resulting product was verified by liquid chromatography and mass spectrometry. Lapatinib was purchased from American Custom Chemical Corporation (San Diego, Calif.). C1-387,785 was purchased from Calbiochem. PHA-665,752 was a gift of Pfizer. Stock solutions of all drugs were prepared in DMSO and stored at −20° C.

Cell Proliferation and Growth Assays

Growth and inhibition of growth was assessed by MTS assay. This assay, a colorimetric method for determining the number of viable cells, is based on the bioreduction of 3-(4, 5-dimethylthiazol-2-yl)-5-(3-carboxymethoxyphenyl)-2-(4-sulfophenyl)-2H-tetrazolium (MTS) by cells to a formazan product that is soluble in cell culture medium, can be detected spectrophotometrically and was performed according to previously established methods (3, 31, 10).

The cells were exposed to treatment for 72 hours and the number of cells used per experiment determined empirically and has been previously established (31). All experimental points were set up in six to twelve wells and all experiments were repeated at least three times. The data was graphically displayed using GraphPad Prism version 3.00 for Windows, (GraphPad Software; world wide web at graphpad.com). The curves were fitted using a non-linear regression model with a sigmoidal dose response.

Antibodies and Western Blotting

Cells grown under the previously specified conditions were lysed in the following lysis buffer: 20 mM Tris, pH 7.4/150 mM NaCl/1% Nonidet P-40/10% glycerol/1 mM EDTA/1 mM EGTA/5 mM sodium pyrophosphate/50 mM NaF/10 nM (3-glycerophosphate/1 mM sodium vanadate/0.5 mM DTT/4 µg/ml leupeptin/4 µg/ml pepstatin/4 µg/ml apoprotein/1 mM PMSF. After cell lysis, lysates were centrifuged at 16,000×g for 5 min at 4° C. The supernatant was used for subsequent procedures. Western blot analyses were conducted after separation by SDS/PAGE electrophoresis and transfer to nitrocellulose membranes. Immunoblotting was performed according to the antibody manufacturers' recommendations. Antibody binding was detected using an enhanced chemiluminescence system (New England Nuclear Life Science Products Inc.).

Anti-phospho-Akt (Ser-473), anti-total Akt, anti-EGFR, and anti-phospho-ErbB-3 (Tyr-1289) antibodies were obtained from Cell Signaling Technology. Anti-ErbB-3 antibody was obtained from Lab Vision. The phospho-specific EGFR (pY1068), MET (pY 1234/1235), total ERK1/2, phospho-ERK1/2 (pT185/pY187) antibodies were purchased from Biosource International Inc. Anti-p85 antibody was obtained from Upstate Biotechnology. The total Met (C-28) antibody was purchased from Santa Cruz Biotechnology (Santa Cruz, Calif.).

Generation of In Vitro Gefitinib Resistant HCC827

In order to generate a resistant cell line, HCC827 cells were exposed to increasing concentrations of gefitinib similar to our previously described methods using H3255 (10). Gefitinib concentrations were increased stepwise from 1 to 100 nM when the cells resumed growth kinetics similar to the untreated parental cells. Cells that were able to grow in 100 nM of gefitinib were obtained after 6 months from initial drug exposure. To confirm the emergence of a resistant clone, MTS assays were performed following growth at each concentration after allowing the cells to grow in drug free condition for at least 4 days. The resistant HCC827 cells were passed 17 times in the absence of gefitinib and maintained their resistance as confirmed by MTS assays. Six individual clones were isolated (HCC827 GR1, GR2, GR5, GR6, GR7 and GR8) and all were confirmed independently to be resistant to gefitinib. HCC827 cells were maintained concomitantly without gefitinib and their sensitivity to gefitinib was examined every 5 passages. There was no significant change in the sensitivity to gefitinib in parental cells during the period.

SURVEYOR™ analyses

The entire EGFR coding region from the HCC827 GR clones was examined for genetic alterations using a modification of previously described sensitive gene scanning method (10, 12). Seven overlapping cDNA segments covering the entire EGFR coding region were generated and analyzed as previously described (12). The PCR primers are available upon request.

cDNA Sequencing of Cell Lines

Total RNA was isolated from cell lines using Trizol™ (Invitrogen, Carlsbad, Calif.) and purified using RNeasy™ minielute cleanup kit (Qiagen, Valencia, Calif.). cDNA was transcribed from 2 µg of total RNA with Superscript II Reverse Transcriptase (Invitrogen Life technologies, Carlsbad, Calif.). The cDNA was used as template for subsequent PCR amplifications of EGFR and MET. The details of the PCR conditions and the primers have been previously published (3, 17).

MET shRNA Constructs and Lentiviral Infection

MET shRNA constructs cloned in pLKO. 1 puro vector were obtained from Harvard RNAi consortium and have been previously characterized (10µ, 17). Each construct contained a 21 bp sequence targeting different regions of MET, a 6 nueclotide hairpin sequence (CTCGAG), and a 21 bp complementary strand sequence. A vector containing green fluorescent protein (GFP) was used as a control. The specific shRNA sequences are available upon request. Lentivirus production and infections were performed as previously described (10).

SNP and Expression Analyses

HCC827 and HCC827 GR cells were plated to 60% confluence in serum containing media and total RNA harvested as described above 6 hours following feeding of the cells. RNA specimens were then processed and hybridized to the Affymetrix HGU133A mircoarrays and scanned. The expression value for each gene was calculated using the Affymetrix GeneChip software and the data analyzed using the dChip software (world wide web at biosun1.harvard.edu/complab/dchip/).

Genomic DNA was isolated from HCC827 and HCC827 GR cells using the DNeasy tissue kit (Qiagen, Inc., Valencia, Calif.). Samples were processed for the Human Mapping 250K Sty single nucleotide polymorphism (SNP) array according to the manufacturer's instructions (Affymetrix Mapping 500K Assay Manual except that the MJ Research thermocycler was set to the "Block" mode, and all denaturation cycles were carried out at 92 C, four PCR reactions were run for each sample, and 120 ug of PCR product was fragmented, labeled and hybridized to each array. Comparison of gene copy number differences between HCC827 and the GR clones was performed using the dChip software according to previously established methods (33).

Quantitative PCR

The relative copy number for MET was determined using quantitative real time PCR using a PRISM 7500 sequence detection kit (Applied Biosystems) and a QuantiTect SYBR Green PCR Kit (Qiagen, Inc., Valencia, Calif.). The standard curve method was used to calculate MET gene copy number in the cell line or tumor DNA sample relative to a reference, the Line-1 repetitive element whose copy number is similar between normal and cancerous cells (33). Quantification was based on standard curves from a serial dilution of normal human genomic DNA. All specimens were analyzed in triplicate. The PCR primers are available upon request.

Xenografs

Nude mice (nu/nu; 6-8 weeks old; Charles River Laboratories) were used for in vivo studies and were cared for in accordance with the standards of the Institutional Animal Care and Use Committee (IACUC) under a protocol approved by the Animal Care and Use Committee of the Children's Hospital Boston. Mice were anesthetized using a 2% Isoflurane (Baxter) inhalation oxygen mixture. A suspension of $5 \times 10^6$ HCC827 or HCC827 GR5 lung cancer cells (in 0.2 ml of PBS) were inoculated subcutaneously into the lower-right quadrant of the flank of each mouse. Tumors were measured twice weekly using calipers, and volume was calculated using the formula (length×width$^2$×0.52). Mice were monitored daily for body weight and general condition. The tumors were harvested when their mean size reached 1000 mm$^3$.

Fluorescence In Situ Hybridization

Fluorescence in situ hybridization (FISH) was performed using a D7S522 probe and chromosome 7 centromere probe (CEP7) purchased from Vysis (Des Plaines, Ill.). Five micron (5 μm) tumor sections generated from xenografts or from patient specimen were pretreated by deparaffinizing in xylene and dehydrating in ethanol. The sections were digested by immersing in Tris-base and EDTA (TE), washing in phosphate buffered saline (PBS), and digesting with Digest-All (Zymed). The sections were fixed using formalin and dehydrated in ethanol. Co-denaturation of the sections and the probe (D7S522 and CEP7) was completed and the sections were hybridized at 37 degrees for two to three nights. Post-hybridization washes were done using saline sodium citrate and phosphate buffered saline with Tween-20 solutions and a coverslip was applied over DAPI counterstain. The D7S522 probe is contained within the small amplicon of the HCC827 GR cells (FIG. 1F). One hundred cells from each tumor specimen were analyzed and the number of D7S522 and CEP 7 signals were quantified. Cells were categorized as (1)<1 additional copy of D7S522 compared to CEP 7, (2)>2 additional copies of D7S522 compared to CEP 7, or (3)>3 additional copies of D7S522 compared to CEP 7.

Patients

Tumor specimens from gefitinib or erlotinib treated patients were obtained from the Dana Farber Cancer Institute/Brigham and Women's Hospital (Boston, Mass.), Aichi Cancer Center Hospital (Nagoya, Japan), Chinese University (Hong Kong, China) and from the Bellaria Hospital (Bologna, Italy) under Institutional Review Board Approved Studies. All patients provided written informed consent. The presence of an EGFR mutation in each specimen was using confirmed using exon specific amplification (exons 18-21), followed by subcloning and direct sequencing or by using the Surveyor™ endonuclease coupled with denaturing HPLC (DHPLC), fractionation and sequencing using previously published methods (12, 7). The detection of the EGFR T790M mutation was performed using Surveyor™ endonuclease coupled with DHPLC or by using a Cycleave real-time PCR assay (10, 32, 12). Both methods are capable of detecting the EGFR T790M mutation at an allele frequency of 1-5%.

Example 2

MET Induction Leads to EGFR Kinase Inhibitor Resistance

Figure 10:
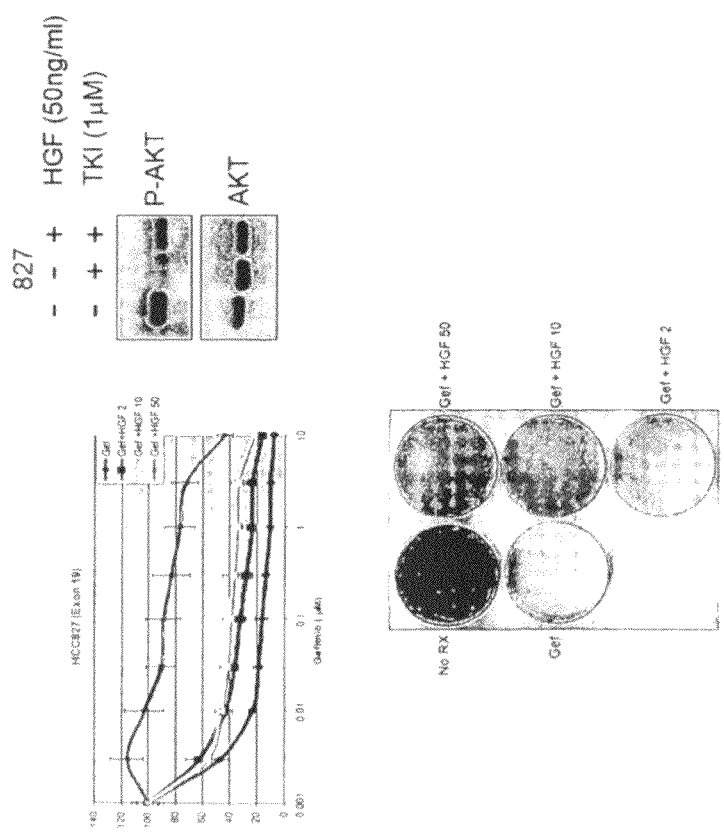
FIG. 10. Survival curve of cells treated with HGF and gefitinib. Top left panel, graph of percent viable cells versus time. The top right panel depicts a Western blot detecting Akt and phosphoryalted Akt in cells treated with hepatocyte growth factor (HGF), gefitinib (TKI), or both HGF and gefitinib. The bottom panel shows viable cells in dishes treated with HGF and gefitinib.

MET activity was induced by treating HCC827 cells with its ligand, HGF (hepatocyte growth factor). The EGFR kinase inhibitor gefitinib was co-administered. The top left panel of FIG. 10 shows the survival curve generated when HCC827 cells were treated with different concentrations of HGF (2, 10, and 50 ng/ml) and subjected to an MTS survival assay in the presence of gefitinib. Treatment with 50 ng/ml of HGF lead to markedly improved survival.

The top right panel of FIG. 10 shows that HGF maintains PI3K/AKT activation in HCC827 in the presence of gefitinib. HCC827 cells were treated with gefitinib alone or with HGF for 6 hours prior to lysis. Lysates were analyzed by western blot analysis with the indicated antibodies. The results indicate that while AKT protein levels were relatively constant, the decrease in AKT phosphorylation caused by gefitinib (TKI) treatment was at least partially reversed by HGF treatment.

The bottom panel of FIG. 10 shows cell survival when HGF and gefitnib were co-administered. 50t0K cells were seeded in a 10 cm petri dish and treated with the indicated conditions for 10 days. Gefitnib was used at 1 uM, and HGF was used at 50, 10, or 2 ng/ml. The plates were then stained with crystal violet to visualize viable cells. The untreated well shows the highest population of viable cells, and cells treated only with gefitnib showed the most cell death. Survival of gefitnib-treated cells increases with increased concentrations of HGF.

Taken together, the data indicate that ligand induced activation of MET induces resistance to EGFR TKIs in HCC827 cells.

REFERENCES

1. B. J. Druker et at., *New England Journal of Medicine* 344, 1038 (2001).
2. G. D. Demetri et at., *New England Journal of Medicine* 347, 472 (2002).
3. J. G. Paez et at., *Science* 304, 1497 (2004).
4. T. J. Lynch et at., *New England Journal of Medicine* 350, 2129 (2004).
5. H. Shigematsu et at., *Journal of the National Cancer Institute* 97, 339 (2005).
6. S. Tracy et at., *Cancer Research* 64, 7241 (2004).
7. T. Kosaka et al., *Clinical Cancer Research* 12, 5764 (2006).
8. M. N. Balak et at., *Clinical Cancer Research* 12, 6494 (2006).
9. J. A. Engelman et at., *Proc Natl Acad Sci USA* 102, 3788 (2005).
10. J. A. Engelman et at., *Journal of Clinical Investigation* 116, 2695 (2006).
11. N. V. Sergina et at., *Nature* (2007).
12. P. A. Janne et at., *Clinical Cancer Research* 12, 751 (2006).
13. E. L. Kwak et al., *Proc Nall Acad Sci USA* 102, 7665 (2005).
14. J. G. Christensen et at., *Cancer Research* 63, 7345 (2003).
15. M. Jo et at., *Journal of Biological Chemistry* 275, 8806 (2000).
16. K. M. Weidner et at., *Nature* 384, 173 (1996).
17. T. Mukohara et al., *Clinical Cancer Research* 11, 8122 (2005).
18. G. A. Smolen et al., *Proc Natl Acad Sci USA* 103, 2316 (2006).
19. M. C. Heinrich et at., *Journal of Clinical Oncology* 24, 4764 (2006).
20. M. Debiec-Rychter et at., *Gastroenterology* 128, 270 (2005).
21. A. Hochhaus et al., *Leukemia* 16, 2190 (2002).
22. M. Pocaly et al., *Leukemia* 21, 93 (2007).
23. N. J. Donato et al., *Blood* 101, 690 (2003).
24. A. Ptasznik, Y. Nakata, A. Kalota, S. G. Emerson, A. M. Gewirtz, *Nature Medicine* 10, 1187 (2004).
25. T. Kosaka et al., *Cancer Research* 64, 8919 (2004).

26. T. Shibata et al., *Clinical Cancer Research* 11, 6177 (2005).
27. A. Inoue et al., *Journal of Clinical Oncology* 24, 3340 (2006).
28. F. M. Yakes et al., *Cancer Research* 62, 4132 (2002).
29. X. Zhao et al., *Cancer Research* 64, 3060 (2004).
30. J. Amann et al., *Cancer Research* 65, 226 (2005).
31. T. Mukohara et al., *Journal of the National Cancer Institute* 97, 1185 (2005).
32. M. Park, H. Park, W. H. Kim, H. Cho, J. H. Lee, *Exp Mol Med* 37, 213 (2005).
33. X. Zhao et al., *Cancer Research* 65, 5561 (2005).

EQUIVALENTS

The present invention provides among other things methods for treating cancer using a combination of a anti-ErbB therapeutic and an anti-MET therapeutic. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) and/or the National Center for Biotechnology Information (NCBI).

What is claimed is:

1. A method for treating non-small cell lung cancer (NSCLC) or gastric cancer in a patient with an acquired resistance to treatment with an anti-ErbB therapeutic, comprising the steps of:
   a) selecting a patient with NSCLC or gastric cancer associated with an ErbB activating mutation or an ErbB gene amplification who has developed a resistance to treatment with an anti-ErbB therapeutic, and whose cancer cells comprise cells with a MET activating mutation or a MET gene amplification that reduces downregulation of PI3K/Akt signaling in response to the anti-ErbB therapeutic, and
   b) administering to said patient an anti-ErbB therapeutic and an anti-MET therapeutic.

2. The method of claim 1, wherein the subject has an EGFR, ErbB2, ErbB3, or ErbB4 activating mutation or gene amplification.

3. The method of claim 2, wherein the subject has an EGFR activating mutation or an EGFR gene amplification.

4. The method of claim 1, wherein the cancer is resistant to treatment with one or more of the following anti-ErbB therapeutics: an anti-EGFR therapeutic, an anti-ErbB2 therapeutic, an anti-ErbB3 therapeutic, or an anti-ErbB4 therapeutic.

5. The method of claim 1, wherein the cancer is resistant to treatment with one or more of the following anti-ErbB therapeutics: a small molecule therapeutic, a nucleic acid therapeutic, or a protein therapeutic.

6. The method of claim 5, wherein the cancer is resistant to treatment with an anti-ErbB antibody.

7. The method of claim 5, wherein the cancer is resistant to treatment with an ErbB kinase inhibitor.

8. The method of claim 5, wherein the cancer is resistant to treatment with an EGFR kinase inhibitor.

9. The method of claim 1, wherein the anti-ErbB therapeutic is selected from the group consisting of gefitinib, erlotinib, lapatinib, PF00299804, CI-1033, EKB-569, BIBW2992, ZD6474, AV-412, EXEL-7647, HKI-272, cetuximab, pantinumumab, and trastuzumab.

10. The method of claim 1, wherein the anti-MET therapeutic is selected from the group consisting of PHA-665,752, SU11274, SU5416, PF-02341066, XL-880, MGCD265, XL184, ARQ 197, P-470, SGX-523, JNJ38877605, AMG 102, and OA-5D5.

11. The method of claim 1, wherein:
   a) the anti-ErbB therapeutic is selected from the group consisting of gefitinib, erlotinib, lapatinib, PF00299804, CI-1033, EKB-569, BIBW2992, ZD6474, AV-412, EXEL-7647, HKI-272, cetuximab, pantinumumab, and trastuzumab; and
   b) the anti-MET therapeutic is selected from the group consisting of PHA-665,752, SU11274, SU5416, PF-02341066, XL-880, MGCD265, XL184, ARQ 197, P-470, SGX-523, JNJ38877605, AMG 102, and OA-5D5.

12. The method of claim 1, wherein the anti-ErbB therapeutic is gefitinib and the anti-MET therapeutic is PHA-665,752.

* * * * *

UNITED STATES PATENT AND TRADEMARK OFFICE
CERTIFICATE OF CORRECTION

PATENT NO. : 8,715,665 B2  Page 1 of 1
APPLICATION NO. : 12/450826
DATED : May 6, 2014
INVENTOR(S) : Janne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1160 days.

Signed and Sealed this

Twenty-ninth Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,715,665 B2
APPLICATION NO. : 12/450826
DATED : May 6, 2014
INVENTOR(S) : Janne et al.

Page 1 of 1

It is certified that error appears in the above-identified patent and that said Letters Patent is hereby corrected as shown below:

In the specification

Column 1, line 17, please change "RO1CA114465 and K08CA120060-01" to --CA114465 and CA120060--

Signed and Sealed this
Second Day of August, 2016

Michelle K. Lee
*Director of the United States Patent and Trademark Office*